United States Patent
Chen et al.

(10) Patent No.: US 7,910,621 B2
(45) Date of Patent: Mar. 22, 2011

(54) SMALL MOLECULE ANTAGONISTS OF XIAP FAMILY PROTEINS

(75) Inventors: Jianyong Chen, Ann Arbor, MI (US); Zaneta Nikolovska-Coleska, Ann Arbor, MI (US); Dajun Yang, Rockville, MD (US); Shaomeng Wang, Saline, MI (US); Haiying Sun, Ann Arbor, MI (US); Liang Xu, Ann Arbor, MI (US); Zengjian Hu, Gaithersburg, MD (US)

(73) Assignee: The Regents of the University of Michigan, Ann Arbor, MI (US)

( * ) Notice: Subject to any disclaimer, the term of this patent is extended or adjusted under 35 U.S.C. 154(b) by 903 days.

(21) Appl. No.: 10/594,200

(22) PCT Filed: Mar. 22, 2005

(86) PCT No.: PCT/US2005/009378
§ 371 (c)(1),
(2), (4) Date: Jul. 30, 2007

(87) PCT Pub. No.: WO2005/092326
PCT Pub. Date: Oct. 6, 2005

(65) Prior Publication Data
US 2008/0021095 A1    Jan. 24, 2008

Related U.S. Application Data

(60) Provisional application No. 60/555,263, filed on Mar. 22, 2004.

(51) Int. Cl.
*A61K 31/352* (2006.01)
*C07D 311/30* (2006.01)
(52) U.S. Cl. ........................................ 514/456; 549/401
(58) Field of Classification Search .................. 514/456; 549/401
See application file for complete search history.

(56) References Cited

OTHER PUBLICATIONS

Cain, (London) J. of the Chem. Soc. (1964), Part V, pp. 5472-5474.*
Cain, (London) J. of the Chem. Soc. (1963), Part I, pp. 356-359.*
Database CAPLUS Acc. No. 1963:59491, CA 58:59491, Cain BF Potential antitumor agents II. polyporic acid series', see abstract.
Database CAPLUS Acc. No. 1965:36588, Doc. No. 62:36588, Cain BF Potential antitumor agents. III. polyporic acid, see abstract.

* cited by examiner

*Primary Examiner* — Taofiq A Solola
(74) *Attorney, Agent, or Firm* — Casimir Jones SC

(57) ABSTRACT

The present invention relates to naturally occurring and chemically synthesized small molecule antagonists of XIAP family proteins. In particular, the present invention provides embelin and other XIAP inhibitors and methods of using these compounds as antagonists of the anti-apoptotic effects of XIAP family member proteins. The present invention also provides methods for treating diseases and pathologies (e.g., neoplastic diseases).

22 Claims, 18 Drawing Sheets

Figure 10.
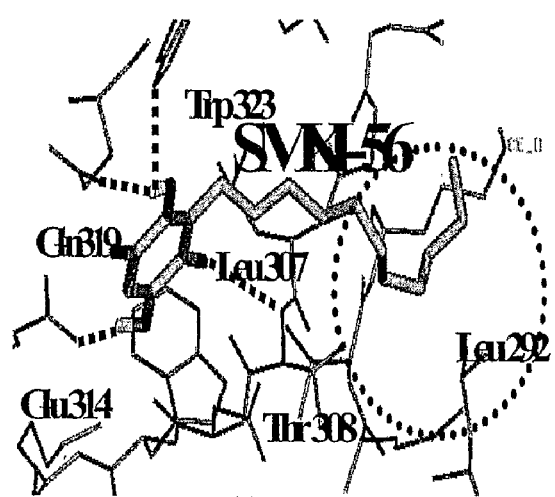
Figure 10A
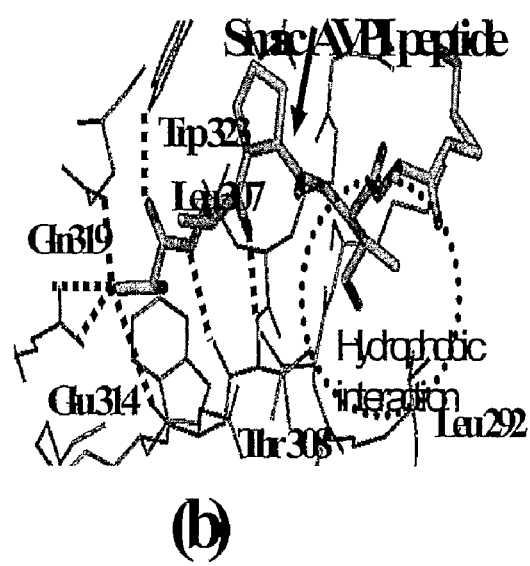
Figure 10B

Designed New Inhibitors

R= CH₃, C₂H₅, propyl, isopropyl, butyl, 2-butyl, t-butyl, n-pentyl, 2-pentyl $R_1$ and $R_2$ are lower alkyl or halo R₁ = lower alkyl; R₂ = lower alkyl, halo $R_1$ = lower alkyl; $R_2$ = lower alkyl, halo

SMALL MOLECULE ANTAGONISTS OF XIAP FAMILY PROTEINS

This Appln. is a 371 of PCT/US05/09378 filed Mar. 22, 2005 which claims benefit of 60/555,263 filed Mar. 22, 2004.

FIELD OF THE INVENTION

The present invention relates to naturally occurring and chemically synthesized small molecule antagonists of XIAP family proteins. In particular, the present invention provides embelin and other XIAP inhibitors and methods of using these compounds as antagonists of the anti-apoptotic effects of XIAP family member proteins. The present invention also provides methods for treating diseases and pathologies (e.g., neoplastic diseases).

BACKGROUND OF THE INVENTION

Multicellular organisms use a process called apoptosis to instruct damaged or unnecessary cells to destroy themselves for the good of the organism. Control of the apoptotic process is very important for the normal development of the organism. For example, fetal development of fingers and toes requires the controlled removal, by apoptosis, of excess interconnecting tissues, as does proper formation of neural synapses within the brain. Careful control of apoptosis is also important to adult organisms, for instance, controlled apoptosis is responsible for the sloughing of the inner lining of the uterus (the endometrium) at the start of menstruation.

Apoptosis not only plays an important role in tissue sculpting during fetal development and normal cellular maintenance, it is also the primary defense against rogue cells that threaten the well being of the entire organism. For instance, in the cell-mediated immune response, effector cells (e.g., cytotoxic T lymphocytes "CTLs") destroy virus-infected host cells by inducing the infected host cells to undergo apoptosis. The organism subsequently relies in turn upon the apoptotic process to destroy the effector cells when they are no longer needed. Autoimmunity is prevented by the CTLs inducing apoptosis in each other and even in themselves. Defects in this process are associated with a variety of autoimmune diseases such as lupus erythematosus and rheumatoid arthritis.

Multicellular organisms use the process to instruct cells with damaged nucleic acids (e.g., DNA) to destroy themselves prior to becoming cancerous. However, some cancer-causing viruses prevent apoptosis in transformed cells. For example, several human papilloma viruses (HPVs) are implicated in causing cervical cancer by suppressing apoptotic removal of transformed cells through the production of a protein, E6, which inactivates the p53 apoptosis promoter. Epstein-Barr virus (EBV), the causative agent of mononucleosis and Burkitt's lymphoma, a solid tumor of B-lymphocytes, produces a first protein similar to XIAP, and a second that causes transformed cells to increase production of XIAP. The expression of various XIAP family proteins helps virus-transformed cells resist apoptosis. Still other viruses manipulate the cell's apoptotic machinery without directly resulting in the development of a cancer. For example, destruction of the immune system in individuals infected with the human immunodeficiency virus (HIV) is thought to progress through infected CD4+ T cells (about 1 in 100,000) instructing their sister cells to undergo apoptosis. Faulty regulation of the apoptotic machinery has also been implicated in various degenerative conditions and vascular diseases.

Some cancers that arise by non-viral means have also developed mechanisms to escape destruction by apoptosis. Melanoma cells, for instance, avoid apoptosis by inhibiting the expression of the gene encoding the apoptosis effector protein Apaf-1. Other cancers, especially lung and colon, secrete elevated levels of soluble decoy molecules that bind FasL, inhibiting it from binding to Fas. CTLs are thus prohibited from destroying these cancer cells. Other cancer cells express high levels of FasL, again, avoiding destruction by the CTLs.

It is apparent that the controlled regulation of the apoptotic process and the apoptotic machinery is vital to the survival of multicellular organisms. Typically, the biochemical changes that occur in a cell instructed to undergo apoptosis occur in an orderly procession. However, as shown above, flawed regulation of these processes can cause serious harm.

There have been various attempts to use small molecules to control and restore regulation of the apoptotic machinery in aberrant cells (e.g., cancer cells). Generally, these attempts have had limited success as treatments for the underlying diseases for a number of reasons, including high toxicity, low bioavailability, high costs, and the like. What is needed are improved methods and compositions for regulating apoptosis in subjects afflicted with diseases and conditions that are characterized by faulty regulation of the apoptotic process.

SUMMARY OF THE INVENTION

The present invention relates to naturally occurring and chemically synthesized small molecule antagonists of XIAP family proteins. In particular, the present invention provides XIAP inhibitor compounds (e.g., isomers, enantiomers, racemic compounds, metabolites, derivatives, pharmaceutically acceptable salts, in combination with acids or bases, and the like) and methods of using these compounds as antagonists of the anti-apoptotic effects of XIAP family member proteins. The present invention also provides methods for treating diseases and pathologies (e.g., neoplastic diseases).

DESCRIPTION OF THE FIGURES

The following figures form part of the specification and are included to further demonstrate certain aspects and embodiments of the present invention. The present invention is not intended to be limited however to the embodiments specifically recited in these figures.

normal human prostate epithelial cells. WI-38: normal human fibroblast cell line. HSP70: heat shock protein 70 kDa for gel loading control.

Figure 5:
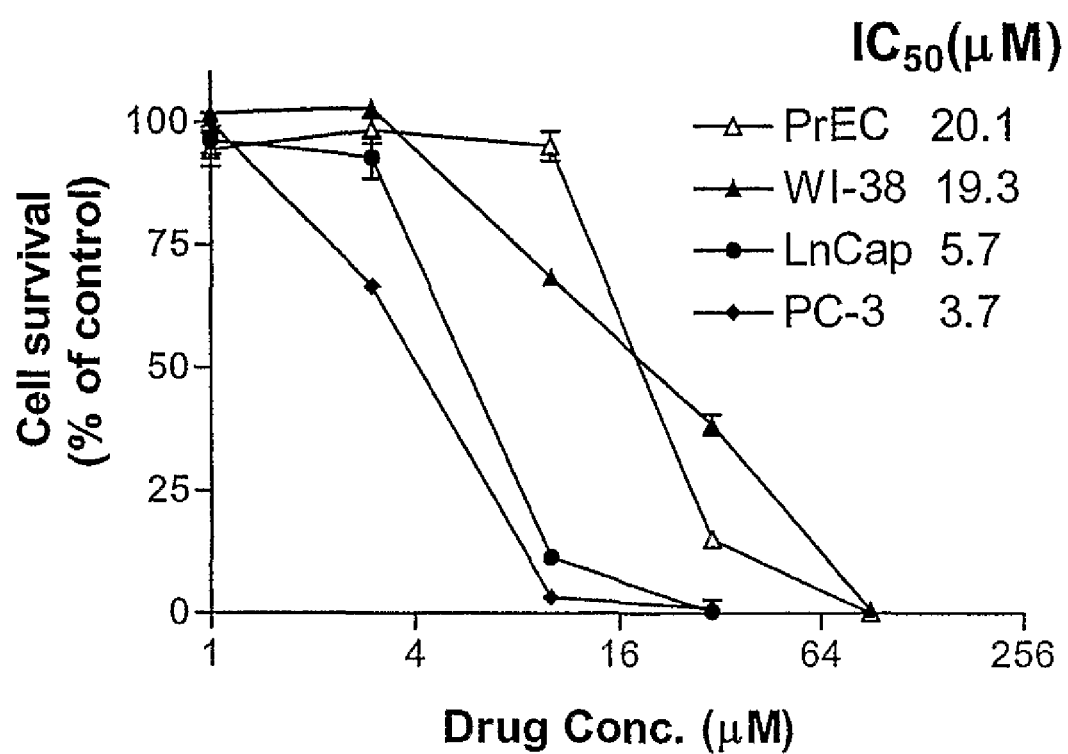

FIG. 5 presents inhibition of cell growth by embelin in prostate cancer cells (PC-3 and LnCap) and its selectivity in normal human prostate epithelial cells (PrEC) and normal human fibroblast cell line, WI-38. 5000 cells per well in a 96-well cell culture plate were treated with various concentrations of embelin in triplicate. Five days later, the cell growth was measured by the WST-1 cell growth assay kit Δ The cell growth results are expressed as the percent of control and calculated from the percent of absorbance of treated wells versus that of vehicle control. $IC_{50}$ value is the drug concentration needed to achieve 50% cell growth inhibition versus control cells.

Figure 6:
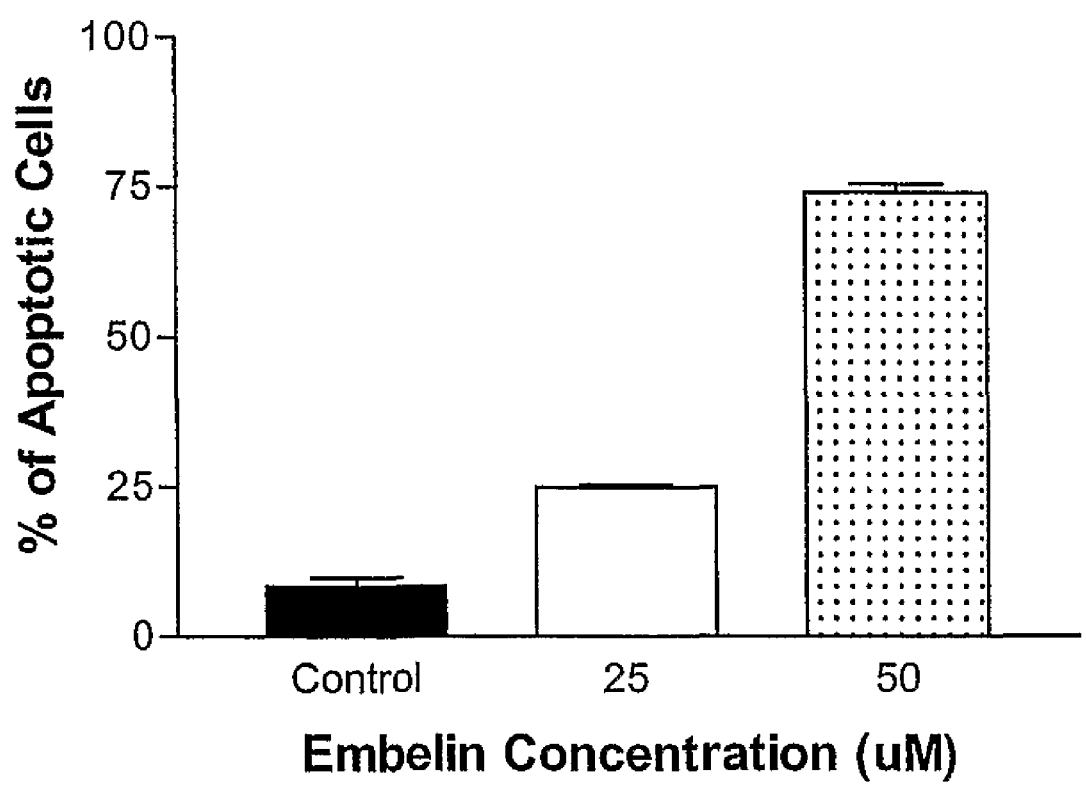

FIG. 6 presents induction of apoptosis by embelin in PC-3 prostate cancer cells. $1 \times 10^6$ PC-3 cells per well in 6-well culture plates were treated with embelin for 48 hours, stained with Annexin V-FITC and propidium iodide for apoptosis by flow cytometry. The results are shown as percent of Annexin V-FITC positive apoptotic cells (n=3).

Figure 7A:
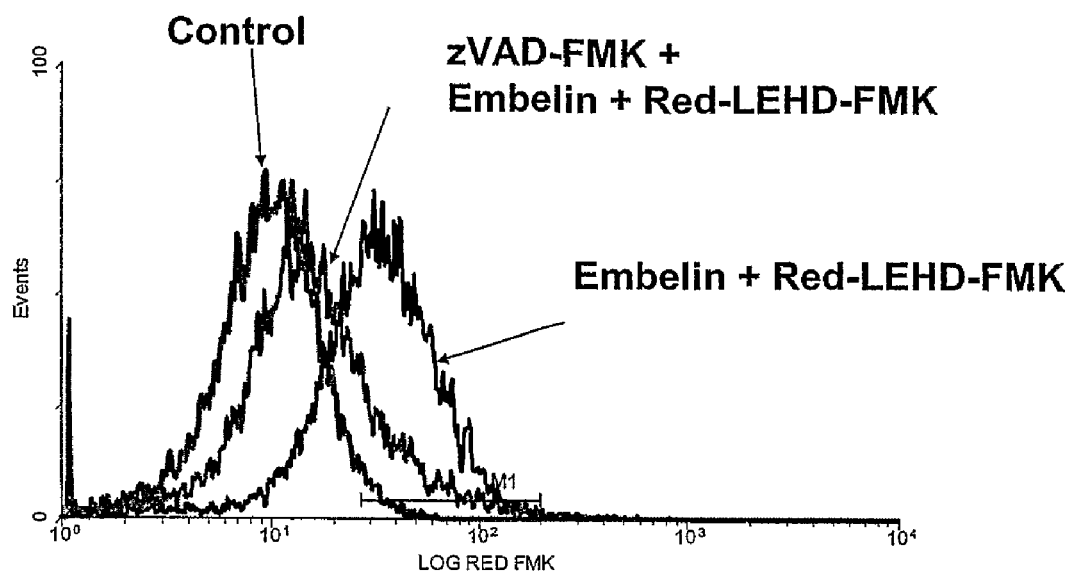
Figure 7B:
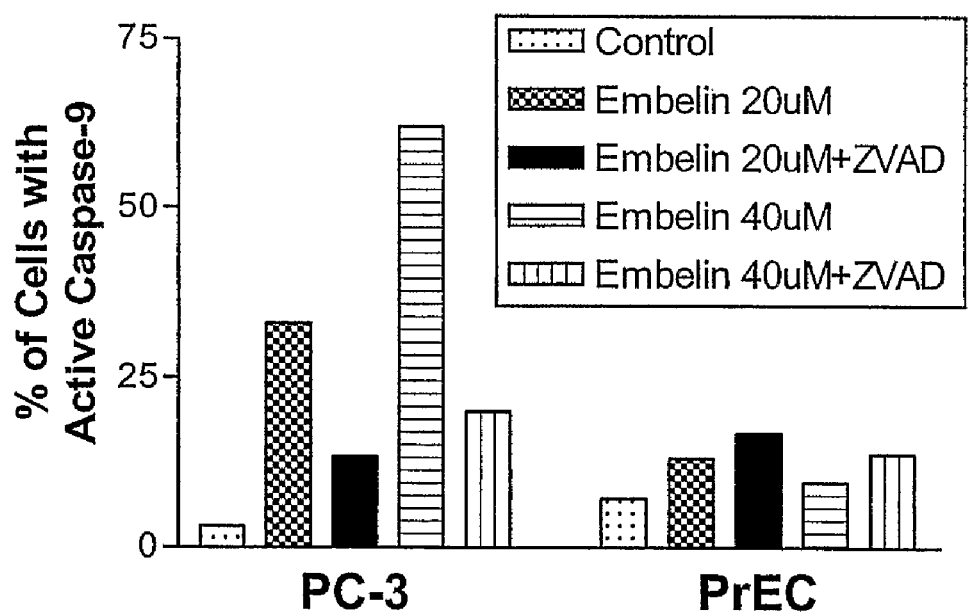

FIGS. 7A and 7B show the activation of caspase-9 by embelin in PC-3 prostate cancer cells and its selectivity in normal prostate epithelial cells. $1 \times 10^6$ PC-3 or PrEC cells per well in 6-well culture plates were treated with embelin for 48 hours. An additional control was prepared by adding the pan-caspase inhibitor Z-VAD-FMK (2 uM final) 5 min before adding embelin, to inhibit caspase activation. The cells were collected and stained of active caspase-9 by CaspGLOW Red Active Caspase-9 Staining Kit, and analyzed by flow cytometry in PI channel. Embelin effectively activates caspase-9 in PC-3 cells in a dose-dependant manner, but has minimal effects on normal PrEC cells.

Figure 8A:
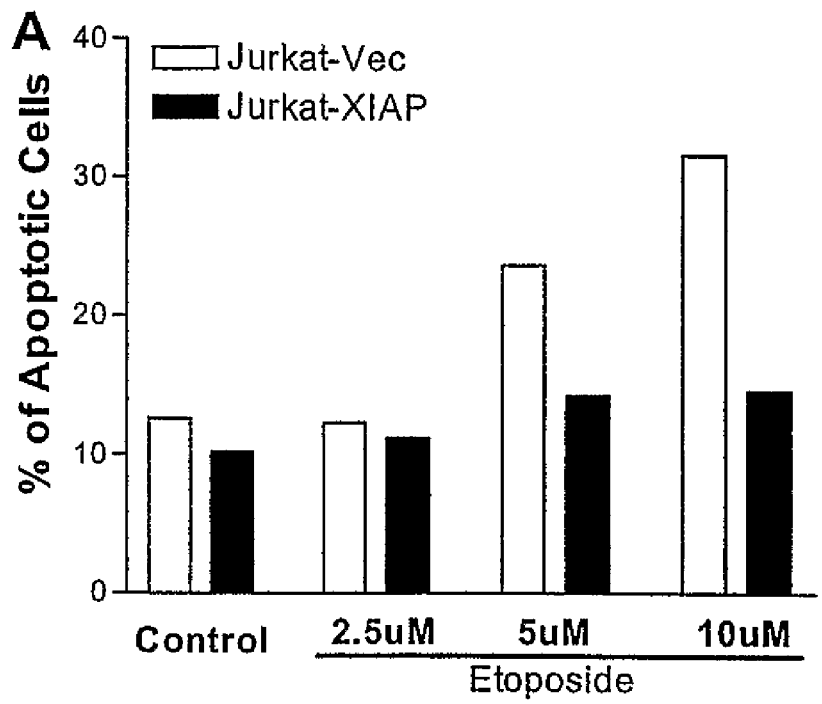
Figure 8B:
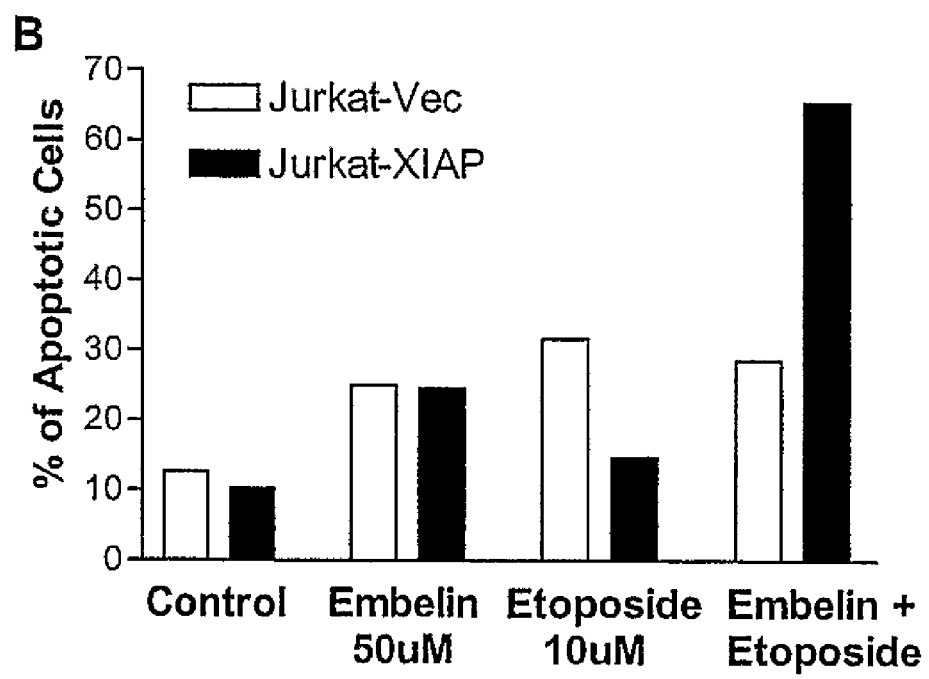

FIGS. 8A and 8B present (A): Dose-dependent induction of apoptosis by etoposide in Jurkat cells transfected with vector control (Jurkat-Vec) and stably transfected with XIAP (Jurkat-XIAP cells); and (B): Induction of apoptosis by etoposide and embelin alone and in combination in Jurkat-Vec and Jurkat-XIAP cells. $1 \times 10^6$ Jurkat-XIAP or Jurkat-Vec cells per well in 6-well culture plates were treated with etoposide and embelin alone, or in combination for 15 hours, then stained with Annexin V-FITC and propidium iodide for apoptosis by flow cytometry. The results are shown as percent of Annexin V-FITC positive apoptotic cells.

Figure 9:
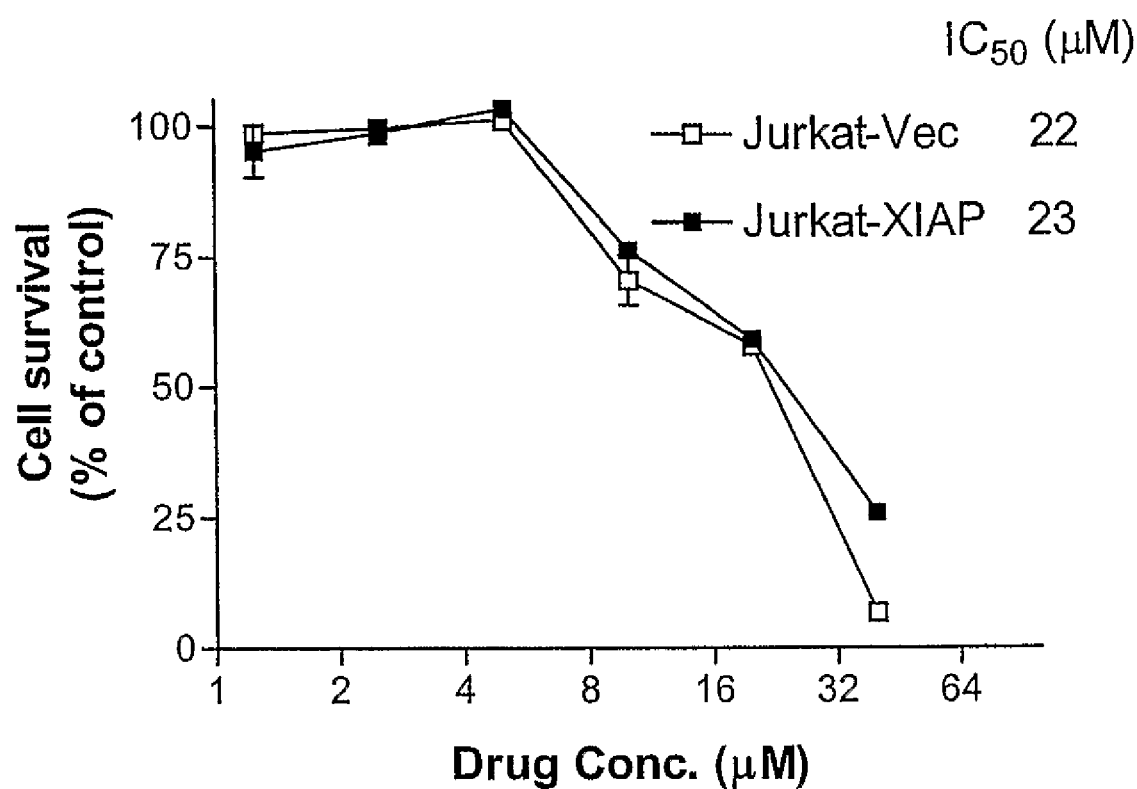

FIG. 9 presents inhibition of cell growth by embelin in Jurkat-Vec and Jurkat-XIAP cells. The cell growth results are expressed as the percent of control and calculated from the percent of absorbance of treated wells versus that of vehicle control. $IC_{50}$ value is the drug concentration needed to achieve 50% cell growth inhibition versus control cells.

FIGS. 10A and 10B presents (A) a binding model of SMXI-56 (embelin) in complex with XIAP. SMM-56 forms a number of hydrogen bonds with residues Leu307 (backbone atom), Gln 310 (side chain), Glu314 (side chain) and Trp323 (side chain). In addition, SMXI-56 has hydrophobic interactions with Leu307 and Leu292; and (B) the X-ray structure of Smac in complex with XIAP. Hydrogen bonding network is shown in dashed lines and a key hydrophobic interaction is depicted in cycle.

Figure 11:
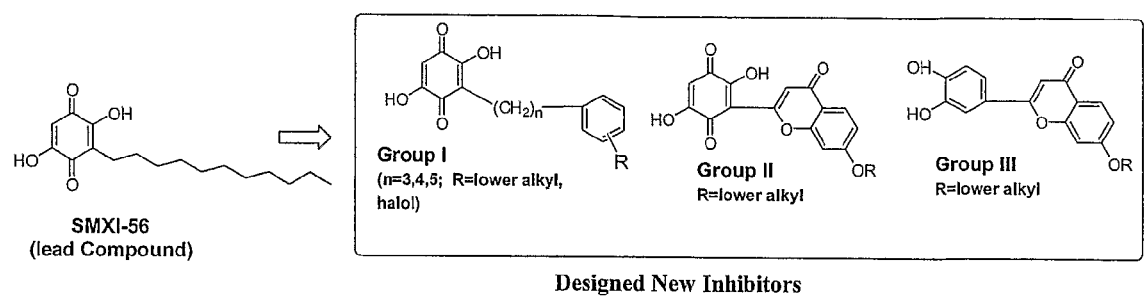

FIG. 11 presents inhibitors of XIAP.

Figure 12:
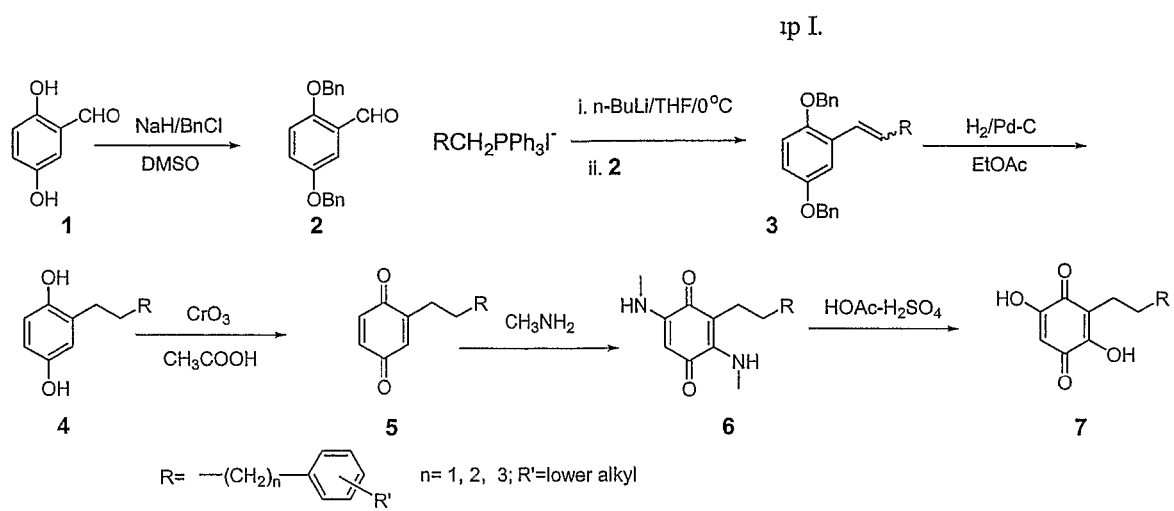

FIG. 12 presents a chemical synthesis of analogues of SMXI-56 in GROUP I.

Figure 13:
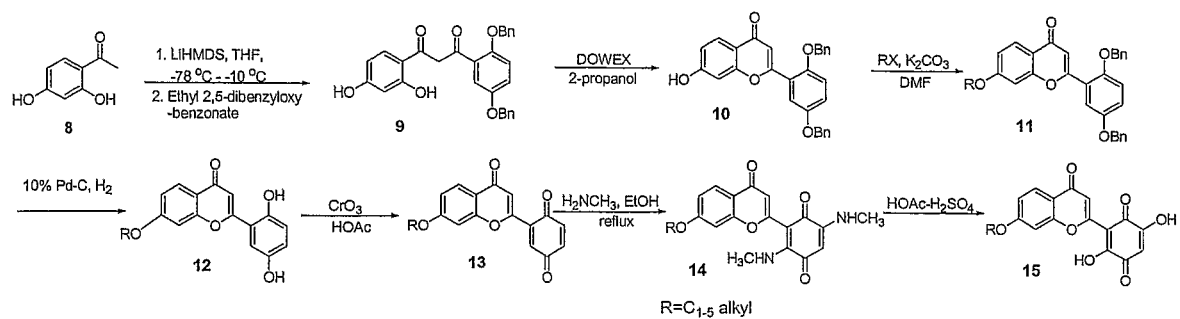

FIG. 13 presents a chemical synthesis of analogues of SMXI-56 in GROUP II.

Figure 14:
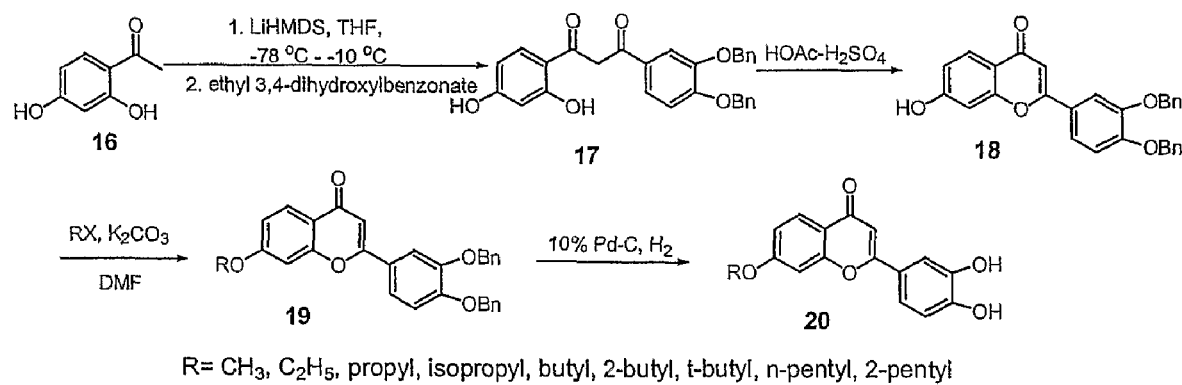

FIG. 14 presents a chemical synthesis of analogues of SMXI-56 in GROUP III.

Figure 15:
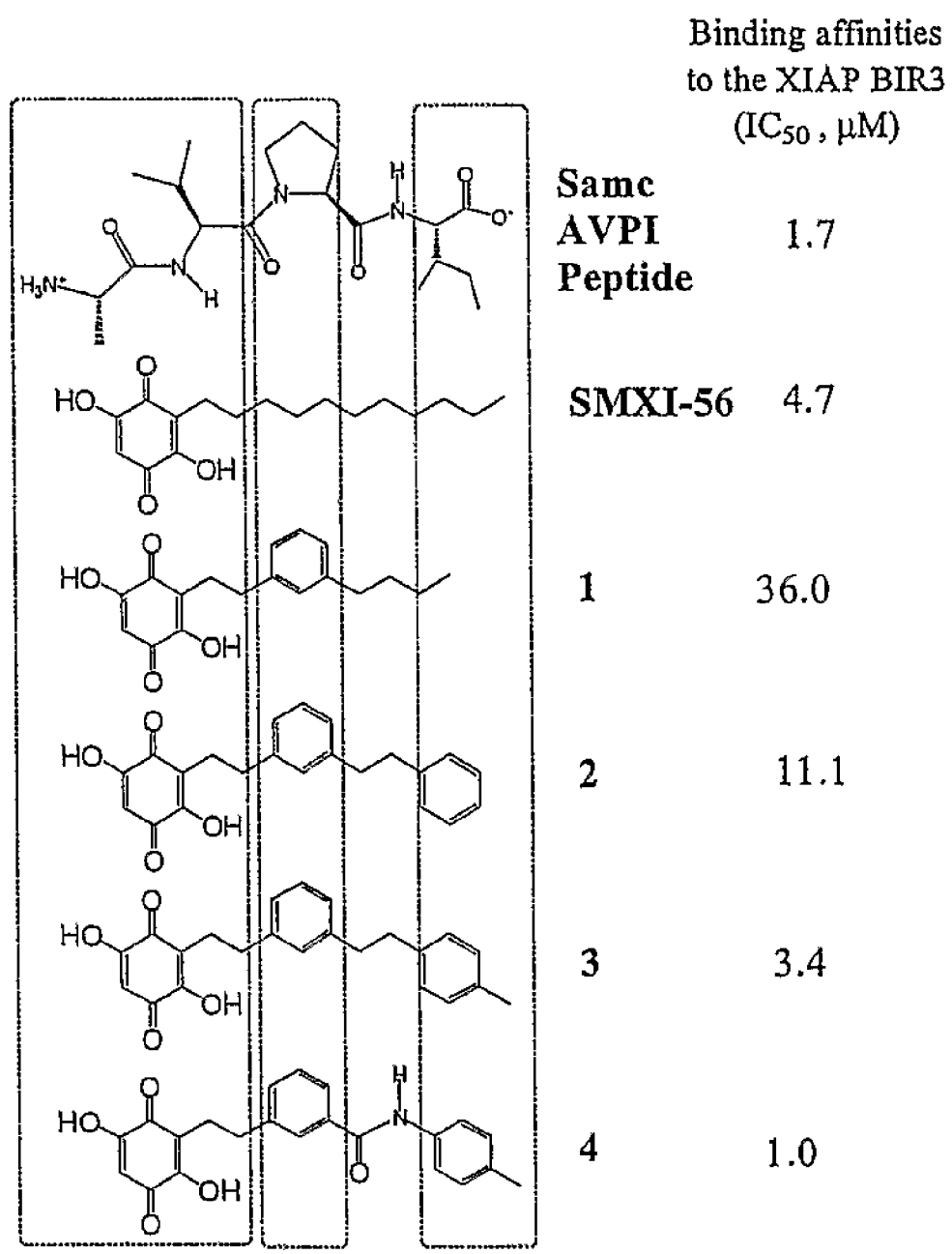

FIG. 15 presents XIAP inhibitors based on lead compound SMXI-56.

Figure 16:
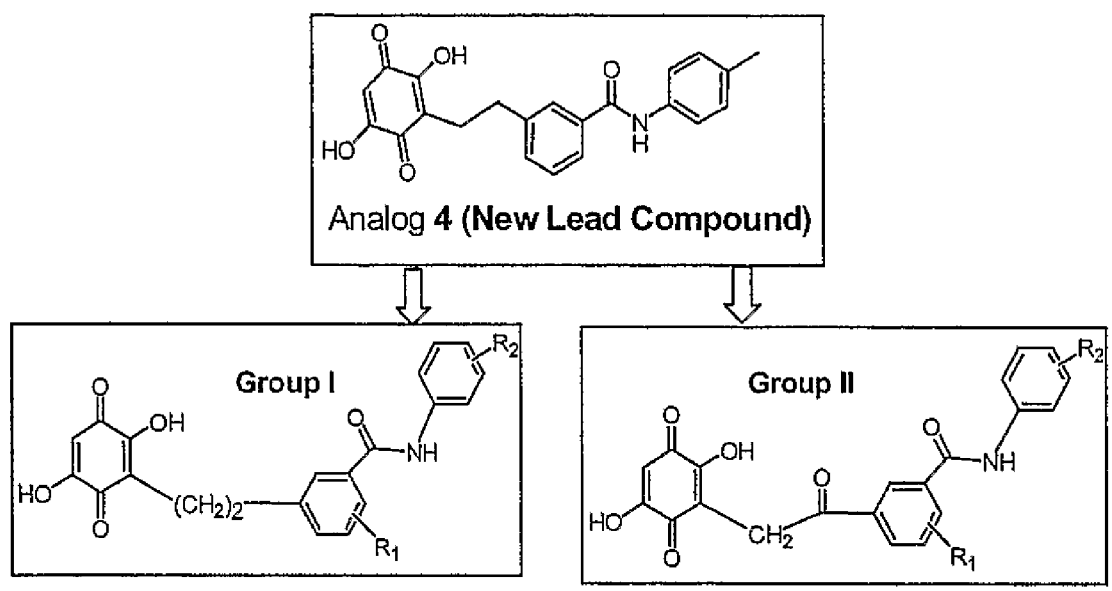

FIG. 16 presents inhibitors of XIAP based upon analog 4 as a lead compound.

Figure 17:
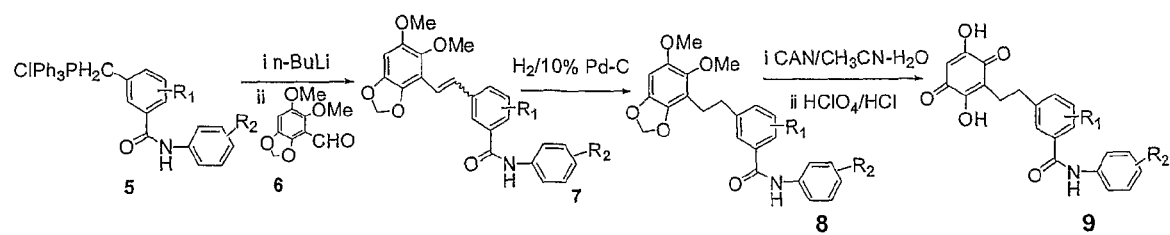

FIG. 17 presents a synthesis scheme of designed compounds in alternative-GROUP I.

Figure 18:
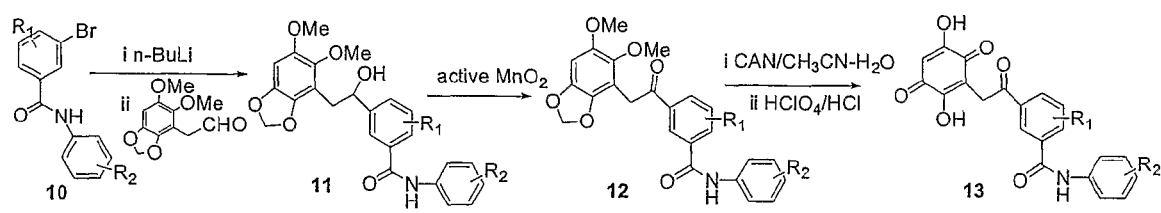

FIG. 18 presents a synthesis scheme of designed compounds in alternative-GROUP II.

DEFINITIONS

To facilitate an understanding of the present invention, a number of terms and phrases are defined below.

As used herein, the terms "overexpression of XIAP" or "overexpression of a XIAP family protein" refer to an elevated level (e.g., aberrant) of mRNAs encoding for a XIAP family protein(s), and/or to elevated levels of such XIAP family protein(s) in cells or tissues as compared to similar normal corresponding nonpathological cells and tissues expressing basal levels of mRNAs encoding XIAP family proteins or having basal levels of XIAP family proteins. Methods for detecting the levels of mRNAs encoding XIAP family proteins, or levels of XIAP family proteins, in a cell or tissue include, but are not limited to, Western blotting using XIAP family protein antibodies, immunohistochemical methods, and methods of nucleic acid amplification or direct RNA detection. As important as the absolute levels of XIAP family proteins in cells, tissues, or organs are to determining that they overexpress XIAP family proteins, so also are the relative levels of anti-apoptotic XIAP family proteins to other pro-apoptotic signaling molecules (e.g., pro-apoptotic XIAP family proteins) within such cells, tissues or organs. When the balance of these two are such that, were it not for the levels of the anti-apoptotic XIAP family proteins, the pro-apoptotic signaling molecules would be sufficient to cause the cells to execute the apoptosis program and die, said cells in such tissues or organs would be dependent on the anti-apoptotic XIAP family proteins for their survival. In such cells, exposure to an inhibiting effective amount of an anti-apoptotic XIAP family protein inhibitor will be sufficient to cause the cells to execute the apoptosis program and die. Thus, the term "overexpression of XIAP family protein" also refers to cells in tissues and organs that, due to the relative levels of pro-apoptotic signals and anti-apoptotic signals, undergo apoptosis in response to inhibiting effective amounts of compounds that inhibit the function of anti-apoptotic XIAP proteins.

As used herein, the term "XIAP inhibitor" refers to any natural or non-natural compound that inhibits at least one biological activity (e.g., anti-apoptotic activity) of the XIAP protein.

As used herein, the term "non-natural XIAP inhibitor" refers to an inhibitor of XIAP that is not known found in nature. For example, non-natural XIAP inhibitors are chemically synthesized in the laboratory and represent novel compounds not identified in nature.

As used herein, the term "embelin compound" refers to embelin, as well as derivatives, acids, enantiomers, isomers, analogs, metabolites, or pharmaceutically acceptable salts of embelin.

As used herein, the terms "anticancer agent," "conventional anticancer agent," or "cancer therapeutic drug" refer to any therapeutic agents (e.g., chemotherapeutic compounds and/or molecular therapeutic compounds), radiation therapies, or surgical interventions, used in the treatment of cancer (e.g., in mammals).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

As used herein the term "prodrug" refers to a pharmacologically inactive or substantially pharmacologically inactive derivative of a parent "drug" molecule that requires transformation (e.g., either spontaneous or enzymatic) within the target physiological system to release, or to convert (e.g., enzymatically, mechanically, electromagnetically, etc.) the "prodrug" into the active "drug." "Prodrugs" are designed to overcome problems associated with stability, toxicity, lack of specificity, or limited bioavailability. Exemplary "prodrugs" comprise an active "drug" molecule itself and a chemical masking group (e.g., a group that reversibly suppresses the activity of the "drug"). Some preferred "prodrugs" are variations or derivatives of compounds that have groups cleavable under metabolic conditions. Exemplary "prodrugs" become pharmaceutically active in vivo or in vitro when they undergo solvolysis under physiological conditions or undergo enzymatic degradation or other biochemical transformation (e.g., phosphorylation, hydrogenation, dehydrogenation, glycosylation, etc.). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common "prodrugs" include acid derivatives such as esters prepared by reaction of parent acids with a suitable alcohol (e.g., a lower alkanol), amides prepared by reaction of the parent acid compound with an amine (e.g., as described above), or basic groups reacted to form an acylated base derivative (e.g., a lower alkylamide).

The term "derivative" of a compound, as used herein, refers to a chemically modified compound wherein the chemical modification takes place either at a functional group of the compound, aromatic ring, or carbon backbone. Such derivatives include esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

An "effective amount" is an amount sufficient to effect beneficial or desired results. An effective amount can be administered in one or more administrations.

As used herein, the term "administration" refers to the act of giving a drug, prodrug, or other agent (e.g., a XIAP inhibitor compound), or therapeutic treatment (e.g., radiation therapy) to a physiological system (e.g., a subject or in vivo, in vitro, or ex vivo cells, tissues, and organs). Exemplary routes of administration to the human body can be through the eyes (opthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Coadministration" refers to administration of more than one chemical agent (e.g., a compound and/or drugs, prodrugs, etc.) or therapeutic treatment (e.g., radiation therapy) to a physiological system (e.g., a subject or in vivo, in vitro, or ex vivo cells, tissues, and organs). "Coadministration" of the respective chemical agents (e.g., a XIAP inhibitor compound and/or drugs, prodrugs, etc.) and therapeutic treatments (e.g., radiation therapy) may be concurrent, or in any temporal order or physical combination.

As used herein, the term "pharmacological properties" refers to any desirable or favorable biological activities or physicochemical characteristics of an agent (e.g., a XIAP inhibitor compound) administered to a physiological system.

As used herein, the term "pharmacokinetic properties" refers to the action of an agent (e.g., a XIAP inhibitor compound) in a subject, cell, tissue, or organ over a period of time including, but not limited to, the processes of absorption, distribution, localization in tissues, biotransformation, and excretion.

As used herein, the term "bioavailability" refers to any measure of the ability of a an agent (e.g., a XIAP inhibitor compound) to be absorbed into a biological target fluid (e.g., blood, cytoplasm, CNS fluid, and the like), tissue, organelle or intercellular space after administration to a physiological system (e.g., a subject or in vivo, in vitro, or ex vivo cells, tissues, and organs).

As used herein, the term "biodistribution" refers to the location of an agent (e.g., a XIAP inhibitor compound) in organelles, cells (e.g., in vivo or in vitro), tissues, organs, or organisms, after administration to a physiological system.

As used herein, the term "dysregulation of the process of cell death" refers to any aberration in the ability of (e.g., predisposition) a cell to undergo cell death via either necrosis or apoptosis. Dysregulation of cell death is associated with or induced by a variety of conditions, including for example, autoimmune disorders (e.g., systemic lupus erythematosus, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disease," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell or tissue means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, Celiac Sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

As used herein, the term "neoplastic disease" refers to any abnormal growth of cells or tissues being either benign (non-cancerous) or malignant (cancerous).

As used herein, the term "anti-neoplastic agent" refers to any compound that retards the proliferation, growth, or spread of a targeted (e.g., malignant) neoplasm.

As used herein, the term "regression" refers to the return of a diseased subject, cell, tissue, or organ to a non-pathological, or less pathological state as compared to basal nonpathogenic exemplary subject, cell, tissue, or organ. For example, regression of a tumor includes a reduction of tumor mass as well as complete disappearance of a tumor or tumors.

As used herein, the terms "prevent," "preventing," and "prevention" refer to a decrease in the occurrence of hyperproliferative or neoplastic cells in a subject. The prevention may be complete, e.g., the total absence of hyperproliferative or neoplastic cells in a subject. The prevention may also be partial, such that the occurrence of hyperproliferative or neoplastic cells in a subject is less than that which would have occurred without the present invention.

As used herein the term, "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reactions that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "subject" refers to organisms to be treated by the methods of the present invention. Such organisms include, but are not limited to, humans and veterinary animals (dogs, cats, horses, pigs, cattle, sheep, goats, and the like). In the context of the invention, the term "subject" generally refers to an individual who will receive or who has received treatment (e.g., administration of).

The term "diagnosed," as used herein, refers to the recognition of a disease by its signs and symptoms (e.g., resistance to conventional cancer therapies), or genetic analysis, pathological analysis, histological analysis, and the like.

As used herein, the term "competes for binding" is used in reference to a first molecule with an activity that binds to the same target as does a second molecule. The efficiency (e.g., kinetics or thermodynamics) of binding by the first molecule may be the same as, or greater than, or less than, the efficiency of the target binding by the second molecule. For example, the equilibrium binding constant ($K_d$) for binding to the target may be different for the two molecules.

The term "sample" as used herein is used in its broadest sense. A sample suspected of indicating a condition characterized by the overexpression of a XIAP family protein may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of XIAP family proteins in a cell). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In preferred embodiments, "test compounds" are anticancer agents. In particularly preferred embodiments, "test compounds" are anticancer agents that induce apoptosis in cells.

As used herein, the term "purified" or "to purify" refers to the removal of undesired components from a sample. As used herein, the term "substantially purified" refers to molecules (e.g., polynucleotides, polypeptides, chemical compounds (e.g., XIAP inhibitor compounds)) that are removed from their natural environment, isolated or separated, and are at least 60% free, preferably at least 75% free, and most preferably at least 90% free from other components with which they are naturally associated.

As used herein, the term "pathogen" refers to a biological agent that causes a disease state (e.g., infection, cancer, etc.) in a host. "Pathogens" include, but are not limited to, viruses, bacteria, archaea, fungi, protozoans, mycoplasma, and parasitic organisms.

As used herein, the term "microorganism" is used to refer to any species or type of microorganism, including but not limited to, bacteria, archaea, fungi, protozoans, mycoplasma, and parasitic organisms. As used herein, the term "fungi" is used in reference to eukaryotic organisms such as the molds and yeasts, including dimorphic fungi.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

The terms "bacteria" and "bacterium" refer to all prokaryotic organisms, including those within all of the phyla in the kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process which is well known in the art. (See e.g., Finegold and Martin, Diagnostic Microbiology, 6th Ed., CV Mosby St. Louis, pp 13-15 (1982)). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the term "instructions for administering said compound to a subject" includes instructions for using the compositions contained in the kit for the treatment of conditions characterized by. In some embodiments, the instructions further comprise a statement of the recommended or usual dosages of the compositions contained within the kit pursuant to 21 C.F.R. §201 et seq. Additional information concerning labeling and instruction requirements applicable to the methods and compositions of the present are available at the Internet web page of the U.S.F.D.A.

As used herein, the term "third party" refers to any entity engaged in selling, warehousing, distributing, or offering for sale a compound contemplated for co-administration with a XIAP inhibitor compound for treating conditions characterized by the overexpression of the XIAP family proteins.

As used herein, the term "modulate" refers to the activity of a compound (e.g., XIAP inhibitor compound) to affect (e.g., to promote or retard) an aspect of the cellular function including, but not limited to, cell growth, proliferation, invasion, angiogenesis, apoptosis, and the like.

DETAILED DESCRIPTION OF THE INVENTION

The inhibitors of apoptosis proteins (IAPs) were recently discovered as an important class of intrinsic cellular inhibitors of apoptosis (See e.g., Deveraux et al., (1999) *Genes Dev.* 13, 239-252), although their functions may not be limited to the regulation of apoptosis (Salvesen et al., (2002) *Nat Rev Mol Cell Biol.* 3, 401-10. XIAP (X-linked IAP) is the most potent inhibitor of apoptosis among all the IAP proteins (Salvesen et al., supra). XIAP protein potently inhibits both intrinsic and extrinsic apoptosis pathways by binding and inhibiting the initiator caspase-9 and effector caspases (caspase-3 and -7), whose activity is crucial for the execution of apoptosis (Salvesen et al., supra). While the third BIR domain (BIR3) selectively inhibits caspase-9, the linker region between BIR1 and BIR2 inhibits caspase-3 and -7 (Salvesen et al., supra; Deveraux et al., (1999) *EMBO J.* 18, 5242-5251; Huang et al., (2001) *Cell,* 104, 781-790).

Although the precise role of the endogenous XIAP in the pathological process remains far from completely understood, recent data point to an important role of XIAP in the oncogenic process (Huang et al., (2001) Cell, 104, 781-790). XIAP protein was found to be widely expressed in human cancer cell lines and human cancer tissues (Holick et al., (2001) Apoptosis 6, 253-61). Apoptotic resistance was found to correlate with the expression levels of XIAP in human prostate and non-small cell lung cancer cells (McEleny et al., (2002) Prostate 51, 133-40; Tang et al., (1998) 58, 3466-79). The direct role of XIAP in the resistance of cancer cells to radiation was demonstrated using an XIAP antisense approach (Holick et al., (2000) Oncogene 19, 4174-4177). XIAP blocks apoptosis induced by taxol in human prostate LNCaP cancer cells and by Apo2L/TRAIL ligand in the hormone-independent human prostate cancer cell lines (Nomura et al., (2003) Urol Res. 31, 37-44; Ng et al., (2002) Mol Cancer Ther. 1, 1051-8). Conversely, down-regulation of XIAP has been implicated to play an important role in the synergistic induction of apoptosis by complementation with Apo2/TRAIL and actinomycin D in CL-1, DU-145, and PC-3 prostate cancer cells (Ng et al., (2002) Prostate 53, 286-99). Down-regulation of anti-apoptotic proteins, including XIAP, was implicated in apoptosis induced by protein kinase inhibitors flavopiridol and 7-hydroxy-staurosporine in B-cell chronic lymphocytic leukemia cells (Kitada et al., (200) Blood 96, 393-7). Down-regulation of XIAP protein induces apoptosis in chemoresistant, P53 wild-type human ovarian cancer but not in the P53 mutated or null cells (Sasaki et al., (2000) Cancer Res. 60, 5659-66). Inactivation of XIAP has been shown to play a role in apoptosis induced by phenoxodiol in ovarian cancer cells (Kamsteeg et al., (2003) Oncogene 22, 2611-20). Down-regulation of XIAP and other IAP proteins was also observed in mitotic arrest and apoptosis induced by Epothilone B in cisplatinum- and paclitaxel-resistant ovarian cancer cells (Griffin et al., (2003) Gynecol Oncol. 89:37-47). Recently, overexpression of XIAP has been linked to the resistance of human non-small cell lung cancer H-460 cells to chemotherapeutic agents (Yang et al., (2003) Cancer Res. 63, 831-37). The present invention is not limited to a particular mechanism. Indeed, an understanding of the mechanism is not necessary to practice the present invention. Nonetheless, it is contemplated that these studies demonstrate that XIAP may play a critical role for the resistance of cancer cells to current chemotherapeutic agents, radiation and TRAIL ligand and direct inhibition of XIAP may represent a promising strategy for the development of an entirely new class of anticancer drugs. Because XIAP blocks apoptosis at the down-stream effector phase, a point where multiple signaling pathways converge, strategies targeting XIAP may prove to be especially effective to overcome apoptosis resistance of cancer cells.

Experiments conducted during the course of development of the present invention comprised the design of small molecule inhibitors that target the XIAP BIR3 domain. The BIR3 domain is a desirable target for several reasons. First, the XIAP BIR3 domain potently binds to caspase-9, traps caspase-9 in its inactive monomeric form and prevents the formation of the active dimer of caspase-9. Although XIAP also directly binds to caspase-3 and -7 through the linker region between its BIR2 and BIR3 domains, its binding to caspase-9 through its BIR3 domain is most important for its anti-apoptotic activity. Secondly, the structural basis of the interaction of the XIAP BIR3 domain with caspase-9 has recently been elucidated in detail through the determination of a high-resolution experimental three-dimensional (3D) structure (Shiozaki et al., (2003) Mol Cell 11:519-27). Thirdly, Smac/DIABLO (second mitochondria-derived activator of caspases, or direct IAP binding protein with low pI), a protein released from mitochondria in response to apoptotic stimuli, was shown to interact directly with the XIAP BIR3 domain and other IAP proteins and promotes apoptosis in cells by antagonizing IAPs and promoting the activity of caspase-9 (Du et al., (2000) Cell 102, 33-42; Verhagen et al., (2000) Cell 102, 43-53). High-resolution 3D structures of Smac protein and peptide in complex with the BIR3 domain of XIAP clearly showed that Smac interacts with the XIAP BIR3 domain through four residues (Alanine-Valine-Proline-Isoleucine, or AVPI (Seq ID NO:1)) at the free N-terminus of Smac and a well-defined binding pocket in XIAP (Wu et al., (2000) Nature 408, 1008-12; Liu et al., (2000) Nature 408, 1004-8). Smac and caspase-9 share a common four-residue IAP binding motif (or IBM) with which to bind to the surface binding groove in the XIAP BIR3 domain (Srinivasula et al., (2001) Nature 410, 112-6; Shi et al., (2002) Cell Death Differ 9, 93-95). Smac functions as an endogenous inhibitor of XIAP through targeting the XIAP BIR3 domain and removing the inhibitory effect of XIAP to caspase-9 through a competitive binding mechanism. Fourthly, in contrast to most other protein-protein interactions, the interaction of the XIAP BIR3 domain with caspase-9/Smac is mediated by a small and well-defined binding groove in the BIR3 domain of XIAP and only four residues in Smac/caspase-9 proteins, making this site especially suitable for designing drug-like, small molecule inhibitors of XIAP (Wu et al., supra; Liu et al., supra). Finally, three independent studies demonstrated that short Smac peptides tethered to a carrier peptide for intracellular delivery overcome resistance of cancer cells to apoptosis and enhance the anti-cancer activity of current anticancer drugs in vitro and in vivo (Fulda et al., (2002) Nature Med. 8, 808-815; Yang et al., (2003) Cancer Res. 63, 831-37; Arnt et al., (2002) J. Biol. Chem. 277, 44236-43). These cell-permeable Smac-based peptides have little toxicity to normal cells or tissues in vitro and in vivo (Fulda et al., (2002) Nature Med. 8, 808-815; Yang et al., (2003) Cancer Res. 63, 831-37; Arnt et al., (2002) J. Biol. Chem. 277, 44236-43). XIAP and cIAP were identified as the primary molecular targets for these Smac-based peptides in cells (Arnt et al., supra). It was also shown that the defect in apoptosome activity was restored by cell-permeable Smac peptides by disrupting XIAP-caspase-9 binding in non-small cell lung cancer H460 cells (Yang et al., supra). It is contemplated that small molecule drugs that bind to the XIAP BIR3 domain serve as a new class of therapeutic agents to overcome apoptosis resistance of cancer cells with high levels of XIAP, as well as the treatment of other conditions caused by a failure of cells to undergo apoptosis.

Peptide-based inhibitors derived from Smac and caspase-9 proteins serve as pharmacological tools to elucidate the anti-apoptotic function of XIAP and the role of XIAP in response of cancer cells to chemotherapeutic agents. But peptide-based inhibitors have intrinsic limitations as potentially useful therapeutic agents. These limitations include their poor cell-permeability and poor in vivo stability. For example, Smac-based peptide inhibitors have to be fused to carrier peptides to make them relatively cell-permeable (Fulda et al., (2002) Nature Med. 8, 808-815; Yang et al., (2003) Cancer Res. 63, 831-37; Arnt et al., (2002) J. Biol. Chem. 277, 44236-43). Accordingly, in some embodiments, the present invention provides non-peptidic, small molecule inhibitors that directly bind to the BIR3 domain of XIAP.

Traditional herbal medicine is a rich source for modern, molecular target-specific drug discovery. In the last several decades, a tremendous amount of effort has been invested to isolate individual compounds from traditional herbal medicine and to determine their chemical structures. Many of these natural products have been screened for anticancer activity in cancer cells and in animal models of human cancer.

Experiments conducted during the course of development of the present invention utilized a systematic and structure-based approach to discover lead compounds for molecularly targeted anticancer drug discovery. These studies utilized a searchable three-dimensional structural database (TCM-3D) containing 8,221 small organic molecules with diverse chemical structures isolated from nearly 1000 traditional Chinese medicinal herbs. Unlike most commercial databases, all the compounds in the TCM 3D-database are natural products derived from traditional medicinal herbs, which have been used for medicinal purposes in China and other countries for centuries. The extensive use of these traditional Chinese medicine recipes in humans has generated a great amount of data about their efficacy and safety. The TCM-3D database is a rich resource for molecularly-targeted anticancer drug discovery.

Experiments conducted during the course of development of the present invention identified embelin and a variety of other small molecules as potent, non-peptidic, cell-permeable inhibitors that target the XIAP BIR3 domain through computational structure-based computer screening of the TCM-3D database. Embelin was shown to inhibit cell growth of prostate cancer cell lines. Embelin was also shown to overcome the protective effect of XIAP protein to cells and restore sensitivity of cells to etoposide.

I. XIAP Inhibitor Compounds

In some embodiments, the present invention provides inhibitors of XIAP anti-apoptotic activity for use in treatment of hyperproliferative disorders (e.g., cancer). In some embodiments, XIAP inhibitors include, but are not limited to, non-natural XIAP inhibitors having the general structure $W-X_n-Y_m-Z$, wherein:

W is mono- or dihydroxy-1,4-quinonyl or di- or tri-hydroxyphenyl, each optionally substituted with alkyl, aryl, heteroaryl, saturated or partially saturated carbocyclic groups, cycloalkyl, halo, arylalkyl, haloalkyl, alkoxy, alkylthio, amido, acyloxy, arylacyloxy, amino, or saturated or partially saturated heterocyclic groups;

X is $CH_2$;

Y is carbonyl;

Z is phenyl or chromen-4-on-2-yl, each optionally substituted with alkyl, aryl, heteroaryl, saturated or partially saturated carbocyclic groups, cycloalkyl, halo, arylalkyl, haloalkyl, alkoxy, alkylthio, amido, acyloxy, arylacyloxy, amino, or saturated or partially saturated heterocyclic groups, or lower alkyl;

n is 0-5; and m is 0 or 1.

In some embodiments, the XIAP inhibitors have the structure of Formula I:

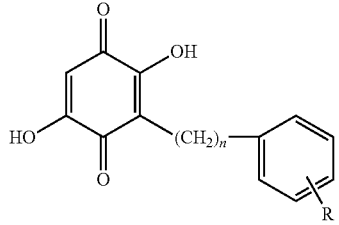

I wherein R is lower alkyl or halo and n is 0-5.

In some embodiments, the XIAP inhibitors have the structure of Formula II:

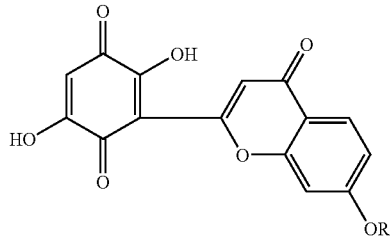

II wherein R is lower alkyl.

In some embodiments, the XIAP inhibitors have the structure of Formula III:

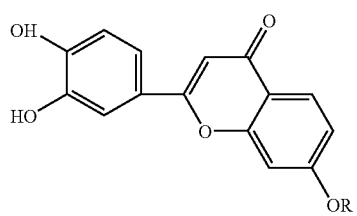

III wherein R is lower alkyl.

In some embodiments, the XIAP inhibitors have the structure of Formula IV:

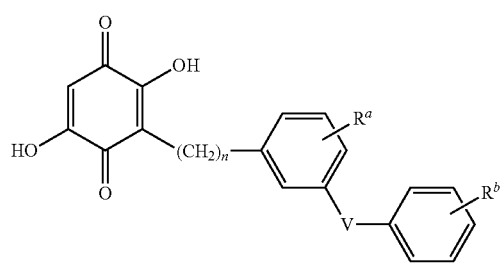

IV wherein $R^a$ and $R^b$ are each independently hydrogen, lower alkyl or halo, n is 1-5, and V is $(CH_2)_n$, CONH, or CONHCH$_2$.

In some embodiments, the inhibitor is embelin:

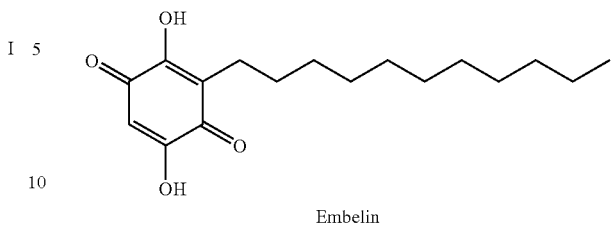

Embelin

In other embodiments, the inhibitor is an acid, enantiomer, isomer, analog, metabolite, derivative, or pharmaceutically acceptable salt of embelin.

Useful alkyl groups include straight-chained or branched $C_{1-10}$ alkyl groups, especially methyl, ethyl, propyl, isopropyl, t-butyl, sec-butyl, 3-pentyl, adamantyl, norbornyl, and 3-hexyl groups. Lower alkyl groups include straight-chained or branched $C_{1-4}$ alkyl groups.

Useful aryl groups include $C_{6-14}$ aryl, especially phenyl, naphthyl, phenanthrenyl, anthracenyl, indenyl, azulenyl, biphenyl, biphenylenyl, and fluorenyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above. Also included are the sulfoxides and sulfones of such alkylthio groups.

Useful amido groups include carbonylamido as well as any $C_{1-6}$ acyl (alkanoyl) attached to an amino nitrogen, e.g., acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g., formyloxy, acetoxy, propionoyloxy, butanoyloxy, pentanoyloxy, hexanoyloxy and the like.

Useful arylacyloxy groups include any of the aryl groups mentioned above substituted on any of the acyloxy groups mentioned above, e.g., 2,6-dichlorobenzoyloxy, 2,6-difluorobenzoyloxy and 2,6-di-(trifluoromethyl)-benzoyloxy groups.

Useful amino groups include —$NH_2$, —$NHR_1$, and —$NR_1R_2$, wherein $R_1$ and $R_2$ are $C_{1-10}$ alkyl or cycloalkyl groups as defined above.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

The present invention is not limited to the use of embelin. Experiments conducted during the course of development of the present invention using the AUTODOCK program identified interactions between embelin and XIAP BIR3 domain. The hydrophilic ring in embelin forms a hydrogen bonding network with residues Trp323, Gln319, Glu314 and Thr308 in XIAP, closely mimicking the hydrogen bonding network observed in the X-ray structure of Smac in complex with XIAP. The hydrophobic chain (its tail) of embelin interacts with Leu292 and several surrounding residues.

In further embodiments, the AUTODOCK program is used to identify new lead compounds following the general structure described above. In some embodiments, potential lead compounds are further refined using molecular dynamics (MD) simulation. Such studies have identified 3 groups of lead compounds (Formulas I-III above).

In reference to Group 1, in some embodiments, n is an integer greater than 1. In some preferred embodiments, n is an integer between 1 and 10. In some particularly preferred embodiments, n is 3, 4, or 5. In some embodiments, R is a small hydrophobic group (e.g., methyl, ethyl or propyl). In reference to Groups 2 and 3, in some embodiments, R is a hydrophobic group (e.g., $CH_3$, ethyl, propyl, isopropypl, butyl, 2-butyl, or t-butyl).

Lead compounds are screened using any suitable method, including but not limited to, those disclosed in the illustrative examples below (e.g., fluorescence polarization).

II. Therapies

In some embodiments, the present invention provides drugs that target XIAP (e.g., XIAP inhibitors and derivatives described above) for use in the treatment of hyperproliferative disorders, as well as other disorders characterized by defects in apoptosis.

The present invention provides pharmaceutical compositions which may comprise at least one XIAP inhibitor compound, and in some preferred embodiments, at least one conventional anticancer agent. The XIAP inhibitor compounds and anticancer agents may be administered in any sterile, biocompatible pharmaceutical carrier, including, but not limited to, saline, buffered saline, dextrose, and water. In some embodiments, the pharmaceutical compositions of the present invention may contain one agent (e.g., a XIAP inhibitor compound). In other embodiments, the pharmaceutical compositions contain a mixture of at least two agents (e.g., a XIAP inhibitor compound and one or more conventional anticancer agents). In still further embodiments, the pharmaceutical compositions of the present invention contain at least two agents (e.g., XIAP inhibitor compounds and one or more conventional anticancer agents) that are administered to a patient under one or more of the following conditions: at different periodicities, at different durations, at different concentrations, by different administration routes, etc. In some embodiments, the XIAP inhibitor compound is administered prior to the anticancer agent, e.g., 0.5, 1, 2, 3, 4, 5, 10, 12, or 18 hours, 1, 2, 3, 4, 5, or 6 days, 1, 2, 3, or 4 weeks prior to the administration of the anticancer agent. In some embodiments, the XIAP inhibitor compound is administered after the anticancer agent, e.g., 0.5, 1, 2, 3, 4, 5, 10, 12, or 18 hours, 1, 2, 3, 4, 5, or 6 days, 1, 2, 3, or 4 weeks after the administration of the anticancer agent. In some embodiments, the XIAP inhibitor compound and the anticancer agent are administered concurrently but on different schedules, e.g., the XIAP inhibitor compound is administered daily while the anticancer agent is administered once a week, once every two weeks, once every three weeks, or once every four weeks. In other embodiments, the XIAP inhibitor compound is administered once a week while the anticancer agent is administered daily, once a week, once every two weeks, once every three weeks, or once every four weeks.

The compositions and methods of the present invention find use in treating diseases or in altering physiological states that are characterized by the overexpression of one or more XIAP family proteins.

Depending on the condition being treated, preferred embodiments of the present pharmaceutical compositions are formulated and administered systemically or locally. Techniques for formulation and administration can be found in the latest edition of "Remington's Pharmaceutical Sciences" (Mack Publishing Co, Easton, Pa.). Exemplary pharmaceutical formulations and methods of producing pharmaceuticals are described in U.S. 20030211046A1; U.S. 20030004182A1; U.S. 2002060356384; U.S. 20020015728A1; U.S. Pat. No. 6,511,660; U.S. Pat. No. 6,406,745; U.S. Pat. No. 6,346,269; U.S. Pat. No. 6,039,977; U.S. Pat. No. 5,858,408; U.S. Pat. No. 5,631,023; U.S. Pat. No. 5,476,667; U.S. Pat. No. 5,044,091; U.S. Pat. No. 4,867,970; and WO 0028969A2. Suitable routes may, for example, include oral or transmucosal administration as well as parenteral delivery (e.g., intramuscular, subcutaneous, intramedullary, intrathecal, intraventricular, intravenous, intraperitoneal, or intranasal administration).

The compounds of the present invention may be linked to a carrier molecule to enhance the cellular uptake of the compounds. Examples of such carrier molecules include carrier peptides such as those described by Fulda et al., *Nature Med.* 8:808 (2002), Arnt et al., *J. Biol. Chem.* 277:44236 (2002), and Yang et al., *Cancer Res.* 63:831 (2003), fusogenic peptides (see, e.g., U.S. Pat. No. 5,965,404), and viruses and parts of viruses such as empty capsids and virus hemagglutinin (see, e.g., U.S. Pat. No. 5,547,932). Other carrier molecules include ligands for cell surface receptor such as asialoglycoprotein (which binds to the asialoglycoprotein receptor; see U.S. Pat. No. 5,166,320) and antibodies to cell surface receptors such as antibodies specific for T-cells, e.g., anti-CD4 antibodies (see U.S. Pat. No. 5,693,509).

The present invention contemplates administering XIAP inhibitor compounds and, in some embodiments, one or more conventional anticancer agents, in accordance with acceptable pharmaceutical delivery methods and preparation techniques. For example, XIAP inhibitor compounds and suitable anticancer agents can be administered to a subject intravenously in a pharmaceutically acceptable carrier such as physiological saline. Standard methods for intracellular delivery of pharmaceutical agents are contemplated (e.g., delivery via liposome). Such methods are well known to those of ordinary skill in the art.

In some embodiments, the formulations of the present invention are useful for parenteral administration (e.g., intravenous, subcutaneous, intramuscular, intramedullary, and intraperitoneal). Therapeutic co-administration of some contemplated anticancer agents (e.g., therapeutic polypeptides) can also be accomplished using gene therapy reagents and techniques.

In some embodiments of the present invention, XIAP inhibitor compounds are administered to a subject alone, or in combination with one or more conventional anticancer agents (e.g., nucleotide sequences, drugs, hormones, etc.) or in pharmaceutical compositions where the components are optionally mixed with excipient(s) or other pharmaceutically acceptable carriers. In preferred embodiments of the present invention, pharmaceutically acceptable carriers are biologically inert. In preferred embodiments, the pharmaceutical compositions of the present invention are formulated using pharmaceutically acceptable carriers well known in the art in dosages suitable for oral administration. Such carriers enable the pharmaceutical compositions to be formulated as tablets, pills, capsules, dragees, liquids, gels, syrups, slurries, solutions, suspensions and the like, for respective oral or nasal ingestion by a subject. In preferred embodiments, the XIAP inhibitor compounds are administered orally to a subject.

Pharmaceutical preparations for oral use can be obtained by combining the active compounds (e.g., XIAP inhibitor compounds) with solid excipients, optionally grinding the resulting mixture, and processing the mixture into granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc.; cellulose such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used. Such penetrants are known to those skilled in the art.

Pharmaceutical compositions suitable for use in the present invention include compositions wherein the active ingredients are contained in an effective amount to achieve the intended purpose. For example, an effective amount of a XIAP inhibitor compound may be that amount that induces apoptosis in a cell or tissue having elevated levels of a XIAP family protein as compared to normal nonpathological cells or tissues. The determination of an effective amount of an agent is well within the skills of those in the pharmacological arts, especially in view of the disclosure provided herein.

In addition to the active ingredients, preferred pharmaceutical compositions may contain suitable pharmaceutically acceptable carriers comprising excipients and auxiliaries that facilitate processing of the active compounds into pharmaceutically useful forms.

The pharmaceutical compositions of the present invention may be manufactured using any acceptable techniques for preparing pharmaceutical compositions including, but not limited to, by means of conventional mixing, dissolving, granulating, dragee-making, levigating, emulsifying, encapsulating, entrapping or lyophilizing processes, and the like.

Ingestible formulations of the present compositions may further include any material approved by the United States Department of Agriculture for inclusion in foodstuffs and substances that are generally recognized as safe (GRAS), such as food additives, flavorings, colorings, vitamins, minerals, and phytonutrients. The term phytonutrients, as used herein, refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations contemplated for oral administration include push-fit capsules made of gelatin, as well as soft sealed capsules of gelatin and a coating such as glycerol or sorbitol. In some embodiments, push-fit capsules can contain the active ingredients mixed with fillers or binders such as lactose or starches, lubricants such as talc or magnesium stearate, and, optionally, stabilizers. In some soft capsule embodiments, the active compounds are dissolved or suspended in a suitable liquid or solvent, such as fatty oils, liquid paraffin, or liquid polyethylene glycol, with or without stabilizers.

Pharmaceutical formulations for parenteral administration include aqueous solutions of the active compounds. Aqueous injection suspensions optionally contain substances that increase the viscosity of the suspension such as sodium carboxymethyl cellulose, sorbitol, or dextran. Additionally, suspensions of the active compounds may be prepared as appropriate oily injection suspensions. In this aspect, suitable lipophilic solvents or vehicles include fatty oils such as sesame oil, or synthetic fatty acid esters, such as ethyl oleate or triglycerides, or liposomes. Optionally, suspensions contain suitable stabilizers or agents that increase the solubility of the compounds thus allowing for the preparation of highly concentrated solutions.

Compositions comprising a compound of the invention formulated in a pharmaceutical acceptable carrier may be prepared, placed in an appropriate container, and labeled for treatment of an indicated condition. For XIAP inhibitor compounds, conditions indicated on the label may include treatment of conditions related to faulty regulation of apoptosis, hyperproliferative diseases, cancers, acquired immune deficiency syndrome (AIDS), degenerative conditions, and vascular diseases. The pharmaceutical compositions may be provided as salts and can be formed with many acids, including but not limited to hydrochloric, sulfuric, acetic, lactic, tartaric, malic, succinic, and the like. Salts tend to be more soluble in aqueous or other protonic solvents than are corresponding free base forms. In other cases, a preferred preparation comprises a lyophilized powder in 1 mM-50 mM histidine, 0.1%-2% sucrose, or 2%-7% mannitol at a pH range of from about 4.5 to 5.5, optionally combined with buffer prior to use.

In preferred embodiments, dosing and administration regimes are tailored by the clinician, or others skilled in the pharmacological arts, based upon well known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy (e.g., destruction of cancer cells) is desired, doses in excess of the average required dose are not uncommon. This approach to dosing is commonly referred to as the "maximal dose" strategy.

Additional dosing considerations relate to calculating proper target levels for the agent being administered, the agent's accumulation and potential toxicity, stimulation of resistance, lack of efficacy, and describing the range of the agent's therapeutic index.

In certain embodiments, the present invention contemplates using routine methods of titrating the agent's administration. One common strategy for the administration is to set a reasonable target level for the agent in the subject. In some preferred embodiments, agent levels are measured in the subject's plasma. Proper dose levels and frequencies are then designed to achieve the desired steady-state target level for the agent. Actual, or average, levels of the agent in the subject are monitored (e.g., hourly, daily, weekly, etc.) such that the dosing levels or frequencies can be adjusted to maintain target levels. Of course, the pharmacokinetics and pharmacodynamics (e.g., bioavailability, clearance or bioaccumulation, biodistribution, drug interactions, etc.) of the particular agent or agents being administered can potentially impact what are considered reasonable target levels and thus impact dosing levels or frequencies.

Target-level dosing methods typically rely upon establishing a reasonable therapeutic objective defined in terms of a desirable range (or therapeutic range) for the agent in the subject. In general, the lower limit of the therapeutic range is roughly equal to the concentration of the agent that provides about 50% of the maximum possible therapeutic effect. The upper limit of the therapeutic range is usually established by the agent's toxicity and not by its efficacy. The present invention contemplates that the upper limit of the therapeutic range for a particular agent will be the concentration at which less than 5 or 10% of subjects exhibit toxic side effects. In some embodiments, the upper limit of the therapeutic range is about two times, or less, than the lower limit. Those skilled in the art will understand that these dosing consideration are highly variable and to some extent individualistic (e.g., based on genetic predispositions, immunological considerations, tolerances, resistances, and the like). Thus, in some embodiments, effective target dosing levels for an agent in a particular subject may be 1, . . . 5, . . . 10, . . . 15, . . . 20, . . . 50, . . . 75, . . . 100, . . . 200, . . . X %, greater than optimal in another subject. Conversely, some subjects may suffer significant side effects and toxicity related health issues at dosing levels or frequencies far less (1, . . . 5, . . . 10, . . . 15, . . . 20, . . . 50, . . . 75, . . . 100, . . . 200, . . . X %) than those typically producing optimal therapeutic levels in some or a majority of subjects. In the absence of more specific information, target administration levels are often set in the middle of the therapeutic range.

In still further embodiments, the present invention provides methods for repetitive dosing and/or the continuous (semicontinuous) infusion of therapeutic agents (e.g., small molecule XIAP antagonists or agonists) sufficient to maintain, within a given therapeutic range, a steady-state concentration of agent(s) in a subject (e.g., in the subject's plasma). Those skilled in the art will appreciate that the compositions of the present invention can be administered such that a maintenance dose is provided. Thus, in some embodiments, the chosen agent target concentration or rate of drug delivery is adjusted to balance the rate of drug loss. Those skilled in the art of administering chemotherapeutic agents will appreciate the calculations and measurements used to ensure the balance of drug input versus drug loss to provide the desired target level of drug (or other therapeutic agent) in the subject. Particularly useful in performing these calculations are defined levels of agent clearance and availability in a particular subject.

In additional embodiments, the present invention provides intermittent dosing methods, since marked fluctuations in agent concentration between doses are generally undesirable. In situations where the absorption and distribution of the agent are balanced and spontaneous, concentration fluctuations are dictated by the agent's elimination half-life.

In embodiments where the administered compositions are relatively nontoxic, maximal dosing methods can be used, because even concentrations of the agent several times that necessary for ensuring therapeutic efficacy are well tolerated. In these embodiments, the dosing intervals are lengthened such that the concentration of the agent in the subject's system remains within the range of therapeutic effectiveness for relatively long periods of time before being cleared from the subject and additional administrations are required to bring the agent's level back into the therapeutically effective range. Thus, in certain of these embodiments, dosing intervals are longer than the agent's elimination half-life.

In other embodiments, where the compositions have relatively narrow therapeutic ranges, it may be important calculate the maximum and minimum concentrations that will occur at particular dosing interval(s). In preferred embodiments, the minimal steady-state concentration of administered agents are determined using equations, optionally corrected for the bioavailability of the agents, which are well known to those skilled in the pharmacological arts.

In still other embodiments, where the agents follow multi-exponential kinetics and the agents are administered orally, the estimation of the maximal steady-state concentration involves manipulation of several exponential constants concerning agent distribution and absorption.

The present invention also provides methods for administering loading doses of an agent, or agents, to a subject. As used herein, a "loading dose" is one or a series of doses that when given at the onset of a treatment quickly provide the target concentration of the therapeutic agent. In some embodiments, loading doses are administered to a subject having an immediate need for the target level of an agent in relation to the time required to attain a steady-state target level of the agent provided using a constant rate of administration. Various negative considerations should be weighed against the exigency of the subject's condition and her need for a loading dose prior to its administration. These considerations include, but are not limited to: 1) loading doses are often administered in one large bolus which may abruptly subject the patient to a toxic concentration of the agent; 2) agents with long half-lives will remain at levels above the target-level as compared to agents administered under lower constant rate schemes. Loading doses are often large, rapid, and given parenterally, thus dangerous side effects can potentially occur at the site of administration before the agent can obtain equilibrium in the subject's plasma.

In preferred embodiments, the clinician rationally designs an individualized dosing regimen based on known pharmacological principles and equations. In general, the clinician designs an individualized dosing regimen based on knowledge of various pharmacological and pharmacokinetic properties of the agent, including, but not limited to, F (fractional bioavailability of the dose), Cp (concentration in the plasma), CL (clearance/clearance rate), Vss (volume of drug distribution at steady state) Css (concentration at steady state), and t1/2 (drug half-life), as well as information about the agent's rate of absorption and distribution. Those skilled in the art are referred to any number of well known pharmacological texts (e.g., Goodman and Gilman's, Pharmaceutical Basis of Therapeutics, 10th ed., Hardman et al., eds., 2001) for further explanation of these variables and for complete equations illustrating the calculation of individualized dosing regimes. Those skilled in the art also will be able to anticipate potential fluctuations in these variables in individual subjects. For example, the standard deviation in the values observed for F, CL, and Vss is typically about 20%, 50%, and 30%, respectively. The practical effect of potentially widely varying parameters in individual subjects is that 95% of the time the Css achieved in a subject is between 35 and 270% that of the target level. For drugs with low therapeutic indices, this is an undesirably wide range. Those skilled in the art will appreciate, however, that once the agent's Cp (concentration in the plasma) is measured, it is possible to estimate the values of F, CL, and Vss directly. This allows the clinician to effectively fine tune a particular subject's dosing regimen.

In still other embodiments, the present invention contemplates that continuing therapeutic drug monitoring techniques be used to further adjust an individual's dosing methods and regimens. For example, in one embodiment, Css data is used is to further refine the estimates of CL/F and to subsequently adjust the individual's maintenance dosing to achieve desired agent target levels using known pharmacological principles and equations. Therapeutic drug monitoring can be conducted at practically any time during the dosing schedule. In preferred embodiments, monitoring is carried out at multiple time points during dosing and especially when administering intermittent doses. For example, drug monitoring can be conducted concomitantly, within fractions of a second, seconds, minutes, hours, days, weeks, months, etc., of administration of the agent regardless of the dosing methodology employed (e.g., intermittent dosing, loading doses, maintenance dosing, random dosing, or any other dosing method). However, those skilled in the art will appreciate that when sampling rapidly follows agent administration the changes in agent effects and dynamics may not be readily observable because changes in plasma concentration of the agent may be delayed (e.g., due to a slow rate of distribution or other pharmacodynamic factors). Accordingly, subject samples obtained shortly after agent administration may have limited or decreased value.

The primary goal of collecting biological samples from the subject during the predicted steady-state target level of administration is to modify the individual's dosing regimen based upon subsequently calculating revised estimates of the agent's CL/F ratio. However, those skilled in the art will appreciate that early postabsorptive drug concentrations do not typically reflect agent clearance. Early postabsorptive drug concentrations are dictated principally by the agent's rate of absorption, the central, rather than the steady state, volume of agent distribution, and the rate of distribution. Each of these pharmacokinetic characteristics have limited value when calculating therapeutic long-term maintenance dosing regimens.

Accordingly, in preferred embodiments, when the objective is therapeutic long-term maintenance dosing, biological samples are obtained from the subject, cells, or tissues of interest well after the previous dose has been administered, and even more preferably shortly before the next planned dose is administered.

In still other embodiments, where the therapeutic agent is nearly completely cleared by the subject in the interval between doses, then the present invention contemplates collecting biological samples from the subject at various time points following the previous administration, and most preferably shortly after the dose was administered.

In yet other embodiments, when low clearance of the agent is problematic, and toxicity issues are likely to result from its accumulation, the present invention contemplates measuring agent concentrations immediately before the administration of the subsequent dose. In these embodiments, the determination of maximal and minimal agent concentrations are preferred.

The methods of the present invention further contemplate that when a constant maintenance dosage is administered, steady state is reached only after expiration of four agent half-lives. Samples collected too soon after dosing begins do not accurately reflect agent clearance. However, for potentially highly toxic agents, significant toxicity and damage may already have ensued before expiration of the agent's fourth half-life. Thus, in some instances when it is important to maintain control over agent concentrations, a first sample is taken after two half-lives, assuming a loading dose has not been administered. If agent concentration already exceeds 90% of the eventual expected mean steady-state concentration, the dosage rate is halved, and another sample obtained following an additional two half-lives. The dosage is halved again if this sample once more exceeds the target level. If the first concentration does not exceed tolerable limits, subsequent administrations are given at the initial dose rate. If the concentration is lower than expected, the steady state can likely be achieved in about two half-lives, and at this point the dosage rate can be adjusted as described herein.

In embodiments comprising intermittent dosages, an additional concern related to timing of collection of concentration information, is if the sample was obtained immediately before the next scheduled dose, concentration will be at a minimal value, not the mean; however, as discussed herein, the estimated mean concentration can be calculated using equations known in the pharmacological arts.

When administering therapeutic agents having first-order kinetics, the average, minimum, and maximum concentrations at steady state are linearly related to the dose and dosing rate. Thus, in these embodiments, the ratio between the measured and the desired agent concentrations is used to adjust dosing.

In another aspect of the present invention, computer programs are helpful in designing dosing regimens. Typically, these programs take into account the measured drug concentrations and various factors (e.g., measured or predicted) related to the individual subjects.

The present invention is not limited to any particular temporal constraints on collecting subject, tissue, cell culture, or animal drug administration data or samples. Moreover, the present invention is not limited to collecting any particular type of samples (e.g., biological samples) from a subject, tissue, cell culture, or test animal laboratory animal or otherwise. Indeed, in some embodiments, the present invention contemplates acquiring biological samples including, but not limited to, polynucleotides, polypeptides, lipids, carbohydrates, glycolipids, ionic species, metabolites, inorganic molecules, macromolecules and macromolecular precursors as well as cell fractions, blood (e.g., cellular and soluble or insoluble blood components including, but not limited to, plasma, serum, metabolites, factors, enzymes, hormones, and organic or inorganic molecules), exudates, secretions, sputum, excreta, cell and tissue biopsies, CNS fluids (cerebrospinal fluid), secretions of lachrymal, salivary, and other glands, seminal fluids, etc., and combinations of these or any other subcellular, cellular, tissular, organismal, systemic, or organismic biological materials. Biological samples taken from a subject can be analyzed for chemical or biochemical changes (e.g., changes in gene expression) or other effects resultant from administration of the therapeutic agent. Further biological sample and sampling consideration are described below.

In some of these embodiments, the biological and pharmacological effects of the therapeutic compositions are determined using routine laboratory procedures on the collected samples including, but not limited to, microscopy (e.g., light, fluorescence (confocal fluorescence, immunofluorescence), phase-contrast, differential interference-contrast, dark field, or electron (transmission, scanning, cryo-), NMR, autoradiography), cell sorting techniques (e.g., fluorescence-activated), chromatography techniques (e.g., gel-filtration, ion exchange, hydrophobic, affinity, HPLC), electrophoretic techniques (e.g., SDS-PAGE, 2D-, 3D-, isoelectric focusing), ultracentrifugation, immunocytochemical and immunohistochemical technologies (e.g., ELISA, Western blotting, Immuno blotting), nucleic acid, including recombinant, technologies (e.g., PCR (inverse, reverse, nested), Northern blotting, Southern blotting, Southwestern blotting, in situ hybridization, FISH, nick-translation, DNAse footprinting, DNAse hypersensitivity site mapping, Maxam-Gilbert sequencing, Sanger sequencing, gel-shift (mobility shift) analysis, S1 nuclease analysis, RNAse protection assay, CAT assays, transgenic techniques, knock-out techniques, and reporter gene systems), amino acid analysis (e.g., Edman degradation), morphological, pathological, or phenotypical observations, and other observations with or without aid of instrumentation.

In some embodiments, subjects are questioned directly or indirectly regarding their state of health and any changes attributable to the administration of the therapeutic compositions (e.g., drugs, small molecules, and other therapeutic agents and techniques) and methods of the present invention.

Various interpatient and intrapatient pharmacokinetic considerations affect the design of dosing and administration regimens for individual patients. For any given drug, there may be wide variations in its pharmacokinetic properties in a particular subject, and up to one-half or more of the total variation in eventual response. The importance of these variable factors depends in part upon the agent and its usual route of elimination. For example, agents that are primarily removed by the kidneys and excreted unchanged into the urinary system, tend to show less interpatient variability in subjects with similar renal function than agents that are metabolically inactivated. Agents that are extensively metabolized, and agents that have high metabolic clearance and large first-pass elimination rates show large differences in interpatient bioavailability. Agents with slower rates of biotransformation typically have the largest variation in elimination rates among individual subjects. Differences in subject genotypes also plays an important part in determining different metabolic rates. Pathological and physiological variations in individual subjects' organ functions (e.g., renal or hepatic diseases) are major factors that can affect an agent's rate of disposition. Kidney or liver diseases often impair drug disposition and thus increase interpatient drug variability. Other factors (e.g., age) can also affect the responsiveness of targeted cells and tissues (e.g., the brain) to a particular composition or method of the present invention, and can alter the expected range of the therapeutic target level for the agent.

When invasive patient samples (e.g., blood, serum, plasma, tissues, etc.) are necessary to determine the concentration of the therapeutic agent(s) in a subject, design of the collection procedures should be undertaken after considering various criteria including, but not limited to: 1) whether a relationship exists between the concentration of the agent and any desired therapeutic effects or avoidable toxic effects; 2) whether these is substantial interpatient variability, but small intrapatient variation in agent disposition; 3) whether it is otherwise difficult or impractical to monitor the effects of the agent; and 4) whether the therapeutic concentration of the agent is close to the toxic concentration. In still other embodiments, concentration measurements are supplemented with additional measurements of pharmacokinetic, pharmacodynamic, or pharmacological effects.

In some instances, considerable interpatient response variations exist after the concentration of agent has been adjusted to the target level. For some agents, this pharmacodynamic variability accounts for much of the total variation in subject response. In some embodiments, the relationship among the concentration of an agent and the magnitude of the observed response may be complex, even when responses are measured in simplified systems in vitro, although typically a sigmoidal concentration-effect curve is seen. Often there is no single characteristic relationship between agent concentration (e.g., in the subject's plasma) and measured effect. In some embodiments, the concentration-effect curve may be concave upward. In other embodiments, the curve is concave downward. In still other embodiments, the data plots are linear, sigmoid, or in an inverted U-shape. Moreover, the resulting concentration-effect relationship curves can be distorted if the response being measured is a composite of several effects. In some preferred embodiments, the composite concentration-effect curves are resolved into simpler component curves using calculations and techniques available to those skilled in the art.

The simplified concentration-effect relationships, regardless of their exact shape, can be viewed as having four characteristic variables: potency, slope, maximal efficacy, and individual variation. Those skilled in the art will appreciate that the potency of an agent is measured by the intersection of the concentration-effect curve with the concentration axis. Although potency is often expressed as the dose of an agent required to produce the desired effect, it is more appropriately expressed as relating to the concentration of the agent in the subject (e.g., in plasma) that most closely approximates the desired situation in an in vitro system to avoid complicating pharmacokinetic variables. Although potency affects agent dosing, knowledge of an agent's potency alone is relatively unimportant in clinical use so long as a dose sufficient to obtain the target level can be conveniently administered to the subject. It is generally accepted that more potent agents are not necessarily therapeutically superior to less potent agents. One exception to this principle, however, is in the field of transdermal agents.

The maximum effect that an agent can induce in a subject is called its maximal or clinical efficacy. An agent's maximal efficacy is typically determined by the properties of the agent and its receptor-effector system and is reflected in the plateau of the concentration-effect curve. In clinical use, however, an agent's dosage may be limited by undesirable effects (e.g., toxicity), and the true maximal efficacy of the agent may not be practically achievable without harming the subject.

The slope and shape of the concentration-effect curve reflects the agent's mechanism of action, including the shape of the curve that, at least in part, describes binding to the agent's receptor. The rise of the concentration-effect curve indicates the clinically useful dosage range of the agent. Those skilled in the art will appreciate that the dosage ranges recited herein are approximations based on sound pharmacological principles and that actual responses will vary among different individuals given the same concentration of an agent, and will even vary in particular individuals over time. It is well known that concentration-effect curves are either based on an average response, or are tailored to reflect an actual response in a particular individual at a particular time.

The concentration of an agent that produces a specified effect in a particular subject is called the individual effective concentration. Individual effective concentrations usually show a lognormal distribution, resulting in a normal variation curve from plotting the logarithms of the concentration against the frequency of achieving the desired effect. A cumulative frequency distribution of individuals achieving the desired effect as a function of agent concentration is called the concentration-percent curve or quantal concentration-effect curve. The shape of this curve is typically sigmoidal. The slope of the concentration-percent curve is an expression of the pharmacodynamic variability in the population rather than an expression of the concentration range from a threshold to a maximal effect in the individual patient.

Those skilled in the art will appreciate that the median effective dose ($ED_{50}$) is the dose of an agent sufficient to produce the desired effect in 50% of the population.

In preclinical drug studies, the dose (MTD) is determined in experimental animals. The ratio of the MTD to the $ED_{50}$ is an indication of the agent's therapeutic index and is a measurement of the selectivity of the agent in producing its desired effects. In clinical studies, the dose, or preferably the concentration, of an agent sufficient to produce toxic effects is compared to the concentration required for the therapeutic effects in the population to provide a clinical therapeutic index. However, due to individual pharmacodynamic variations in the population, the concentration or dose of an agent required to produce the therapeutic effect in most subjects occasionally overlaps the concentration that produces toxicity in some subjects despite the agent having a large therapeutic index. Those skilled in the art will appreciate that few therapeutic agents produce a single effect, thus, depending on the effect being measured, the therapeutic index for the agent may vary.

Preferred embodiments of the present invention provide approaches to individualize dosing levels and regimens. In preferred embodiments, optimal treatment regimens for particular subjects are designed after considering a variety of biological and pharmacological factors including, but not limited to, potential sources of variation in subject response to the administered agent(s), diagnosis specifics (e.g., severity and stage of disease, presence of concurrent diseases, etc.), other prescription and non prescription medications being taken, predefined efficacy goals, acceptable toxicity limits, cost-benefit analyses of treatment versus non treatment or treatment with other various available agents, likelihood of subject compliance, possible medication errors, rate and extent of agent absorption, the subject's body size and compositions, the agent's distribution, the agent's pharmacokinetic profile (e.g., physiological variables, pathological variables, genetic factors and predispositions, drug interactions, potential drug resistances, predicted rate of clearance), potential drug-receptor interactions, functional state, and placebo effects.

In preferred embodiments, the clinician selects an appropriate marker for measuring the ultimate effectiveness of the administered agent(s) in the subject. The present invention contemplates that in some embodiments, appropriate markers of an agent's effectiveness include a decrease (or increase) in some measurable biological state, condition, or chemical level (e.g., toxin load, viral titer, antigen load, temperature, inflammation, blood cell counts, antibodies, tumor morphology, and the like). A large number of diagnostic procedures and tests are available for gathering information on various markers including, but not limited to, cell culture assays (e.g., invasion assays in soft-agar and the like), radiographic examination (e.g., chest X-ray), computed tomography, computerized tomography, or computerized axial tomography (CAT) scans, positron emission tomography (PET) scans, magnetic resonance imaging (MRI or NMRI), mammography, ultrasonography (transvaginal, transcolorectal), scintimammography (e.g., technetium 99m sestamibi, technetium-99m tetrofosmin), aspiration (e.g., endometrial), palpation, PAP tests (e.g., smears), sigmoidoscopy (e.g., flexible fiberoptic), fecal occult blood testing (e.g., Guaiac-based FOBT), digital rectal examination, colonoscopy, virtual colonoscopy (also known as colonography), barium enema, stool analysis (See e.g., K. W. Kinzler and B. Vogelstein, Cell, 87(2):159-70 (1996); S. M. Dong et al., J. Natl. Cancer Inst., 93(11):858-865 (2001); G. Traverso et al., N. Engl. J. Med., 346(5):311-20 (2002), G. Traverso et al., Lancet, 359(9304):403 (2002); and D. A. Ahlquist et al., Gastroenterology, 119(5):1219-1227, (2000)), serum prostate-specific antigen (PSA) screening, endoscopy, gallium scans, marrow and tissue biopsies (e.g., core-needle, percutaneous needle biopsy, thoracotomy, endometrial, etc.) and histological examinations, direct and/or indirect clinical observations (e.g., patient surveys, inquiries, or questionnaires), cytological sampling and collection of biological tissues, fluids, and markers therein, (e.g., blood, urine (e.g., hematuria screening, urinary cytologic examinations), sputum (e.g., sputum cytology), feces, CNS fluids (e.g., LPs, spinal taps), blood products, including proteins and peptides (e.g., XIAP family proteins), cancer markers (e.g., CA 125 (ovarian cancer), CA 15-3 (breast cancer), CEA (ovarian, lung, breast, pancreas, and gastrointestinal tract cancers), PSA (prostate cancer), p53 gene product, MIC2 gene product), metabolites (e.g., vanillylmandelic acid (VMA), and homovanillic acid (HVA)), antigens (e.g., serum alpha-fetoprotein (AFP)), salts, minerals, vitamins, soluble factors, insoluble factors, nucleic acids, and the like).

For any compound used in the methods of the invention, the therapeutically effective dose can be estimated initially from the concentration of compounds that causes fifty percent cell growth inhibition and/or cell killing in the cell culture assays. Subsequently, dosages can be formulated in animal models (e.g., murine models) to achieve a desirable circulating concentration (target-level) range that induces the desired effect (e.g., apoptosis) in target cells characterized by elevated expression levels of XIAP family proteins. A therapeutically effective dose is the amount of XIAP inhibitor compound (and in some embodiments, and additional therapeutic agents (e.g., chemotherapeutic and/or anti-neoplastic agents) sufficient to ameliorate (or prevent) the symptoms of a disease or pathology (e.g., unregulated cell proliferation, growth, invasion, autoimmunity).

In preferred embodiments, the toxicity and therapeutic efficacy of agents is determined using standard pharmaceutical procedures in cell cultures or experimental animals, e.g., for determining the MTD and the $ED_{50}$. Agents that exhibit large therapeutic indices are preferred. The data obtained from cell culture assays or animal models can be used to formulate dosing ranges in, for example, mammals (e.g., humans, *Equus caballus*, *Felis catus*, and *Canis familiaris*, etc.). Preferable dosing concentrations are near the calculated or observed $ED_{50}$ value for an agent. More preferable dosing concentrations are near an agent's $ED_{50}$ value and cause little or no toxicity. Any given dosage may vary within, exceed, or be less than, the therapeutic index for any particular agent, depending upon the formulation, sensitivity of the patient, and the route of administration.

In some embodiments, from 1, 2, 3, 4, 5, . . . 10, . . . 20, . . . 35, . . . 55, . . . 100, . . . 1,000, . . . 10,000, or more, units of time (e.g., minutes, hours, days, weeks, etc.) pass between the first administration of a therapeutic agent and subsequent administration. In some of these embodiments, the interval(s) between any two or more administration points are constant (e.g., of equal duration). In still other embodiments, the interval(s) between any two or more administration points are varied (e.g., not of equal duration). Varied intervals can be either random or repeating and formulaic. Those skilled in the art will appreciate the steps necessary for designing and adjusting the dosing schedules and/or the dosing order of any one or more agents.

Accordingly, preferred methods of the present invention are not limited to providing any particular order or sequence for administering the XIAP inhibitor compounds and non-XIAP inhibitor additional therapeutic agents to a subject or to in vitro/ex vivo cells, tissues, or organs. For example, in some embodiments, a XIAP inhibitor compound is administered to a subject or to in vitro cells, tissues, or organs, followed by one or more additional agents.

The present invention provides the following exemplary formulas to illustrate the flexibility available to the skilled clinician when designing dosing regimens comprising one or more XIAP inhibitor compound and optionally one or more non-XIAP inhibitor compound (e.g., conventional anticancer drug), therapy (e.g., radiotherapy), or technique (e.g., surgical intervention). Thus, each variable represents the subjection of the patient or in vitro cells, tissues, or organs of interest to a therapeutic event (e.g., the administration of a XIAP inhibitor compound). It is understood that the exemplary formulas represent a portion of the total possible formulaic combinations and permutations of the particular variables used in this exemplary. It is further understood, one skilled in the art could complete the exemplary listing of formulas to recite every possible permutation of the recited variables. It is also understood that any implied time intervals between adjacent variables can represent simultaneous therapeutic events, or the elapse of milliseconds, seconds, minutes, hours, days, weeks, months, or years. G1=a first administration of a XIAP inhibitor compound; G2=a second administration of a XIAP inhibitor compound, G3=a third administration of a XIAP inhibitor compound; Gn=a fourth administration of a XIAP inhibitor compound; NGC1=a first administration of a non-XIAP inhibitor compound, therapy, or technique; NGC2=a second administration of a non-XIAP inhibitor compound, therapy, or technique; NGC3=a third administration of a non-XIAP inhibitor compound, therapy, or technique; and NGCn=a fourth administration of a non-XIAP inhibitor compound, therapy, or technique, such that the following exemplary administration regimens are possible: (G1); (G1, G2); (G1, G2, G3); (G1, G2, G3, Gn); (G1, NGC1, G1, NGC1, NGC2); (G1, NGC1, NGC2, NGC3); (G1, NGC1, NGC2, NGC3, NGCn); (G1, G2, NGC1); (G1, G2, NGC1, NGC2); (G1, G2, NGC1, NGC2, NGC3); (G1, G2, NGC1, NGC2, NGC3, NGCn); (G1, G2, G3, NGC1); (G1, G2, G3, NGC1, NGC2); (G1, G2, G3, NGC1, NGC2, NGC3); (G1, G2, G3, NGC1, NGC2, NGC3, NGCn); (G1, G2, G3, Gn, NGC1); (G1, G2, G3, Gn, NGC1, NGC2); (G1, G2, G3, Gn, NGC1, NGC2, NGC3); (G1, G2, G3, Gn, NGC1, NGC2, NGC3, NGCn); (NGC1, G1); (NGC1, G1, G2); (NGC1, G1, G2, G3); (NGC1, G1, G2, G3, Gn); (NGC1, NGC2, G1); (NGC1, NGC2, G1, G2); (NGC1, NGC2, G1, G2, G3); (NGC1, NGC2, G1, G2, G3, Gn); (NGC1, NGC2, NGC3, G1); (NGC1, NGC2, NGC3, G1, G2); (NGC1, NGC2, NGC3, G1, G2); (NGC1, NGC2, NGC3, G1, G2, G3); (NGC1, NGC2, NGC3, G1, G2, G3, Gn); (NGC1, NGC2, NGC3, NGCn, G1); (NGC1, NGC2, NGC3, NGCn, G1, G2); (NGC1, NGC2, NGC3, NGCn, G1, G2, G3); (NGC1, NGC2, NGC3, NGCn, G1, G2, G3, Gn); (G1, NGC1, G2); (G1, NGC1, G2, G3); (G1, NGC1, G2, G3, Gn); (G1, G2, NGC1, G3); (G1, G2, NGC1, G3, Gn); (G1, G2, G3, NGC1, Gn); (NGC1, G1, NGC2); (NGC1, G1, NGC2, NGC3); (NGC1, G1, NGC2, NGC3, NGCn); (NGC1, NGC2, G1, NGC3); (NGC1, NGC2, NGC3, G1, NGCn); (G1, NGC1, NGC2, G2); (G1, NGC1, NGC2, G2, G3); (G1, NGC1, NGC2, G2, G3, Gn); (G1, NGC1, NGC2, NGC3, G2); (G1, NGC1, NGC2, NGC3, G2, G3); (G1, NGC1, NGC2, NGC3, G2, G3, Gn); (G1, NGC1, NGC2, NGC3, NGCn, G2); (G1, NGC1, NGC2, NGC3, NGCn, G2, G3); (G1, NGC1, NGC2, NGC3, NGCn, G2, G3, Gn); (G1, NGC1, G2, NGC2); and (G1, NGC1, G2, NGC2, G3); (G1, NGC1, G2, NGC2, G3, Gn).

In some embodiments, from 1, 2, 3, 4, 5, . . . 10, . . . 20, . . . 35, . . . 55, . . . 100, . . . 1,000, . . . 10,000, or more, administrations of an agent (or agents) are required to produce the desired effect (e.g., amelioration of a disease such as a neoplastic disease) in a subject or in in vitro cells, tissues, or organs of interest. The methods of the present invention are not limited to the administration of any particular XIAP inhibitor compound, and optionally any one or more additional therapeutic agents, surgical interventions, or radiotherapies. In some embodiments, at least one XIAP inhibitor compound is administered to a subject substantially simultaneously with at least one additional therapeutic agent, surgical intervention, or radiotherapy.

The present invention is not limited to any particular pharmaceutical formulations. Indeed, in some contemplated pharmaceutical compositions and methods, a XIAP inhibitor compound is formulated (e.g., in suspension) with a non-XIAP inhibitor therapeutic agent. In other pharmaceutical compositions and methods, a multitude of XIAP inhibitor compounds (e.g., 2 or more) and optionally a multitude of non-XIAP inhibitor therapeutic agents (e.g., 2 or more) are formulated in any combination thereof. Accordingly, the present invention is not limited to any particular formulations for combining two or more XIAP inhibitor compounds and/or two or more non-XIAP inhibitor therapeutic agents. However, as described herein, and as routinely known in the chemical, biological, and pharmacological arts, certain XIAP inhibitor compounds and non-XIAP inhibitor therapeutic agents are preferentially combined or segregated. Certain pharmaceutical compositions optionally comprise stabilizers, preservatives, adjuvants, pH modifiers, bioavailability modifiers, additives, excipients, diluents, lubricants, anti-oxidants, disintegrating agents, binders, thickening agents, emulsifiers, surfactants, sweeteners, pigments, flavorings, perfuming agents and the like, to improve various biological, chemical, or pharmaceutical characteristics.

Normal dosage amounts may vary from about 0.001 to 100 mg, up to a total dose of about 1 g, depending upon the route of administration. Guidance as to particular dosages and methods of delivery are provided in the literature (See e.g., U.S. Pat. Nos. 4,657,760; 5,206,344; and 5,225,212, U.S. Pat. No. 6,041,788, U.S. Pat. No. 6,273,727, U.S. Pat. No. 6,558,957, U.S. 20030017459A1, U.S. Pat. No. 5,782,799, U.S. Pat. No. 6,056,734, U.S. Pat. No. 6,528,086, U.S. 20020065483A1, WO 0168169A1, and WO02072178A1).

Administration of some agents to a patient's bone marrow may necessitate delivery in a manner different from intravenous injections.

In some embodiments, the XIAP inhibitor compounds are administered at a dosage range of about 1 to 1,000 mg/day, preferably about 1 to 200 mg/day, more preferably from about 10 to 80 mg/day, and most preferably from about 30 to 40 mg/day. In some preferred embodiments, the XIAP inhibitor compounds are administered (e.g., orally) in a tolerable daily dose (e.g., 30 to 40 mg/day) shown to have some biologic activity (e.g., alterations in Bcl proteins, angiogenesis proteins, cell cycle alteration, apoptosis markers, or alterations in Rb and Cyclin D1 levels). In a further embodiment, the XIAP inhibitor compounds are administered at a dosage range of about 40 to about 500 mg/week).

In other embodiments, the effective dose of the XIAP inhibitor compounds will typically be in the range of about 0.01 to about 50 mg/kg, preferably about 0.1 to about 10 mg/kg of mammalian body weight, administered in single or multiple doses. Generally, the compositions may be administered to subjects in need of such treatment in a daily dose range of about 1 to about 2,000 mg per subject.

Preferred embodiments of the present invention provide pharmaceutical compositions and methods for administering an effective amount of a XIAP inhibitor compound (and optionally one or more non-XIAP inhibitor therapeutic agents, such as conventional anticancer drugs) to a subject to inhibit cell (e.g., cancer cell) proliferation. In some other preferred embodiments, the present invention further provides pharmaceutical compositions and methods of coadministering an effective amount of at least one conventional anticancer agent in addition to XIAP inhibitor to a patient, such that cell (e.g., cancer cell) proliferation is inhibited.

In preferred embodiments, the subject has a disease characterized by the overexpression of a XIAP family protein. In some embodiments, diseases characterized by overexpression of a XIAP family protein include, but are not limited to, hyperproliferative diseases, cancers, acquired immune deficiency syndrome (AIDS), degenerative conditions, and vascular diseases.

In other embodiments, the subject has an autoimmune/inflammatory disorder. Examples include, but are not limited to, Crohn's disease, psoriasis, chronic obstructive pulmonary disease, inflammatory bowel disease, multiple sclerosis, and asthma.

In still further embodiments, neoplastic diseases (e.g., cancers) suitable for treatment (and optionally prevention) by the present compositions and methods include, but are not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. However, the present invention is not intended to be limited to treating (and optionally preventing) any particular type of cancer.

In some embodiments, diseases suspected of being characterized by having elevated levels of XIAP family protein(s) suitable for treatment (and optionally prevention) by the present invention are selected by obtaining a sample of interest (e.g., cells, tissues, fluids, etc.) suspected of having high levels of XIAP family proteins (e.g., XIAP, Bcl-$X_L$, Mcl-1, A1/BFL-1, and BOO-DIVA, etc.), measuring the levels of XIAP family proteins in the sample using one or more well established immunohistochemical techniques (e.g., ELISA and Western blots, etc.), and comparing the levels of XIAP family proteins in the sample with levels of XIAP family proteins in relevant reference nonpathological samples. In other embodiments, diseases suspected of being characterized by having elevated levels of one or more XIAP family proteins (e.g., XIAP, Bcl-$X_L$, Mcl-1, A1/BFL-1, and BOO-DIVA, etc.) are selected by comparing levels of one or more markers (e.g., polynucleotides, polypeptides, lipids, etc.) in a sample (e.g., cells, tissues, fluids, etc.) that directly or indirectly indicate elevated levels of XIAP family proteins in the sample as compared to levels of these markers in relevant nonpathological samples. In still further embodiments, diseases suspected of being characterized by having elevated levels of XIAP family proteins (e.g., XIAP, BC1-$X_L$, Mcl-1, A1/BFL-1, and BOO-DIVA, etc.) are selected from diseases that do not respond or that stop responding to treatment with one or more conventional anticancer therapies (e.g., chemotherapy, radiation therapy, and/or surgical intervention).

The present invention is not intended to be limited to the administration routes chosen for delivering agents to a subject. Indeed, a number of suitable administration routes are contemplated, the selection of which is within the skill of those in the art.

In still other preferred embodiments taxanes (e.g., docetaxel) are administered to a patient in combination with XIAP inhibitor compounds. The classic docetaxel dosing schedule is 60-100 mg/m$^2$ every 3 weeks. However, recent studies suggest that taxanes can be given safely, with perhaps higher dose intensity, on a weekly schedule. (See e.g., J. D. Hainsworth et al., J. Clin. Oncology, 16:2164-2168 (1998); J. D. Hainsworth et al., J. Clin. Oncology, 19:3500-3505 (2001); and C. Kouroussis et al., Cancer Chemo. Pharm., 46:488-492 (2000)). The patient toxicities associated with administering taxanes include neutropenia, asthenia, alopecia, hypersensitivity reactions, skin toxicity, and edema. Preferred embodiments of the present invention provide weekly administrations of taxanes to reduce patient toxicities while preserving agent efficacy. In other embodiments, administration of taxanes (e.g., docetaxel) more frequently than once a week during a patient's course of treatment with the disclosed XIAP inhibitor compounds is expected to produce synergistic effects.

The following example provides a description of an exemplary testing procedure used to determine potential drug interactions between XIAP inhibitor compounds and one or more anticancer agents that are candidates for co-administration with XIAP inhibitor.

Docetaxel is extensively metabolized by CYP3A4, a specific cytochrome p450 enzyme. Pharmacokinetic data obtained for docetaxel indicates wide variance in its clearance between patients. Poor docetaxel clearance may result in an increase in the area-under-the-curve (AUC) and thus greater patient toxicity. Several investigations have reported that XIAP inhibitor decreases cytochrome P-450 and mixed-function oxidases, although these results have been challenged, and no human studies have been performed which specifically address this issue. Thus, it is possible that XIAP inhibitor could inhibit CYP3A4 activity and lead to toxic docetaxel accumulation in some patients.

In one embodiment, the patient is administered a daily dose of a XIAP inhibitor compound for 1 week prior to receiving their first dose of docetaxel. The pharmacokinetic profile of docetaxel in the patient's system is evaluated after the patient receives their first dose of docetaxel. (See, R. Bruno et al., J. Clin. Oncol., 16:187-196 (1998)). Docetaxel dosing is started at a reduced dose of about 15 mg/m$^2$/week. The dose of docetaxel is gradually escalated to a maximally tolerated dose of about 35 mg/m$^2$/week. Simultaneously, information will be collected on effects of XIAP inhibitor administration on the phenotypic expression of CYP3A4. The phenotypic expression of CYP3A4 is measured easily and reproducibly using an erythromycin breath test (ERMBT). (See, e.g., P. Watkins, Pharmacogenetics, 4:171-184 (1994); and J. Hirth et al., Clin. Cancer Res., 6:1255-1258 (2000)). The ERMBT test has been shown to predict steady state trough blood levels of drugs that are CYP3A4 substrates. Consequently, some embodiments of the present invention are directed to the co-administration of XIAP inhibitor compounds and taxanes (e.g., docetaxel) using an ERMBT to determine potential drug interactions. Those skilled in the art will appreciate that similar testing methodologies can be utilized to determine potential interactions between XIAP inhibitor compounds and additional candidate compounds for co-administration.

In some embodiments, standard immunohistochemical techniques are used to analyze patient samples before, during, or after treatment with the methods and compositions of the present invention. In some of these embodiments, the immunohistochemical techniques are used to quantify changes in the levels of XIAP family proteins (e.g., XIAP, Bcl-X$_L$, and Bax, etc.). For example, in some embodiments, antibodies to XIAP (DAKO, Carpinteria, Calif.), Bcl-X$_L$, and/or Bax (Zymed, South San Francisco, Calif.) are used to determine levels of these XIAP proteins in a patient sample. In preferred embodiments, results from the immunohistochemical studies are interpreted using well-established criteria known to those in the art, wherein any cytoplasmic or nuclear staining are considered positive. The expression levels of XIAP, Bcl-X$_L$, and Bax can be determined by counting at least 1,000 neoplastic cells in each case and expressed as a percentage. Expression will be considered high when the percentage of positive cells is >25% for XIAP, and BC1-X$_L$, and >50% for Bax. (See e.g., G. Rassidakis et al., Amer. J. Path., 159:527-535 (2001); and S. Shi et al., J. Histochem. Cytochem., 39:741-748 (1991)). In other embodiments, intermittent sampling of whole blood is conducted. Samples are subsequently prepared for fluorescence activated cell sorting (FACS) analysis of XIAP and Bcl-X$_L$ expression in peripheral blood lymphocytes (PBLs) and for immunomagnetic selection of circulating epithelial cells.

In some embodiments, the primary endpoint of dosing studies occurs when the maximum tolerated dose of a XIAP inhibitor compound (at a particular daily dose, e.g., 30 mg/day), optionally co-administered with a anticancer drug, is established. In some embodiments, dose-limiting toxicity (DLT) is established when a given sample (e.g., a cell, tissue, or fluid sample) exhibits >500 neutrophils per given unit, or upon observing any Grade 3 or 4 toxicities while the patient is being studied.

In still some other embodiments, to evaluate dose escalation a minimum of 9 weeks of treatment is required for 2 or more patients at each dose level. The maximum tolerated dose (MTD) is defined as the dose at which 33% of patients experience DLT. In preferred embodiments, doses are allocated to patients according to the criteria described in the Continual Reassessment Method (J. O'Quigley et al., Biometrics 46:33-48 (1990)) called Tine-to-Event CRM or (TITE-CRM). Briefly, the TITE-CRM method provides a model for the time to occurrence of toxic response as a function of dose, and allows information from all patients enrolled in a trial to be used when allocating new patient dose levels. Because this method is very flexible in terms of the number of patients treated at each dose, subjects may be continuously recruited throughout a trial, without recruitment pauses, as long as patients are treated at a dose consistent with the safety profile.

In preferred embodiments, diseased cells and tissues are subjected to assays for cell viability and signs of induction of apoptosis (e.g., morphological changes, DNA integrity, mitochondria pathways, alterations of expression of XIAP family proteins, and caspase activation as well as upstream and downstream effectors of caspases and caspase inhibitors). Those skilled in the art will be able to readily design and execute assays to test these and other cellular and biochemical parameters in treated cells and tissues.

III. Combination Therapies

It is contemplated that administration of at least one XIAP inhibitor or related compound sensitizes cancer cells having high levels of expression of XIAP, which are resistant to conventional anticancer therapies (e.g., apoptosis inducing cancer therapies), to treatment with additional anticancer agents (e.g., docetaxel or etoposide). The present invention is, however, not limited to the administration of any particular combination of XIAP inhibitor compounds and anticancer therapeutic agents, nor is the invention limited to any particular sequence or level of agents being administered.

In one embodiment of the present invention, the co-administration of a XIAP inhibitor compound and one or more anticancer agents produces a synergistic effect, i.e., an effect that is more than the additive effect of each compound administered individually. In a further embodiment of the present invention, the co-administration of an XIAP inhibitor compound and one or more anticancer agents allows lower doses of the XIAP inhibitor compound and/or the one or more anticancer agents to be used. The ability to achieve efficacy using lower doses allows the administration of doses that do not induce any substantial toxicity in the subject. In another embodiment of the present invention, the co-administration of an XIAP inhibitor compound and one or more anticancer agents may lead to complete regression of a tumor whereas either compound alone would provide only a partial regression. In a further embodiment of the present invention, the administration of an XIAP inhibitor compound sensitizes neoplastic cells to the therapeutic effect of anticancer agents. Thus, a lower dose of the anticancer agent is sufficient to kill the neoplastic cells when co-administered with a XIAP inhibitor compound.

Examples of lower dose ranges of XIAP inhibitor compounds and some anticancer agents that can be used in combination with XIAP inhibitor compounds for the treatment of particular cancers are presented in Table 1-3 below. These examples are not intended to limit the present invention in any way.

TABLE 1

| | XIAP inhibitor | Cisplatin | Docetaxel | Radiation |
|---|---|---|---|---|
| Breast Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-30 mg/m$^2$ every wk; 5, 10, 15, 20, 25, 30 mg/m$^2$ every wk; 5-120 mg/m$^2$ every 3 wk; 5, 10, 15, 20, 25, 30, 35, 40, 45, 50, 55, 60, 65, 70, 75, 80, 85, 90, 95, 100, 105, 110, 115, 120 mg/m$^2$ every 3 wk | 10-40 mg/m$^2$ every wk; 10, 15, 20, 25, 30, 35, 40 mg/m$^2$ every wk; 10-60 mg/m$^2$ every 2 wk; 10, 15, 20, 25, 30, 35, 40, 45, 50, 55, 60 mg/m$^2$ every 2 wk; 20-100 mg/m$^2$ every 3 wk; 20, 25, 30, 35, 40, 45, 50, 55, 60, 65, 70, 75, 80, 85, 90, 95, 100 mg/m$^2$ every 3 wk | 2-65 Gy total dose; 2, 5, 10, 15, 20, 25, 30, 35, 40, 45, 50, 55, 60, 65 Gy total dose |
| Prostate Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-20 mg/m$^2$/d for 3 d; 5, 10, 15, 20 mg/m$^2$/d for 3 d; 5-20 mg/m$^2$ every other d; 5, 10, 15, 20 mg/m$^2$ every other d; 10-70 mg/m$^2$ every 4 wk; 10, 15, 20, 25, 30, 35, 40, 45, 50, 55, 60, 65, 70 mg/m$^2$ every 4 wk | 5-35 mg/m$^2$/d for 2 d; 5, 10, 15, 20, 25, 30, 35 mg/m$^2$/d for 2 d; 5, 10, 15, 20, 25 mg/m$^2$/d for 4 d | 2-78 Gy total dose; 2, 5, 10, 15, 20, 25, 30, 35, 40, 45, 50, 55, 60, 65, 70, 75, 78 Gy total dose |
| Colon Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-30 mg/m$^2$/d for 3d; 5, 10, 15, 20, 25, 30 mg/m$^2$/d for 3d | 10-185 mg/m$^2$ every 3 wk; 10, 15, 25, 35, 45, 55, 65, 75, 85, 95, 105, 115, 125, 135, 145, , 155, 165, 175, 185 mg/m$^2$ every 3 wk | 2-60 Gy total dose; 2, 5, 10, 15, 20, 25, 30, 35, 40, 45, 50, 55, 60 Gy total dose |
| Pancreatic Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 25-50 mg/m$^2$ every wk; 25, 30, 35, 40, 45, 50 mg/m$^2$ every wk; 5-15 mg/m$^2$ every 3 wk; 5, 10, 15 mg/m$^2$ every 3 wk; 10-100 mg/m$^2$ every 4 wk; 10, 15, 20, 25, 30, 35, 40, 45, 50, 55, 60, 65, 70, 75, 80, 85, 90, 95, 100 mg/m$^2$ every 4 wk | 5-35 mg/m$^2$ every wk; 5, 10, 15, 20, 25, 30, 35 mg/m$^2$ every wk; 6-100 mg/m$^2$ every 3 wk; 6, 10, 15, 20, 25, 30, 35, 40, 45, 50, 55, 60, 65, 70, 75, 80, 85, 90, 95, 100 mg/m$^2$ every 3 wk; 6-60 mg/m$^2$ every 4 wk; 6, 10, 15, 20, 25, 30, 35, 40, 45, 50, 55, 60 mg/m$^2$ every 4 wk | 2-65 Gy total dose; 2, 5, 10, 15, 20, 25, 30, 35, 40, 45, 50, 55, 60, 65 Gy total dose |
| Head/Neck Cancer | 1-200 mg/d; 1, 5, 10, 15, 20, 25, 30, 35, 40, 45, 50, 55, | 5-20 mg/m$^2$/d for 3 d; 5, 10, 15, 20 mg/m$^2$/d for 3 d; | 2-40 mg/m$^2$ every wk; 2, 5, 10, 15, 20, 25, | 2-66 Gy total dose; 2, 5, 10, 15, 20, 25, 30, 35, 40, 45, 50, 55, |

TABLE 1-continued

|   | XIAP inhibitor | Cisplatin | Docetaxel | Radiation |
|---|---|---|---|---|
|   | 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-10 mg/m$^2$ every wk; 5, 7.5, 10 mg/m$^2$ every wk; 10-65 mg/m$^2$ every 2 wk; 10, 15, 20, 25, 30, 35, 40, 45, 50, 55, 60, 65 mg/m$^2$ every 2 wk; 10-100 mg/m$^2$ every 3 wk; 10, 15, 20, 25, 30, 35, 40, 45, 50, 55, 60, 65, 70, 75, 80, 85, 90, 95, 100 mg/m$^2$ every 3 wk 5-20 mg/m$^2$/d for 5 d every 4 wk; 5, 10, 15, 20 mg/m$^2$/d for 5 d every 4 wk | 30, 35, 40 mg/m$^2$ every wk; 6-60 mg/m$^2$ every 3 wk; 6, 10, 15, 20, 25, 30, 35, 40, 45, 50, 55, 60 mg/m$^2$ every 3 wk; 6-80 mg/m$^2$ every 4 wk; 6, 10, 15, 20, 25, 30, 35, 40, 45, 50, 55, 60, 65, 70, 75, 80 mg/m$^2$ every 4 wk | 60, 66 Gy total dose |
| Non-Small Cell Lung Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-30 mg/m$^2$/d for 2 d every 3 wk; 5, 10, 15, 20, 25, 30 mg/m$^2$/d for 2 d every 3 wk; 10-100 mg/m$^2$ every 3 wk; 10, 15, 20, 25, 30, 35, 40, 45, 50, 55, 60, 65, 70, 75, 80, 85, 90, 95, 100 mg/m$^2$ every 3 wk; 10-100 mg/m$^2$/d every 4 wk; 10, 15, 20, 25, 30, 35, 40, 45, 50, 55, 60, 65, 70, 75, 80, 85, 90, 95, 100 mg/m$^2$/d every 4 wk | 5-40 mg/m$^2$ every wk; 5, 10, 15, 20, 25, 30, 35, 40 mg/m$^2$ every wk 6-175 mg/m$^2$ every 3 wk; 6, 10, 15, 25, 35, 45, 55, 65, 75, 85, 95, 105, 115, 125, 135, 145, 155, 165, 175 mg/m$^2$ 8-80 mg/m$^2$ every 4 wk; 8, 15, 20, 25, 30, 35, 40, 45, 50, 55, 60, 65, 70, 75, 80 mg/m$^2$ every 4 wk | 2-86 Gy total dose; 2, 5, 10, 15, 20, 25, 30, 35, 40, 45, 50, 55, 60, 65, 70, 75, 80, 86 Gy total dose |
| Melanoma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 10-80 mg/m$^2$ every wk; 10, 15, 20, 25, 30, 35, 40, 45, 50, 55, 60, 65, 70, 75, 80 mg/m$^2$ every wk; 5-20 mg/m$^2$/d for 4 d every 2 wk; 5, 10, 15, 20 mg/m$^2$/d for 4 d every 2 wk; 5-25 mg/m$^2$/d for 2 d every 3 wk; 5, 10, 15, 20, 25 mg/m$^2$/d for 2 d every 3 wk; 5-30 mg/m$^2$/d for 3 d every 3 wk; 5, 10, 15, 20, 25, 30 mg/m$^2$/d for 3 d every 3 wk; 10-100 mg/m$^2$ every 3 wk; 10, 15, 20, 25, 30, 35, 40, 45, 50, 55, 60, 65, 70, 75, 80, 85, 90, 95, 100 mg/m$^2$ every 3 wk | 5-100 mg/m$^2$ every 3 wk; 5, 10, 15, 20, 25, 30, 35, 40, 45, 50, 55, 60, 65, 70, 75, 80, 85, 90, 95, 100 mg/m$^2$ every 3 wk; 8-80 mg/m$^2$ every 4 wk; 8, 10, 15, 20, 25, 30, 35, 40, 45, 50, 55, 60, 65, 70, 75, 80 mg/m$^2$ every 4 wk | 2-60 Gy total dose; 2, 5, 10, 15, 20, 25, 30, 35, 40, 45, 50, 55, 60 Gy total dose |
| Ovarian Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; | 10-100 mg/m$^2$ every 3 wk; 10, 15, 20, 25, 30, 35, 40, 45, 50, 55, 60, 65, 70, 75, 80, 85, 90, 95, 100 mg/m$^2$ every 3 wk; 10-100 mg/m$^2$ every 4 wk; 10, 15, 20, 25, 30, 35, 40, 45, 50, 55, 60, 65, 70, 75, 80, 85, 90, 95, | 5-30 mg/m$^2$ every wk; 5, 10, 15, 20, 25, 30 mg/m$^2$ every wk; 5-60 mg/m$^2$ every 2 wk; 5, 10, 15, 20, 25, 30, 35, 40, 45, 50, 55, 60 mg/m$^2$ every 2 wk; 10-100 mg/m$^2$ every 3 wk; 10, 15, 20, 25, 30, 35, | 2-52 Gy total dose; 2, 5, 10, 15, 20, 25, 30, 35, 40, 45, 50, 52 Gy total dose |

TABLE 1-continued

|  | XIAP inhibitor | Cisplatin | Docetaxel | Radiation |
|---|---|---|---|---|
|  | 40, 50, 60, 70, 80, 90, 100, 120, 140, 160, 180, 200, 220, 240, 260, 280, 300, 320, 340, 360, 380, 400 mg every week | 100 mg/m$^2$ every 4 wk | 40, 45, 50, 55, 60, 65, 70, 75, 80, 85, 90, 95, 100 mg/m$^2$ every 3 wk; 6-60 mg/m$^2$ every 4 wk; 6, 10, 15, 20, 25, 30, 35, 40, 45, 50, 55, 60 mg/m$^2$ every 4 wk |  |
| Lymphoma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-25 mg/m$^2$/d for 4 d; 5, 10, 15, 20, 25 mg/m$^2$/d for 4 d; 10-75 mg/m$^2$ every 3 wk; 10, 15, 20, 25, 30, 35, 40, 45, 50, 55, 60, 65, 70, 75 mg/m$^2$ every 3 wk | 10-100 mg/m$^2$ every 3 wk; 10, 15, 20, 25, 30, 35, 40, 45, 50, 55, 60, 65, 70, 75, 80, 85, 90, 95, 100 mg/m$^2$ every 3 wk | 2-55 Gy total dose; 2, 5, 10, 15, 20, 25, 30, 35, 40, 45, 50, 55 Gy total dose |
| Hepatoma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-30 mg/m$^2$ every wk; 5, 10, 15, 20, 25, 30 mg/m$^2$ every wk; 10-80 mg/m$^2$; 10, 15, 20, 25, 30, 35, 40, 45, 50, 55, 60, 65, 70, 75, 80 mg/m$^2$ | 5-36 mg/m$^2$ every wk; 5, 10, 15, 20, 25, 30, 36 mg/m$^2$ every wk; 5-40 mg/m$^2$ every 3 wk; 5, 10, 15, 20, 25, 30, 35, 40 mg/m$^2$ every 3 wk 10-60 mg/m$^2$ every 4 wk; 10, 15, 20, 25, 30, 35, 40, 45, 50, 55, 60 mg/m$^2$ every 4 wk | 2-70 Gy total dose; 2, 5, 10, 15, 20, 25, 30, 35, 40, 45, 50, 55, 60, 65, 70 Gy total dose |
| Sarcoma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-20 mg/m$^2$/d for 5 d every 3 wk; 5, 10, 15, 20 mg/m$^2$/d for 5 d every 3 wk; 5-20 mg/m$^2$/d for 5 d every 4 wk; 5, 10, 15, 20 mg/m$^2$/d for 5 d every 4 wk; 5-30 mg/m$^2$; 5, 10, 15, 20, 25, 30 mg/m$^2$ | 4-100 mg/m$^2$ every 3 wk; 4, 10, 15, 20, 25, 30, 35, 40, 45, 50, 55, 60, 65, 70, 75, 80, 85, 90, 95, 100 mg/m$^2$ every 3 wk | 2-66 Gy total dose; 2, 5, 10, 15, 20, 25, 30, 35, 40, 45, 50, 55, 60, 66 Gy total dose |
| Chronic Lymphocytic Leukemia | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, | 5-35 mg/m$^2$/d for 2 d; 5, 10, 15, 20, 25, 30, 35 mg/m$^2$/d for 2 d; 5-25 mg/m$^2$/d for 4 d; 5, 10, 15, 20, 25 mg/m$^2$/d for 4 d |  | 2-8 Gy total dose; 2, 4, 6, 8 Gy total dose |

TABLE 1-continued

| | XIAP inhibitor | Cisplatin | Docetaxel | Radiation |
|---|---|---|---|---|
| Acute Myelogenous Leukemia | 260, 280, 300, 320, 340, 360, 380, 400 mg every week 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | | | 2-45 Gy total dose; 2, 5, 10, 15, 20, 25, 30, 35, 40, 45 Gy total dose |
| Multiple Myeloma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | | 10-75 mg/m$^2$ every 3 wk; 10, 15, 20, 25, 30, 35, 40, 45, 50, 55, 60, 65, 70, 75 mg/m$^2$ every 3 wk | 2-40 Gy total dose; 2, 5, 10, 15, 20, 25, 30, 35, 40 Gy total dose |

TABLE 2

| | Gemcitabine | CHOP | Carboplatin | Doxorubicin |
|---|---|---|---|---|
| Breast Cancer | 100-1200 mg/m$^2$ every wk; 100, 200, 300, 400, 500, 600, 700, 800, 900, 100, 1100, 1200 mg/m$^2$ every wk; 100-2,000 mg/m$^2$ every 2 wk; 100, 200, 400, 600, 800, 1000, 1200, 1400, 1600, 1800, 2000 mg/m$^2$ every 2 wk; 150-1500 mg/m$^2$ every 3 wk; 150, 300, 600, 900, 1200, 1500 mg/m$^2$ every 3 wk | C-100-1000 mg/m$^2$; H-10-50 mg/m$^2$; O-1-2 mg/m$^2$; P-10-40 mg; C-100, 200, 300, 400, 500, 600, 700, 800, 900, 1000 mg/m$^2$; H-10, 20, 30, 40, 50 mg/m$^2$; O-1, 1.2, 1.4, 1.6, 1.8, 2 mg/m$^2$; P-10, 20, 30, 40 mg | 40-265 mg/m$^2$/d for 4 d; 40, 80, 120, 160, 200, 265 mg/m$^2$/d for 4 d; 5-20 mg/m$^2$/d for 20 d; 5, 10, 15, 20 mg/m$^2$/d for 20 d; 50-300 mg/m$^2$ every 4 wk; 50, 100, 150, 200, 250, 300 mg/m$^2$ every 4 wk; 500-1600 mg/m$^2$; 500, 750, 1000, 1250, 1600 mg/m$^2$ | 2-20 mg/m$^2$ every wk; 2, 4, 6, 8, 10, 12, 14, 16, 18, 20 mg/m$^2$ every wk; 10-75 mg/m$^2$ every 2 wk; 10, 20, 30, 40, 50, 60, 75 mg/m$^2$ every 2 wk; 10-75 mg/m$^2$ every 3 wk; 10, 20, 30, 40, 50, 60, 75 mg/m$^2$ every 3 wk; 10-50 mg/m$^2$ every 4 wk; 10, 15, 20, 25, 30, 35, 40, 45, 50 mg/m$^2$ every 4 wk; 5-30 mg/m$^2$/d for 3 d every 4 wk; 5, 10, 15, 20, 25, 30 mg/m$^2$/d for 3 d every 4 wk |
| Prostate Cancer | 60-1200 mg/m$^2$ every 2 wk; 60, 120, 200, 400, 600, 800, 100, 1200 mg/m$^2$ every 2 wk | | 40-800 mg/m$^2$ every 4 wk; 40, 100, 200, 300, 400, 500, 600, 700, 800 mg/m$^2$ every 4 wk; 2-20 mg/m$^2$/d for 21 d every 6 wk; | 2-20 mg/m$^2$ every wk; 2, 4, 6, 8, 10, 12, 14, 16, 18, 20 mg/m$^2$ every wk; 4-50 mg/m$^2$ every 3 wk; 4, 10, 15, 20, 25, 30, |

TABLE 2-continued

|  | Gemcitabine | CHOP | Carboplatin | Doxorubicin |
|---|---|---|---|---|
|  |  |  | 2, 4, 8, 12, 16, 20 mg/m²/d for 21 d every 6 wk | 35, 40, 45, 50 mg/m² every 3 wk; 3-50 mg/m² every 4 wk; 3, 6, 10, 15, 20, 25, 30, 35, 40, 45, 50 mg/m² every 4 wk |
| Colon Cancer | 60-2200 mg/m² every wk; 60, 120, 200, 400, 600, 800, 1000, 1200, 1400, 1600, 1800, 2000, 2200 mg/m² every wk |  | 2-20 mg/m²/d for 20 d; 2, 4, 8, 12, 16, 20 mg/m²/d for 20 d | 3-30 mg/m² every wk; 3, 6, 10, 15, 20, 25, 30 mg/m² every wk; 1-15 mg/m²/d for 4 d; 1, 3, 5, 7, 9, 11, 13, 15 mg/m²/d for 4 d |
| Pancreatic Cancer | 100-1500 mg/m² every wk; 100, 300, 500, 700, 900, 1100, 1300, 1500 mg/m² every wk |  | 10-100 mg/m² every wk; 10, 20, 30, 40, 50, 60, 70, 80, 90, 100 mg/m² every wk; 30-300 mg/m² every 3 wk; 30, 60, 90, 120, 150, 180, 210, 240, 270, 300 mg/m² every 3 wk 20-200 mg/m² every 8 wk; 20, 40, 60, 80, 100, 120, 140, 160, 180, 200 mg/m² every 8 wk | 4-40 mg/m² every 3 wk; 4, 8, 12, 16, 20, 24, 28, 32, 36, 40 mg/m² every 3 wk; 2-40 mg/m² every 4 wk; 2, 4, 8, 12, 16, 20, 24, 28, 32, 36, 40 mg/m² every 4 wk |
| Head/Neck Cancer | 50-1800 mg/m² every wk; 50, 150, 300, 600, 900, 1200, 1500, 1800 mg/m² every wk |  | 10-90 mg/m² every wk; 10, 20, 30, 40, 50, 60, 70, 80, 90 mg/m² every wk; 10-70 mg/m²/d for 5 d every 4 wk; 10, 20, 30, 40, 50, 60, 70 mg/m²/d for 5 d every 4 wk | 2-20 mg/m² every wk; 2, 4, 6, 8, 10, 12, 14, 16, 18, 20 mg/m² every wk; 5-75 mg/m² every 3 wk; 5, 15, 25, 35, 45, 55, 65, 75 mg/m² every 3 wk; 5-30 mg/m² every 4 wk; 5, 10, 15, 20, 25, 30 mg/m² every 4 wk; 5-30 mg/m²/d for 3 d every 4 wk 5, 10, 15, 20, 25, 30 mg/m²/d for 3 d every 4 wk |
| Non-Small Cell Lung Cancer | 75-1500 mg/m² every wk; 75, 150, 300, 600, 900, 1200, 1500 mg/m² every wk |  | 4-40 mg/m²/d for 33 wk; 4, 10, 15, 20, 25, 30, 35, 40 mg/m²/d for 33 d | 5-55 mg/m² every 2 wk; 5, 10, 15, 20, 25, 30, 35, 40, 45, 50, 55 mg/m² every 2 wk; 5-50 mg/m² every 3 wk; 5, 10, 15, 20, 25, 30, 35, 40, 45, 50 mg/m² every 3 wk; 5-30 mg/m² every 4 wk; 5, 10, 15, 20, 25, 30 mg/m² every 4 wk |
| Melanoma | 80-1000 mg/m² every wk; 80, 150, 300, 500, 750, 1000 mg/m² every wk |  | 40-400 mg/m² every 3 wk; 40, 80, 120, 160, 200, 240, 280, 320, 360, 400 mg/m² every 3 wk; 30-400 mg/m² every 4 wk; 30, 50, 100, 150, 200, 250, 300, 350, 400 mg/m² every 4 wk | 5-50 mg/m² every 3 wk; 5, 10, 15, 20, 25, 30, 35, 40, 45, 50 mg/m² every 3 wk |
| Ovarian Cancer | 60-1250 mg/m² every wk; 60, 120, 250, 500, |  | 30-360 mg/m² every 4 wk; 30, 60, 90, 120, 150, | 4-50 mg/m² every wk; 4, 10, 15, 20, 25, 30, |

TABLE 2-continued

|  | Gemcitabine | CHOP | Carboplatin | Doxorubicin |
| --- | --- | --- | --- | --- |
|  | 750, 1000, 1250 mg/m$^2$ every wk; 80-2000 mg/m$^2$ every 2 wk; 80, 2090, 400, 600, 800, 1000, 1200, 1400, 1600, 1800, 2000 mg/m$^2$ every 2 wk |  | 180, 210, 240, 270, 300, 330, 360 mg/m$^2$ every 4 wk | 35, 40, 45, 50 mg/m$^2$ every wk; 5-75 mg/m$^2$ every 3 wk; 5, 15, 25, 35, 45, 55, 65, 75 mg/m$^2$ every 3 wk; 5-30 mg/m$^2$/d for 3 d every 4 wk; 5, 10, 15, 20, 25, 30 mg/m$^2$/d for 3 d every 4 wk; 5-40 mg/m$^2$/d for 4 d; 5, 10, 15, 20, 25, 30, 35, 40 mg/m$^2$/d for 4 d |
| Lymphoma | 80-1250 mg/m$^2$ every wk; 80, 150, 250, 500, 750, 1000, 1250 mg/m$^2$ every wk; 1500-2000 mg/m$^2$ every 2 wk; 1500, 1600, 1700, 1800, 1900, 2000 mg/m$^2$ every 2 wk; 2-10 mg/m$^2$/min for 12 hr; 2, 4, 6, 8, 10 mg/m$^2$/min for 12 hr | C-100-1500 mg/m$^2$; H-10-70 mg/m$^2$; O-1-2 mg/m$^2$; P-10-100 mg; C-100, 300, 500, 700, 900, 1100, 1300, 1500 mg/m$^2$; H-10, 30, 50, 70 mg/m$^2$; O-1, 1.2, 1.4, 1.6, 1.8, 2 mg/m$^2$; P-10, 20, 30, 40, 50, 60, 70, 80, 90, 100 mg | 30-300 mg/m$^2$ every 3 wk; 30, 60, 90, 120, 150, 180, 210, 240, 270, 300 mg/m$^2$ every 3 wk; 30-400 mg/m$^2$ every 4 wk; 30, 50, 100, 150, 200, 250, 300, 350, 400 mg/m$^2$ every 4 wk | 2-20 mg/m$^2$ every wk; 2, 4, 6, 8, 10, 12, 14, 16, 18, 20 mg/m$^2$ every wk; 5-75 mg/m$^2$ every 3 wk; 5, 15, 25, 35, 45, 55, 65, 75 mg/m$^2$ every 3 wk; 5-80 mg/m$^2$ every 4 wk; 5, 10, 15, 20, 25, 30, 35, 40, 45, 50, 55, 60, 65, 70, 75,80 mg/m$^2$ every 4 wk; 3-30 mg/m$^2$/d for 3 d every 4 wk; 3, 6, 10, 15, 20, 25, 30 mg/m$^2$/d for 3 d every 4 wk |
| Hepatoma |  |  | 70-700 mg/m$^2$ every 3 wk; 70, 150, 300, 450, 600, 700 mg/m$^2$ every 3 wk; 25-5 60 mg/m$^2$ every 4 wk; 25, 50, 100, 150, 200, 250, 300, 350, 400, 450, 500, 560 mg/m$^2$ every 4 wk | 2-20 mg/m$^2$ every wk; 2, 4, 6, 8, 10, 12, 14, 16, 18, 20 mg/m$^2$ every wk; 4-60 mg/m$^2$ every 3 wk; 4, 10, 15, 20, 25, 30, 35, 40, 45, 50, 55, 60 mg/m$^2$ every 3 wk; 3-50 mg/m$^2$ every 4 wk; 3, 5, 10, 15, 20, 25, 30, 35, 40, 45, 50 mg/m$^2$ every 4 wk |
| Sarcoma |  |  | 50-500 mg/m$^2$ every 3 wk; 50, 100, 150, 200, 250, 300, 350, 400, 450, 500 mg/m$^2$ every 3 wk; 30-300 mg/m$^2$ every 4 wk; 30, 60, 90, 120, 150, 180, 210, 240, 270, 300 mg/m$^2$ every 4 wk 30-300 mg/m$^2$/d for 4 d; 30, 60, 90, 120, 150, 180, 210, 240, 270, 300 mg/m$^2$/d for 4 d | 3-60 mg/m$^2$ every 3 wk; 3, 5, 10, 15, 20, 25, 30, 35, 40, 45, 50, 55, 60 mg/m$^2$ every 3 wk; 5-75 mg/m$^2$ every 4 wk; 5, 15, 25, 35, 45, 55, 65, 75 mg/m$^2$ every 4 wk 2-20 mg/m$^2$/d for 3 d; 2, 4, 6, 8, 10, 12, 14, 16, 18, 20 mg/m$^2$/d for 3 d; 1-4 mg/m$^2$/d for 4 d; 1, 1.5, 2, 2.5, 3, 3.5, 4 mg/m$^2$/d for 4 d |
| Chronic Lympho cytic Leukemia |  | C-100-1500 mg/m$^2$; H-10-70 mg/m$^2$; O-1-2 mg/m$^2$; P-10-100 mg; C-100, 300, 500, 700, 900, 1100, 1300, 1500 mg/m$^2$; H-10, 30, 50, 70 |  | 5-50 mg/m$^2$; 5, 10, 15, 20, 25, 30, 35, 40, 45, 50 mg/m$^2$; 3-36 mg/m$^2$/d for 4 d every 3 wk 3, 6, 9, 12, 15, 18, 21, 24, 27, 30, 33, 36 mg/m$^2$/d for 4 d every 3 wk |

TABLE 2-continued

|  | Gemcitabine | CHOP | Carboplatin | Doxorubicin |
| --- | --- | --- | --- | --- |
|  |  | mg/m$^2$;<br>O-1, 1.2, 1.4, 1.6, 1.8, 2 mg/m$^2$;<br>P-10, 20, 30, 40, 50, 60, 70, 80, 90, 100 mg |  |  |
| Acute Myclogenous Leukemia |  |  | 15-150 mg/m$^2$/d for 3 d every wk;<br>15, 30, 45, 60, 75, 90, 105, 120, 135, 150 mg/m$^2$/d for 3 d every wk;<br>30-315 mg/m$^2$/d for 5 d every 2 wk;<br>30, 60, 90, 120, 150, 180, 210, 240, 270, 315 mg/m$^2$/d for 5 d every 2 wk;<br>20-216 mg/m$^2$/d for 5 20, 50, 80, 110, 140, 170, 216 mg/m$^2$/d for 5 d | 2-25 mg/m$^2$ every wk;<br>2, 5, 10, 15, 20, 25 mg/m$^2$ every wk;<br>2-25 mg/m$^2$/d for 3 d;<br>2, 5, 10, 15, 20, 25 mg/m$^2$/d for 3 d;<br>5-50 mg/m$^2$;<br>5, 10, 15, 20, 25, 30, 35, 40, 45, 50 mg/m$^2$ |
| Multiple Myeloma |  |  | 10-200 mg/m$^2$/d for 4 d;<br>10, 25, 50, 75, 100, 125, 150, 175, 200 mg/m$^2$/d for 4 d;<br>40-400 mg/m$^2$ every 4 wk;<br>40, 80, 120, 160, 200, 240, 280, 320, 360, 400 mg/m$^2$ every 4 wk | 3-30 mg/m$^2$ every 3 wk;<br>3, 6, 10, 15, 20, 25, 30 mg/m$^2$ every 3 wk;<br>3-50 mg/m$^2$;<br>3, 6, 10, 15, 20, 25, 30, 35, 40, 45, 50 mg/m$^2$ |

TABLE 3

|  | Oxaliplatin | Bortezomib | Gefitinib | Bevacizumab |
| --- | --- | --- | --- | --- |
| Colon Cancer | 10-85 mg/m$^2$ every 2 wk;<br>10, 15, 20, 25, 30, 35, 40, 45, 50, 55, 60, 65, 70, 75, 80, 85 mg/m$^2$ every 2 wk;<br>10-130 mg/m$^2$ every 3 wk;<br>10, 20, 30, 40, 50, 60, 70, 80, 90, 100, 110, 120, 130 mg/m$^2$ every 3 wk |  |  | 5-10 mg/kg every 2 wk;<br>5, 6, 7, 8, 9, 10 mg/kg every 2 wk |
| Pancreatic Cancer | 10-100 mg/m$^2$ every wk;<br>10, 20, 30, 40, 50, 60, 70, 80, 90, 100 mg/m$^2$ every wk;<br>8, 15, 20, 25, 30, 35, 40, 45, 50, 55, 60, 65, 70, 75, 80, 85 mg/m$^2$ every 2 wk;<br>8-85 mg/m$^2$ every 2 wk |  |  |  |
| Head/Neck Cancer | 5-60 mg/m$^2$ every wk;<br>5, 10, 15, 20, 25, 30, 35, 40, 45, 50, 55, 60 mg/m$^2$ every wk |  | 25-500 mg/d;<br>25, 50, 75, 100, 150, 200, 250, 300, 350, 400, 450, 500 mg/d |  |
| Non-Small Cell Lung Cancer | 5-65 mg/m$^2$ every wk;<br>5, 10, 15, 20, 25, 30, 35, 40, 45, 50, 55, 60, 65 mg/m$^2$ every wk; |  | 25-500 mg/d;<br>25, 50, 75, 100, 150, 200, 250, 300, 350, 400, 450, 500 mg/d |  |

TABLE 3-continued

| | Oxaliplatin | Bortezomib | Gefitinib | Bevacizumab |
|---|---|---|---|---|
| | 10-130 mg/m² every 3 wk; 10, 20, 30, 40, 50, 60, 70, 80, 90, 100, 110, 120, 130 mg/m² every 3 wk | | | |
| Ovarian Cancer | 10-130 mg/m² every wk; 10, 20, 30, 40, 50, 60, 70, 80, 90, 100, 110, 120, 130 mg/m² every wk | | | |
| Lymphoma | | 0.2-1.04 mg/m² 2x wk; 0.2, 0.3, 0.4, 0.5, 0.6, 0.7, 0.8, 0.9, 1.04 mg/m² 2x wk | | |
| Multiple Myeloma | | 0.1-1.3 mg/m² 2x wk; 0.1, 0.2, 0.3, 0.4, 0.5, 0.6, 0.7, 0.8, 0.9, 1.0, 1.1, 1.2, 1.3 mg/m² 2x wk | | |

Therapeutic Agents Combined or Co-Administered with XIAP Inhibitor Compounds

A wide range of therapeutic agents find use with the present invention. Any therapeutic agent that can be co-administered with XIAP inhibitor compounds, or associated with XIAP inhibitor compounds is suitable for use in the methods of the present invention.

Some embodiments of the present invention provide methods for administering an effective amount of XIAP inhibitor, including acids, enantiomers, isomers, metabolites, derivatives, and pharmaceutically acceptable salts thereof and at least one additional non-XIAP inhibitor therapeutic agent (e.g., including, but not limited to, chemotherapeutic antineoplastics, antimicrobials, antivirals, antifungals, and anti-inflammatory agents) and/or therapeutic technique (e.g., surgical intervention, radiotherapies). In some of these embodiments, the subject has a disease characterized by the intracellular overexpression of XIAP proteins.

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 4 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 4

| | | |
|---|---|---|
| Aldesleukin (des-alanyl-1, serine-125 human interleukin-2) | Proleukin | Chiron Corp., Emeryville, CA |
| Alemtuzumab (IgG1κ, anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol,2-[(3-aminopropyl)amino]-, dihydrogen phosphate (ester)) | Ethyol | US Bioscience |
| Anastrozole (1,3-Benzenediacetonitrile, a, a, a', a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin*[BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0, 0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino]tetrahydro-2H-13,2-oxazaphosphorine 2-oxide monohydrate) | Cytoxan, Neosar | Bristol-Myers Squibb |

TABLE 4-continued

| | | |
|---|---|---|
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |
| Dactinomycin, actinomycin D (actinomycin produced by *Streptoinyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunonibicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17beta)-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0- | Vepesid | Bristol-Myers Squibb |

TABLE 4-continued

| Drug | Brand | Company |
|---|---|---|
| (R)-ethylidene-(beta)-D-glucopyranoside]) | | |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsuiphinyl) nonyl]estra-1,3,5-(10)-triene-3,17-beta-diol) | Faslodex | IPR Pharmaceuticals, Guayama, Puerto Rico |
| Gemcitabine (2'-deoxy-2', 2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}\bullet(c_2H_4O_2)_x$ | Zoladex Implant | AstraZeneca Pharmaceuticals |
| Hydroxyurea | Hydrea | Bristol-Myers Squibb |
| Ibritumomab Tiuxetan (inimunoconjugate resulting from a thiourea covalent bond between the monoclonal antibody Ibritumomab and the linker-chelator tiuxetan [N-[2-bis(carboxymethyl)amino]-3-(p-isotbiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochioride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7]indolizino[1,2-b]quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyll,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((-)-(S)-2,3,5,6-tetrahydro-6-phenylimidazo[2,1-b]thiazole monohydrochioride $C_{11}H_{12}N_2S\bullet HCl$) | Ergamisol | Janssen Research Foundation, Titusville, NJ |

TABLE 4-continued

| | | |
|---|---|---|
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl] L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc:, West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O']platinum) | Eloxatin | Sanofi Synthelabo, Inc., NY, NY |
| Paclitaxel (5β, 20-Epoxy-1,2a,4,7β,10β,13a-hexahydrotax-11-en-9-one 4,10-diacetate 2-benzoate 13-ester with (2R, 3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithiracin | Pfizer, Inc., NY, NY |
| Porfimer sodium | Photofrin | QLT Phototherapeutics, Inc., Vancouver, Canada |

TABLE 4-continued

| | | |
|---|---|---|
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Scierosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-.glucopyranoside] | Vumon | Bristol-Myers Squibb |
| Testolactone (13-hydroxy-3-oxo-13,17-secoandrosta-1,4-dien-17-oic acid[dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino)methyl]-4-ethyl-4,9-dihydroxy-1H-pyrano[3',4': 6,7]indolizino [1,2-b] quinoline-3,14-(4H,12H)-dione monohydrochioride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioinimunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |

TABLE 4-continued

| | | |
|---|---|---|
| Zoledronate, Zoledronic acid ((1-Hydroxy-2-imidazol-1-yl-phosphonoethyl) phosphonic acid monohydrate) | Zometa | Novartis |

In preferred embodiments, the present invention provides methods for the administration of effective amounts of XIAP inhibitor compounds and at least one conventional anticancer agent (e.g., an agent that induces apoptosis). In some preferred embodiments, the subject has a disease characterized by the overexpression of XIAP protein(s) or XIAP induced resistance to apoptotic agents. In yet other preferred embodiments, the present invention provides methods for the administration of effective amounts of XIAP inhibitor compounds and a taxane (e.g., docetaxel) compound to subjects having diseases characterized by the overexpression of XIAP.

In some embodiments, XIAP inhibitor compounds are used in combination with etoposide. As described below, embelin was able to overcome the etopside induced antiapoptotic sensitivity of cancer cell lines. Accordingly, in it contemplated that embelin and related compounds find use in overcoming the resistance of cancer cell to the apoptotic effects of etoposide and other apoptosis inducing drugs.

In some other embodiments, cisplatin and TAXOL are specifically contemplated for administration with XIAP inhibitor compounds. Cisplatin and TAXOL induce apoptosis in tumor cells. (See e.g., Lanni et al., Proc. Natl. Acad. Sci., 94:9679 (1997); Tortora et al., Cancer Research 57:5107 (1997); and Zaffaroni et al., Brit. J. Cancer 77:1378 (1998)). However, treatment with these and other chemotherapeutic agents is difficult to accomplish without subjecting the patient to significant toxicity. Many anticancer chemotherapeutic agents currently in use are generally poorly water soluble, toxic, and when given at efficacious levels affect normal cells as well as diseased cells.

For example, paclitaxel (TAXOL), is a very promising anticancer compound, and has shown excellent antitumor activity in a wide variety of tumor models such as the B16 melanoma, L1210 leukemias, MX-1 mammary tumors, and CS-1 colon tumor xenografts. However, is has poor aqueous solubility, which presents a problem in human administration. Accordingly, paclitaxel formulations typically require the use of a cremaphor to solubilize the drug. The human clinical dose range of paclitaxel is about 110-500 mg/m$^2$. For administration, paclitaxel is usually dissolved in a solution of ethanol:cremaphor (1:1) then diluted into one liter of water or other aqueous mixture. Polyethoxylated castor oil is the most often used cremaphor. The cremaphor mixture is administered by infusion. Direct administration (e.g., subcutaneous) of the cremaphor mixture results in local toxicity and low levels of activity.

In still further embodiments, the present invention provides methods for monitoring the therapeutic success of cisplatin and/or TAXOL administration in a subject. Measuring the ability of these drugs to induce apoptosis in vitro is reported to be a marker for in vivo efficacy. (Gibb, Gynecologic Oncology, 65:13 (1997)). The effectiveness of cisplatin and/or TAXOL as anticancer chemotherapeutics can be measured using techniques of the present invention for monitoring induction of apoptosis. Cisplatin and/or TAXOL are active against a wide-range of tumor types including, but not limited to, breast cancer and colon cancer. (Akutsu et al., Eur. J. Cancer 31A:2341 (1995)).

In some embodiments of the present invention, therapeutic XIAP inhibitor compound treatments further comprise one or more agents that directly cross-link nucleic acids (e.g., DNA) to facilitate DNA damage leading to a synergistic effect. Agents such as cisplatin and other DNA alkylating agents are preferred. Cisplatin has been widely used in cancer treatments. Efficacious doses used in clinical applications include, but are not limited to, about 20 mg/m$^2$ for 5 days every three weeks for a total of three courses, and 50-120 mg/m$^2$ every 3 weeks.

Agents that damage DNA also include compounds that interfere with DNA replication, mitosis, and chromosomal segregation. Such chemotherapeutic compounds include, but are not limited to, adriamycin, also known as doxorubicin, etoposide, verapamil, podophyllotoxin, and the like. These compounds are widely used in clinical settings for the treatment of neoplasms, and are typically administered as a bolus intravenous injection at doses ranging from about 25-75 mg/m$^2$ at 21 day intervals, 20-30 mg/m$^2$ every week, and similar doses for adriamycin, and 100-200 mg/m$^2$ for etoposide for three days every 3-4 weeks intravenously or double the intravenous dose when administered orally.

Agents that disrupt the synthesis and fidelity of nucleic acid precursors and subunits also lead to DNA damage and find use as chemotherapeutic agents in the present invention. A number of nucleic acid precursors have been developed. Particularly useful are agents that have undergone extensive testing and are readily available. 5-Fluorouracil (5-FU) is preferentially used by neoplastic tissues, making this agent particularly useful for targeting to neoplastic cells. The dose of 5-fluorouracil may range from about 3 to 15 mg/kg/day, although other doses may vary considerably according to various factors including stage of disease, amenability of the cells to the therapy, amount of resistance to the agent and the like.

In preferred embodiments, the anticancer agents used in the present invention are those that are amenable to co-administration with the disclosed XIAP inhibitor compounds or are otherwise associated with the disclosed XIAP inhibitor compounds such that they can be delivered into a subject, tissue, or cell without loss of fidelity of anticancer effect. For a more detailed description of cancer therapeutic agents such as a platinum complex, verapamil, podophyllotoxin, carboplatin, procarbazine, mechlorethamine, cyclophosphamide, camptothecin, ifosfamide, melphalan, chlorambucil, busulfan, nitrosourea, dactinomycin, daunorubicin, doxorubicin (adriamycin), bleomycin, plicomycin, mitomycin, etoposide (VP16), tamoxifen, TAXOL, transplatinum, 5-fluorouracil, vincristin, vinblastin and methotrexate and other similar anticancer agents, those skilled in the art are referred to any number of instructive manuals including, but not limited to, the Physician's Desk Reference and to Goodman and Gilman's "Pharmaceutical Basis of Therapeutics" ninth edition, Eds. Hardman et al., 1996.

In some embodiments, the drugs are attached to the XIAP inhibitor compounds with photocleavable linkers. For example, several heterobifunctional, photocleavable linkers that find use with the present invention are described by Ottl et al. (Ottl et al., Bioconjugate Chem., 9:143 (1998)). These linkers can be either water or organic soluble. They contain an activated ester that can react with amines or alcohols and an epoxide that can react with a thiol group. In between the two groups is 3,4-dimethoxy-6-nitrophenyl photoisomerization group, which, when exposed to near-ultraviolet light (365 nm), releases the amine or alcohol in intact form. Thus, the therapeutic agent, when linked to the compositions of the present invention using such linkers, may be released in biologically active or activatable form through exposure of the target area to near-ultraviolet light.

In an exemplary embodiment, the alcohol group of TAXOL is reacted with the activated ester of the organic-soluble linker. This product in turn is reacted with the partially-thiolated surface of appropriate dendrimers (the primary amines of the dendrimers can be partially converted to thiol-containing groups by reaction with a sub-stoichiometric amount of 2-iminothiolano). In the case of cisplatin, the amino groups of the drug are reacted with the water-soluble form of the linker. If the amino groups are not reactive enough, a primary amino-containing active analog of cisplatin, such as Pt(II) sulfadiazine dichloride (Pasani et al., Inorg. Chim. Acta 80:99 (1983) and Abel et al., Eur. J. Cancer 9:4 (1973)) can be used. Thus conjugated, the drug is inactive and will not harm normal cells. When the conjugate is localized within tumor cells, it is exposed to laser light of the appropriate near-UV wavelength, causing the active drug to be released into the cell.

Similarly, in other embodiments of the present invention, the amino groups of cisplatin (or an analog thereof) are linked with a very hydrophobic photocleavable protecting group, such as the 2-nitrobenzyloxycarbonyl group (See e.g., Pillai, V. N. R. Synthesis: 1-26 (1980)). When exposed to near-UV light (about 365 nm), the hydrophobic group is cleaved, leaving the intact drug. A number of photocleavable linkers have been demonstrated as effective anti-tumor conjugates and can be prepared by attaching cancer therapeutics, such as doxorubicin, to water-soluble polymers with appropriate short peptide linkers (See e.g., Vasey et al., Clin. Cancer Res., 5:83 (1999)). The linkers are stable outside of the cell, but are cleaved by thiolproteases once within the cell. In a preferred embodiment, the conjugate PK1 is used. As an alternative to the photocleavable linker strategy, enzyme-degradable linkers, such as Gly-Phe-Leu-Gly (SEQ ID NO: 6) may be used. An alternative to photocleavable linkers are enzyme cleavable linkers.

The present invention is not limited by the nature of the therapeutic technique. For example, other conjugates that find use with the present invention include, but are not limited to, using conjugated boron dusters for BNCT (Capala et al., Bioconjugate Chem., 7:7 (1996)), the use of radioisotopes, and conjugation of toxins such as ricin.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

IV. Research Uses

The present invention is not limited to methods and compositions for use in in vivo therapies. In certain embodiments, the XIAP inhibitors of the present invention find use in research applications. For example, in some embodiments, the inhibitors are used in cell culture assays to inhibit XIAP activity. Such cells find use in drug screening and mechanistic studies.

In some embodiments, the present invention provides kits comprising one or more XIAP inhibitors and other components for research use. In some embodiments, the kits further comprise reagents necessary for in vitro use of XIAP inhibitors including, but not limited to, buffers, cell stocks, control samples, and instructions for use of the XIAP inhibitors.

EXAMPLES

The following examples are provided to demonstrate and further illustrate certain preferred embodiments of the present invention. The examples are not to be construed as limiting the scope of the present invention.

Example 1

Development and Optimization of an FP-based Binding Assay

Figure 1:
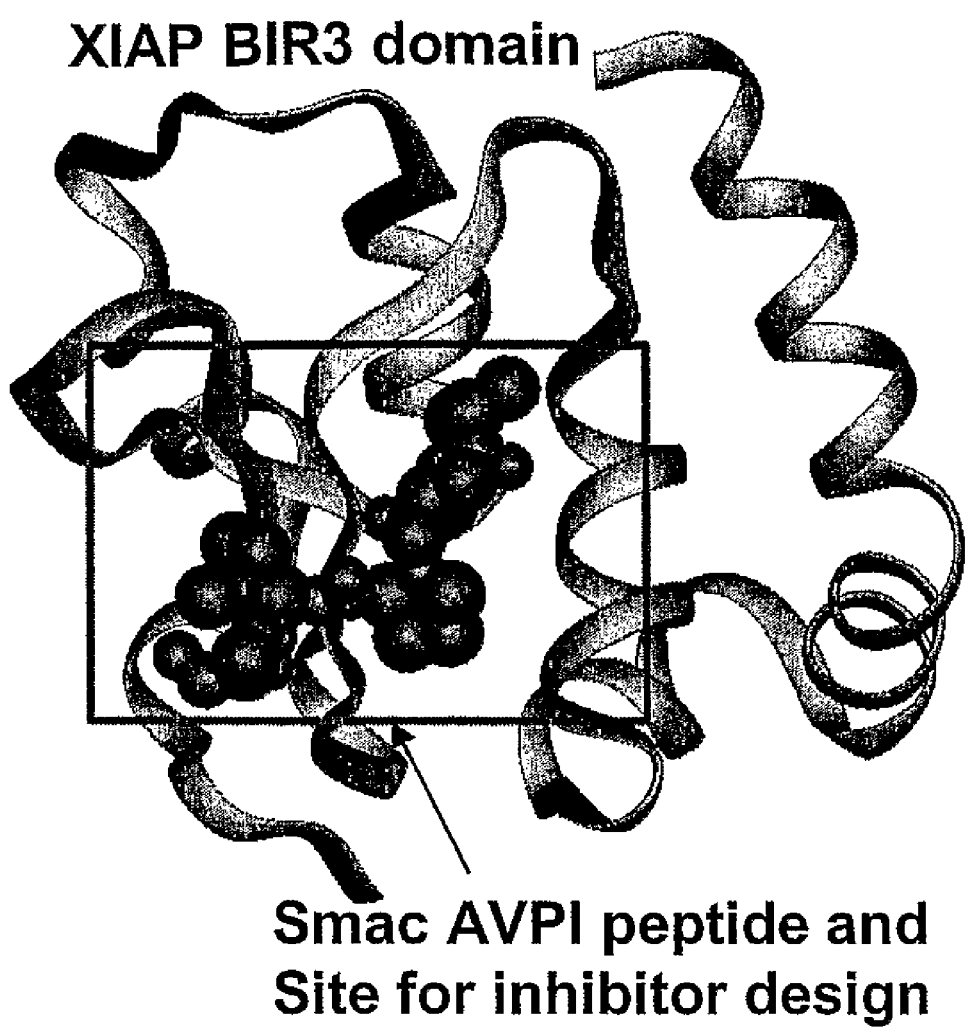
FIG. 1 presents a representation of the experimental 3D structure of the BIR3 domain of XIAP in complex with Smac peptide and the binding site used for computational structure-based database searching of traditional herbal medicine 3D structural database. The XIAP BIR3 is shown in green ribbon and the Smac peptide is shown in red balls.

A sensitive, quantitative in vitro fluorescence polarization (FP)-based binding assay was developed based upon the interactions between the XIAP BIR3 domain and Smac protein and peptide (see, e.g., Wu G, et al., Nature 408, 1008-12 (2000)). Binding of Smac to XIAP was mediated by a few amino acid residues in Smac (see FIG. 1). In particular, a 4-mer Smac peptide (AVPI; SEQ ID NO: 1) (see, e.g., Kipp, R. A., et al; Biochemistry, 41, 7344-49 (2002)) and a 9-mer peptide (AVPIAQKSE; SEQ ID NO: 2) (see, e.g., Wu G, et al; Nature 408, 1008-12 (2002)) derived from the Smac N-terminus have the same binding affinities to the XIAP BIR3 domain as the mature Smac protein. Two Smac peptides were next generated with a 6-carboxyfluorescein succinimidyl ester (FAM) fluorescence tag: the natural 9-mer Smac (AVPIAQKSEK-FAM; SEQ ID NO: 3; herein after termed S9F) and a mutated 7-mer Smac peptide (ARPFAQK-FAM; SEQ ID NO: 4; termed SM7F). Unlabeled 9-mer and 7-mer Smac peptides were used as positive controls. The human XIAP BIR3 protein (residues 241-356) with a His tag was used for this FP-based binding assay.

Figure 2A:
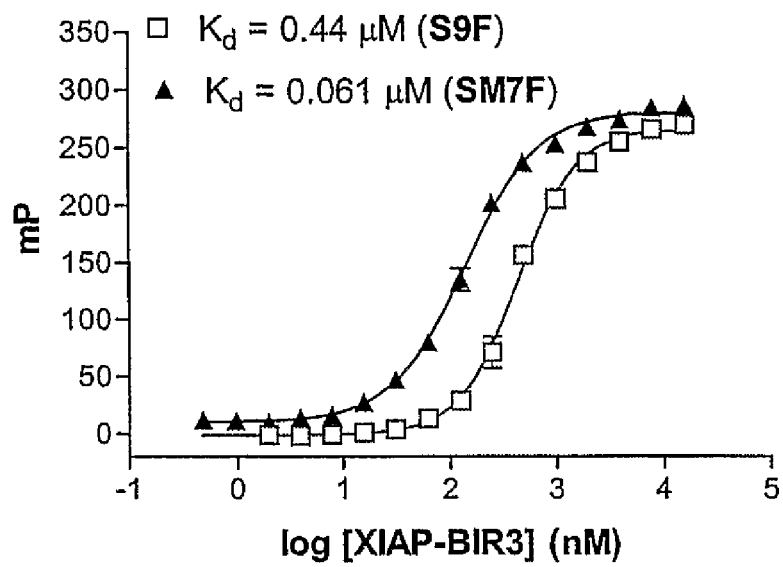
FIG. 2A presents titration curves of natural Smac peptide (AVPIAQKSEK (SEQ ID NO: 3)-FAM, termed S9F) mutated Smac peptide (and ARPFAQK (SEQ ID NO:4)-FAM, termed SM7F), labeled with 6-carboxyfluorescein succinimidyl ester with XIAP BIR3 protein.

The dissociation constants ($K_d$) of the fluorescent labeled S9F and SM7F peptides to the XIAP BIR3 protein was first determined by using a fixed concentration of the peptide (10 nM) and titrating with different concentrations of the protein (0.5 nM to 16 μM). The binding isotherms were produced by a nonlinear least-squares fit to a single-site binding model (FIG. 2A). The $K_d$ value for the natural Smac peptide (S9F) was 0.44 μM—consistent with the published $K_d$ values for the same peptide (0.48 and 0.40 μM, respectively) using two different methods (see, e.g., Wu G, et al; Nature 408, 1008-12 (2000); Kipp, R. A., Biochemistry, 41, 7344-49 (2002)). SM7F showed a higher binding affinity than S9F.

Because the fluorescent labeled mutated Smac peptide (SM7F) had a higher binding affinity than the natural Smac peptide, the mutated Smac peptide was next studied in a competitive binding assay. 10 nM of SM7F and 0.060 μM of XIAP BIR3 protein was used as the assay conditions for the following reasons: 0.060 μM concentration of XIAP is close to the $K_d$ value of SM7F; 10 nM concentration of SM7F is sufficiently low to allow the peptide tracer to be 50% saturated by 60 nM of the XIAP BIR3 protein and has sufficient fluorescence intensity to overcome the fluorescence background for some inhibitors; under these conditions, the peptide tracer is saturated at about 50% by the XIAP BIR3 protein, which makes the assay very sensitive; and the assay mP range (mP of bound peptide-mP of free peptide) is 95.2±3.0, which gives a large polarization signal window for sensitive detection of the binding of small molecule inhibitors to XIAP in competitive binding experiments.

Figure 2B:
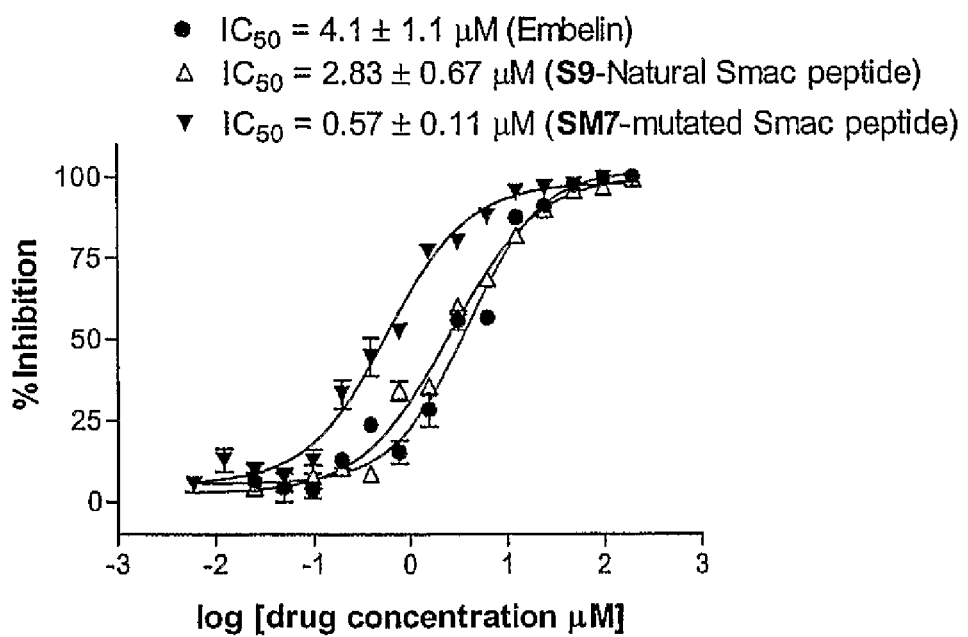
FIG. 2B presents competitive binding curves of the wild type Smac 9-mer peptide (S9), mutated Smac 7-mer peptide (SM7) and embelin.

The specificity of this assay was verified in competition experiments with corresponding unlabeled mutated Smac 7 (SM7) and the natural Smac 9-mer (S9) peptides. In both cases, the unlabeled peptides were able to abrogate binding of the labeled tracer (FIG. 2B). An $IC_{50}$ value of 2.83±0.67 µM for S9 and 0.57±0.11 µM for SM7 was obtained (FIG. 2B) from three independent experiments in triplicate. The obtained $IC_{50}$ values for these unlabeled Smac peptides were higher than the $K_d$ values of the corresponding fluorescently-labeled peptides. The ratio of the $K_d$ values between labeled SM7F and S9F (7.3 times) and the ratio of the $IC_{50}$ values for the unlabeled SM7 and S9 (5.0 times) were similar.

Example 2

Discovery of Embelin as an Inhibitor that Binds to the XIAP BIR3 Domain

The DOCK program (see, e.g., Ewing, T. J., et al., J. Comput. Aided Mol. Des. 15, 411-28 (2001)) facilitates performance of computational structure-based database searching of the TCM-3D database containing 8,221 small organic molecules with diverse chemical structures isolated from traditional Chinese medicinal herbs to identify potential small molecule inhibitors that bind to the XIAP BIR3 domain where caspase-9 and Smac bind. The high-resolution structure of the XIAP BIR3 domain in complex with Smac protein was used to define the binding site for the database searching. The sum of the electrostatic and van der Waals interactions as calculated in the DOCK program was used as the ranking score. The top 1000 candidate small molecules with the best scores were rescored using a recently developed consensus scoring program, X-score (see, e.g., Wang, R., et al., J. Comput. Aided Mol. Des. 16, 11-26 (2002)). After the re-ranking, the top 200 compounds were considered as potential small molecule inhibitors of XIAP.

Samples of 36 potential small molecule inhibitors were obtained primarily from the Developmental Therapeutics Program, the National Cancer Institute and from commercial sources in some cases, and their binding affinities to the XIAP BIR3 protein were tested in the optimized FP-based biochemical binding assay (see Example 1). Five natural products from the TCM-3D that bind to XIAP BIR3 protein and directly compete with SM7F peptide were discovered. Among these 5 inhibitors, embelin is the most potent inhibitor, with an $IC_{50}$ value of 4.1±1.1 µM (FIG. 2B) from three independent experiments in triplicate, which is slightly less potent than the natural 9-mer Smac peptide ($IC_{50}$ value=2.8±0.7 µM).

Example 3

Figure 3:
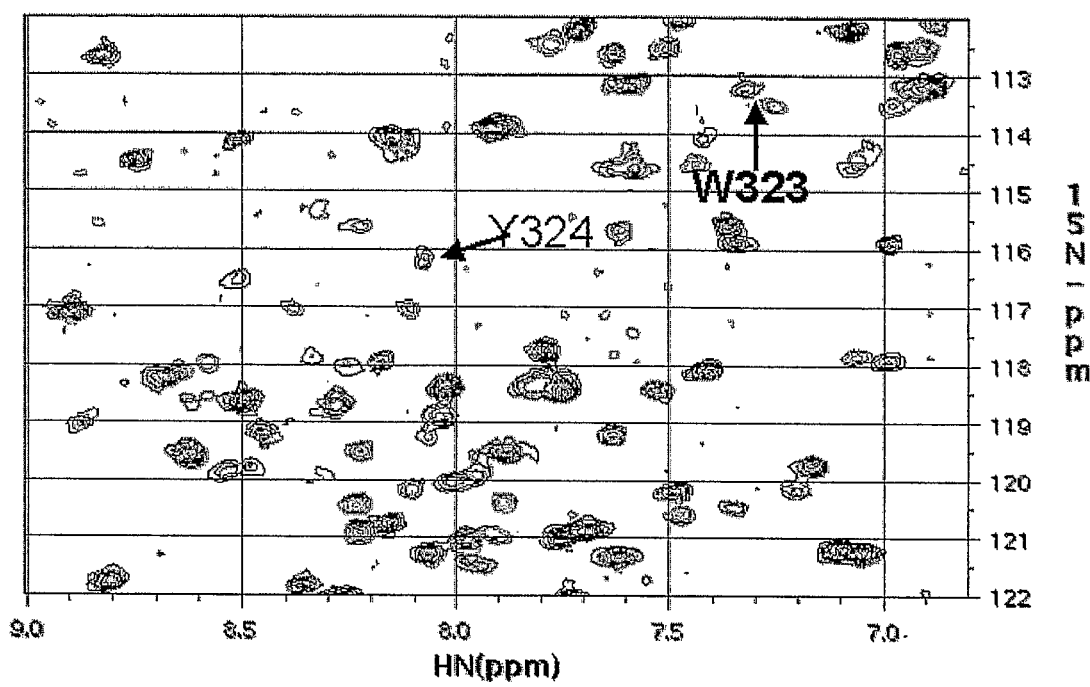
FIG. 3 presents superposition of $^{15}$N-HSQC spectra of free XIAP BIR3 domain (black) and that of the XIAP BIR3 with embelin (red). W323 and Y324 were found to be affected by embelin, similar to Smac, suggesting that embelin and Smac both interact with these common residues.

Conclusive Confirmation of the Binding of Embelin to XIAP BIR3 Where Smac/Caspase-9 Bind by NMR The FP-based binding assay showed that embelin abrogates the interaction between the Smac peptide and the XIAP BIR3 protein by displacing Smac peptide but does not provide precise direct information on which residues in XIAP embelin binds to. To conclusively confirm that embelin binds to the XIAP BIR3 domain where Smac and caspase-9 bind, and to rule out any potential false positive, an analysis using nuclear magnetic resonance (NMR) Heteronuclear Single Quantum Coherence Spectroscopy (HSQC) method was performed. The human XIAP-BIR3 domain (residues 241-356) fused to His-tag was expressed in M9 medium containing $^{15}N$ ammonium chloride to uniformly label protein with $^{15}N$ and was purified. $^{15}N$ HSQC NMR spectra were recorded with embelin and without embelin at 30° C. Overlay of two $^{15}N$ HSQC spectra of the BIR3 domain of human XIAP with embelin and without embelin is shown in FIG. 3. Based upon the partially completed backbone assignment, it was found that several residues in XIAP BIR3 protein were affected by the binding of embelin, including W323 (Tryptophan 323) and Y324 (Tyrosine 324) residues. Analysis of experimental structures of the XIAP BIR3 domain in complex with Smac protein, peptide, and caspase-9 showed that W323 and Y324 in XIAP are two residues that Smac and caspase-9 interact with (see, e.g., Shiozaki E N, et al., Mol Cell 11:519-27 (2003); Wu G, et al., Nature 408, 1008-12 (2000); Liu Z, et al., Nature 408, 1004-8 (2000)). The NMR studies of the present invention demonstrate that embelin binds to the surface groove in the XIAP BIR3 domain where Smac and caspase-9 bind.

Example 4

Figure 4:
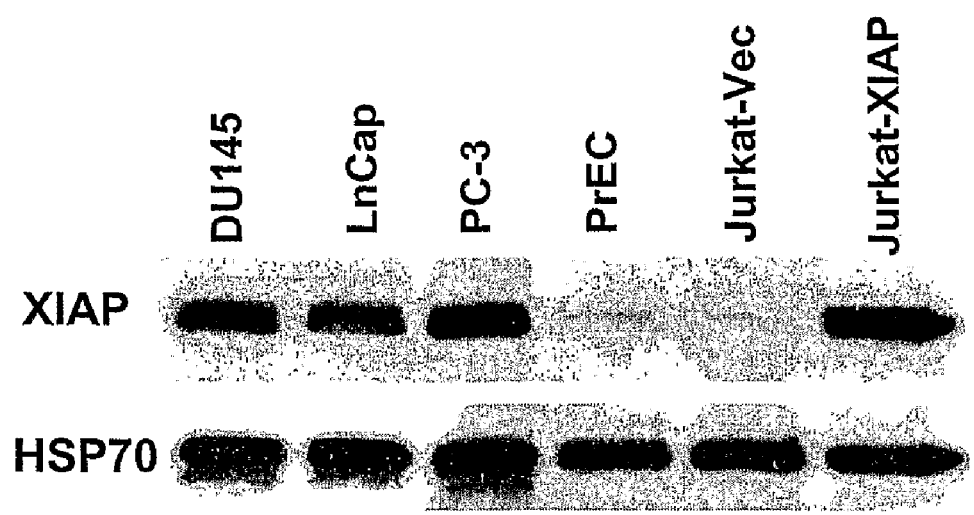
FIG. 4 present Western blot analysis of the expression of XIAP in human prostate cancer cells and normal cells. 30 µg cell lysate was loaded per lane on a 12% SDS-PAGE gel. The 57 kDa positive band is the expressed XIAP protein. PrEC.

Embelin Selectively Inhibits Cell Growth in Cancer Cells with High Levels of XIAP A Western blot analysis on XIAP expression status was performed in several prostate cancer cell lines as well as in normal prostate epithelial cells (PrEC) and in normal fibroblast WI-38 cells. It was found that the widely studied prostate cancer cell lines PC-3, LNCap, CL-1 and DU-145 have high levels of XIAP expression (FIG. 4). XIAP had a very low level in normal PrEC (FIG. 4) and in normal fibroblast WI-38 cells.

The effect of embelin on cell growth was evaluated in prostate cancer cells (PC-3 and LNCaP) versus normal cells. FIG. 5 shows the representative data of WST-1 cytotoxicity assay which had been repeated three times with similar results. Embelin inhibited cell growth of both PC-3 and LNCap cells in a dose-dependent manner, with $IC_{50}$ values of 3.7 and 5.7 µM, respectively (FIG. 5). To evaluate its selectivity, its activity in normal PrEC and in WI-38 cells was tested. The $IC_{50}$ values were found to be 20.1 µM and 19.3 µM in normal PrEC and in WI-38 cells, respectively (FIG. 5). Embelin appears to display certain selectivity for cancer cells with high levels of XIAP versus normal cells with low levels of XIAP.

Example 5

Embelin Induces Apoptosis Through Activation of Caspase-9 in Cancer Cells with High Levels of XIAP Embelin was further tested for its ability to induce apoptosis in PC-3 prostate cancer cells using Annexin V-FITC staining. Three separate experiments were performed, which showed that embelin dose-dependently induces apoptosis in PC-3 cells. The results from a representative experiment are shown in FIG. 6. After treatment of the cells with 25 and 50 µM of embelin for 48 hours, 30% and 75% of PC-3 cells underwent apoptosis, representing approximately 3- and 9-fold increase as compared to control cells, respectively (FIG. 6).

Anti-apoptotic function of XIAP is thought to be mediated by directly binding and inhibiting caspase-9 via its BIR3 domain, which leads to inhibition of caspase-3 (see, e.g., Srinivasula S M, et al., Nature 410, 112-6 (2001)). In addition, the crystal structure of caspase-9 in complex with the XIAP BIR3 domain showed that the XIAP-BIR3 domain traps caspase-9 in a monomeric state and deprives it of any possibility of catalytic activity (see, e.g., Shiozaki E N, et al., Mol Cell 11:519-27 (2003)). Smac and caspase-9 compete for the same binding pocket in XIAP BIR3. In addition, embelin binds to the BIR3 binding site in XIAP where Smac and caspase-9 bind. It was contemplated that the binding of embelin to XIAP BIR3 blocks the binding of XIAP to caspase-9, thereby subsequently leading to activation of caspase-9. The ability of embelin to activate caspase-9 in PC-3 cells was next evaluated.

Embelin effectively activates caspase-9 in a dose-dependant manner (FIGS. 7A and 7B). When treated with 20 and 40 µM of embelin for 42 hrs, which are the effective doses and optimal time point for embelin to induce early apoptosis, 33.0% and 62.1% of PC-3 cells positively stained for activated caspase-9, respectively. These represent 10- and 20-fold increase in activated caspase-9 as compared to vehicle treated control cells (3.1%), respectively. The activation of caspase-9 can be effectively inhibited by ZVAD peptide, a pan-caspase inhibitor (See FIGS. 7A and 7B). To evaluate if the activation of caspase-9 by embelin is selective for cancer cells with high levels of XIAP, embelin in normal PrEC was also tested. It was found that embelin had no significant effect as compared to vehicle treated control cells (See FIG. 7B). Embelin appears to selectively activate caspase-9 in PC-3 prostate cancer cells with high levels of XIAP and has minimal effect in normal epithelial prostate cells with low levels of XIAP.

To demonstrate that the activation of caspase-9 and early apoptosis events occurred in the same cells, Annexin V and active caspase-9 double staining was performed on PC-3 cells treated with 40 µM of embelin for 48 hrs. PC-3 cells treated with embelin showed intensive active caspase-9 staining in the cytoplasm together with Annexin V-FITC positive staining on the cell membrane, the latter being characteristic of early apoptosis. Both Annexin V-FITC and active caspase-9 double staining can be blocked by pan-caspase inhibitor ZVAD-FMK, indicating that embelin-induced apoptosis requires activation of caspases. In contrast, vehicle control cells show no staining for apoptosis and caspase-9 activation. To rule out non-specific fluorescence staining, some of the embelin-treated PC-3 cells were taken out before staining, pre-incubated with 20 µM of a caspase-9 inhibitor LEHD-FMK for 5 min, then stained for active caspase-9. Pre-incubation with excessive caspase-9 inhibitor LEHD-FMK blocked the active caspase-9 staining in Annexin V-FITC positive cells, but pre-incubation with excessive caspase-3 inhibitor ZDEVD-FMK did not. These results show that the observed red signal was specific for active caspase-9. In addition, only the apoptotic cells show co-staining of both active caspase-9 and Annexin V fluorescence, indicating that embelin-induced apoptosis is accomplished by the activation of caspase-9.

Example 6

Embelin Overcomes the Protective Effect of XIAP in Drug-Induced Apoptosis in XIAP-Transfected Jurkat Cells and has no Effect in Jurkat Cells Transfected with Vector Control XIAP overexpression renders cancer cells resistant to drug-induced apoptosis. XIAP-transfected Jurkat cells were employed to investigate whether embelin attenuates or blocks the protective effects of XIAP and enhances chemodrug-induced apoptosis. As shown in FIG. 4, Jurkat cells transfected with vector control (Jurkat-Vec) had a very low level of XIAP protein, while Jurkat cells stably transfected with human XIAP had a very high level of XIAP protein.

As shown in FIG. 8A, Jurkat cells stably transfected with XIAP (Jurkat-XIAP cells) became resistant to apoptosis induced by etoposide as compared with Jurkat cells transfected with vector control (Jurkat-Vec cells). These results indicate that XIAP-overexpression protects Jurkat cells from etoposide-induced apoptosis. Consistent with the apoptosis assay, Jurkat-XIAP cells also became less sensitive to etoposide in cell growth assay than Jurkat-Vec cells. While 94.3%±0.6% of Jurkat-Vec cells were killed with 2.5 µM of etoposide for 72 hours, only 59%±2% Jurkat-XIAP cells were killed under the same conditions. Increasing the concentration of etoposide to 10 µM only killed 85%±0.1% Jurkat-XIAP cells. These results demonstrate that XIAP overexpression protects the transfected Jurkat cells from etoposide-induced apoptosis and cytotoxicity.

The response of Jurkat-Vec and Jurkat-XIAP cells to embelin in cell growth assays was also evaluated (FIG. 9). Embelin only had a weak activity in Jurkat-Vec cells ($IC_{50}$=20 µM). Embelin also had a weak activity in Jurkat-XIAP cells, essentially identical to that in Jurkat-Vec cells. Both Jurkat-Vec and Jurkat-XIAP cells are unlikely to depend upon the protective effect of XIAP for survival since the parental Jurkat cells have a very low level of XIAP protein. As such, treatment of Jurkat-Vec and Jurkat-XIAP cells which do not rely on XIAP protein for survival with a small molecule inhibitor of XIAP such as embelin is not expected to effectively achieve cell growth inhibition or induce apoptosis.

When used in combination, embelin did not increase etoposide-induced apoptosis as compared to etoposide alone in Jurkat-Vec cells (FIG. 8B). This suggests that in cells with a very low level of. XIAP protein, XIAP protein plays a minimal role to protect cells from etoposide-induced apoptosis and consequently inhibition of XIAP using a small molecule inhibitor of XIAP (embelin) has little impact on how cells respond to etoposide. In contrast, combination of embelin and etoposide significantly increased the percentage of apoptotic cells as compared to either drug alone in Jurkat-XIAP cells and the effect appeared to be more than additive (FIG. 8B). This result suggests that when XIAP protein plays a significant role to protect cells from etoposide-induced apoptosis, inhibition of XIAP using a small molecule inhibitor of XIAP (e.g., embelin and other compounds of the present invention) overcomes the protective effect of XIAP protein to cells and restores sensitivity of cells to etoposide.

Example 7

Traditional Herbal Medicine is a Rich Resource for Molecular-Targeted Drug Discovery Embelin is a plant-based benzoquinone natural product originally isolated from the Japanese Ardisia Herb (*Herba Ardisiae Japonicae*). The Japanese Ardisia Herb has been used as a key ingredient in several traditional Chinese anti-cancer herbal recipes for the treatment of pancreatic and other types of cancer. Embelin was shown to exhibit significant antitumor activity in methylcholanthrene-induced fibrosarcoma in albino rats (see, e.g., Chitra M, et al., Chemotherapy 40, 109-13 (1994)), although the cellular molecular mechanism for its anticancer activity was not understood. The discovery that embelin is a fairly potent inhibitor of XIAP suggests that its anticancer activity is mediated at least in part by its direct binding to XIAP and inhibition of the anti-apoptotic function of XIAP protein in cancer cells.

Example 8

Traditional Chinese Medicine (TCM) Three-Dimensional Database

A searchable three-dimensional structural database (the TCM 3D-database) was built, which now contains 8,221 individual small molecule weight natural products isolated from 885 traditional herbs.

The two-dimensional chemical structure of each compound was drawn using the ISIS Draw program which was saved in the MOL format and then converted into three-dimensional (3D) structures using the Sybyl modeling package. Each 3D structure was minimized using the Sybyl program to obtain a low energy structure. The minimized structures were converted into the Mol2 format for structure-based database screening using the DOCK program (see, e.g., Ewing, T. J., et al., J. Comput. Aided Mol. Des. 15, 411-28 (2001)).

Example 9

Computational Structure-Based Database Searching

The experimental 3D structure of the BIR3 domain of XIAP in complex with Smac (pdb code 1G73) from the protein data bank was used for structure-based database searching of the TCM 3D-database. The program DOCK (version 4.0.1), was used for 3D-database screening to identify potential small molecule inhibitors of XIAP that can effectively interact with the XIAP BIR3 binding site.

The interactions between Smac protein and BIR3 domain of XIAP protein in the experimental complex structures define the crucial binding elements between them. As such, the spheres used in the DOCK program were defined by the coordinates of the N-terminal five residues of Smac in the experimental complex structure. All residues of the XIAP BIR3 protein within 8 Å from these five Smac residues were considered as part of the binding site in the screening. United atom KOLLMAN charges were assigned for atoms in the XIAP binding site using the BIOPOLYMER module in the Sybyl program. The Geisterger method as implemented in Sybyl was used to assign charges to all the compounds in the TCM 3D database.

The conformational flexibility of the compounds in the TCM 3D-database was explicitly explored during the database screening in the DOCK program (see, e.g., Ewing, T. J., et al., J. Comput. Aided Mol. Des. 15, 411-28 (2001)), and their positions and conformations were optimized using single anchor search and torsion minimization. Fifty configurations per ligand building cycle and 100 maximum anchor orientations were used in the anchor-first docking algorithm. All docked configurations were energy minimized using 10 iterations and 2 minimization cycles. A scaling factor of 0.5 was used for the electrostatic interaction calculations. The sum of the electrostatic and van der Waals interactions as calculated in the DOCK program was used as the ranking score. In the database search, the small molecules were ranked according to their scores as calculated using the energy score function in the DOCK program. The top 1000 candidate small molecules with the best scores were rescored using the recently developed consensus scoring program, X-score (see, e.g., Wang, R., J., et al., Comput. Aided Mol. Des. 16, 11-26 (2002)). After the re-ranking, the top 200 compounds were considered as potential small molecule inhibitors of XIAP. Samples of 36 compounds were obtained for testing in biochemical binding assays to the XIAP BIR3 protein.

Example 10

Fluorescence Polarization Competitive Binding Assay

A sensitive and quantitative in vitro binding assay using the fluorescence polarization (FP) based method was developed and used to determine the binding affinity of small molecules to XIAP protein. For this assay, fluorescein-5(6)-carboxamidocaproic acid N-succinimidyl ester was coupled to the lysine sidechain of the mutated peptide, ARPFAQK (SEQ ID NO:4), derived from the N terminus of a Smac peptide (SM7F), which has been shown to bind to the surface pocket of the XIAP protein with high affinity (see, e.g., Kipp, R. A., et al., Biochemistry, 41, 7344-49 (2002)). The unlabeled peptides, wild type and mutated Smac peptides, were used as the positive control in the binding assay. The recombinant XIAP BIR3 protein of human XIAP (residues 241-356) fused to His-tag was stable and soluble, and was used for the FP based binding assay.

Fluorescence polarization experiments were performed in Dynex 96-well, black, round-bottom plates (Fisher Scientific) using the Ultra plate reader (Tecan U.S. Inc., Research Triangle Park, N.C.). The dose-dependent binding experiments were carried out with serial dilutions of the active compound in DMSO. A 5 µl sample of the tested compound, and preincubated XIAP BIR3 protein (0.060 µM) and SM7F (0.010 µM) in the assay buffer (100 mM potassium phosphate, pH 7.5; 100 µg/ml bovine gamma globulin; 0.02% sodium azide), were added to each well to produce a final volume of 125 µl. For each assay, the bound peptide control containing XIAP BIR3 protein and SM7F (equivalent to 0% inhibition) and free peptide control containing only free SM7F (equivalent to 100% inhibition) were included. The plates were mixed and incubated at room temperature for 3 h to reach equilibrium. $IC_{50}$, the inhibitor concentration at which 50% of bound peptide is displaced, was determined from the plot using nonlinear least-squares analysis, and curve fitting was performed using GRAPHPAD PRISM software.

Example 11

NMR Experiments

The recombinant BIR3 domain (residues 241-356) of human XIAP protein fused to His-tag (pET-28b, Novagen) was overexpressed from *Escherichia coli* BL21(DE3) cells (Novagen) in M9 medium containing $^{15}NH_4Cl$ as the sole nitrogen source to produce uniformly $^{15}N$ labeled protein (see, e.g., Cai, M. L., et al., J. Biomol. NMR 11, 97-102 (1998); Jansson, M., et al., J. Biomol. NMR 7, 131-141 (1996)). Most of the protein was found in the soluble fraction and it was purified using TALON (Clontech) affinity chromatography, followed by G75 size-exclusion chromatography (Pharmacia).

The NMR experiments were performed on a Varian Inova 500 with pulse field gradient (PFG) HSQC, with the water flip back to maximize the signal intensity and to minimize the destruction from the water signal (see, e.g., Grzesiek, S., et al., J. Am. Chem. Soc. 115, 12593-94 (1993); Sheppard, G.

S., et al., Abstr. Pap.-Am. Chem. Soc. 213, 81 (1997)) (300 µM XIAP, 50 mM phosphate buffer pH 7.3, 2 mM DTT at 25° C.). $^{15}$N HSQC NMR spectra were recorded with samples containing 100 µM of the $^{15}$N protein in 50 mM Tris (pH 7.2), 50 µM Zn(Cl)$_2$, 1 mM DTT at 30° C. with 100 µM embelin and without it. Then two spectra were compared to identify the chemical shifts induced by the additions of the inhibitor. The NMR data were processed with the programs pipe and nmrDraw (see, e.g., Delaglio, F., et al., J. Biomol. NMR 6, 277-293 (1995); Garrett, D. S., et al., J. Magn. Reson., Ser. B 95, 214-220 (1991)).

Example 12

Cell Lines and Reagents

Human prostate cancer cell lines (PC-3, LNCap, CL-1, DU-145), and normal human fibroblast cell line WI-38 were obtained from the American Type Culture Collection (ATCC), were grown and maintained in Dulbecco's modified Eagle's medium (DMEM) containing 10% FBS (Invitrogen Corporation). Normal human prostate epithelial cells (PrEC) were obtained from Clonetics (Cambrex Inc., MD) and maintained in the special medium provided by the company. Jurkat T-cells stably transfected with either empty vector (Jurkat-Vec), or XIAP (Jurkat-XIAP) and were cultured in RPMI 1640 containing 10% fetal calf serum and 1 ug/ml puromycin. Cell cultures were maintained in a humidified incubator at 37° C. and 5% $CO_2$.

Example 13

Western Blot Analysis

To analyze the XIAP protein expression in prostate cancer cell lines, Western blot analysis was employed as described previously. Briefly, the cells were lysed at 4° C. in RIPA buffer (50 mM Tris-HCl, pH 7.4, 1% NP-40, 0.25% sodium deoxycholate, 150 mM NaCl), supplemented with a tablet of Mini protease inhibitor cocktail (Roche). The cell lysates (30 ug) were separated on 12% sodium dodecyl sulfate-polyacrylamide gel (Ready-Gel, Bio-Rad, Hercules, Calif.). The proteins were blotted onto a Hybond nitrocellulose membrane (Amersham, Arlington Heights, Ill.) and blocked with 2% nonfat dry milk plus 1% BSA (Sigma) in Tris Buffered saline (TBS)/Tween (0.1% Tween-20 in TBS). The blots were incubated with monoclonal anti-XIAP antibody (Transduction Labs, 1:2000) in 10 ml of 5% BSA for 1 hr at room temperature. The blots were washed three times with TBS/Tween, then incubated with horseradish peroxidase coupled Immunopure goat anti-mouse antibody (1:20,000) (Pierce, Rockford, Ill.) in 5% BSA for 1 hr at room temperature, washed three times again, and developed with SuperSignal chemiluminescence reagent (Pierce, Rockford, Ill.). The blots were reprobed with Heat Shock Protein 70 kDa (HSK70) antibody (Santa Cruz) as loading control.

Example 14

Cell Growth Inhibition Assay

Cell growth was determined by the MTT-based assay using Cell Proliferation Reagent WST-1 (Roche) according to the manufacturer's instruction. The WST-1 assay is a colorimetric assay that measures the reduction of WST-1 by mitochondrial succinate dehydrogenase, which belongs to the respiratory chain of the mitochondria and is active only in viable cells. The WST-1 enters the cells and passes into the mitochondria, where it is reduced to a soluble, colored formazan product. The amount of formazan dye formed directly correlates to the number of metabolically active cells in the culture. Cells (5000 cells/well) were grown in medium with 10% FBS, and various concentrations of drugs were added to the cells in triplicate. Four to five days later, WST-1 was added to each well and incubated for 1-3 hr at 37° C. Absorbance was measured with a plate reader at 450 µm with correction at 650 µm. The results are expressed as the percent of absorbance of treated wells versus that of vehicle control. $IC_{50}$, the drug concentration giving 50% growth inhibition was calculated via sigmoid curve fitting using GRAPHPAD PRISM 3.0 (GraphPad, Inc.).

Example 15

Analysis of Apoptosis

PC-3 cells, $1 \times 10^6$ cells per well in 6-well culture plates, were treated in triplicate with various concentrations of embelin for 24 or 48 hours, then trypsinized and washed with PBS. For Jurkat cells, $1 \times 10^6$ Jurkat-XIAP or Jurkat-Vec cells per well in 6-well culture plates, were treated with etoposide, embelin, or both for 15 hours. For flow cytometry apoptosis assay, cells were stained with Annexin V-FITC and propidium iodide using the Annexin-V-FLUOS Kit (Roche) according to the manufacturer's instruction. The fluorescence of Annexin V-FITC and propidium iodide of individual cells was analyzed by FACScan. The results are shown as percent of Annexin V-FITC positive apoptotic cells.

Example 16

Activation of Caspase-9 Assay $1 \times 10^6$ PC-3 cells per well in 6-well culture plates, were treated with various concentrations of embelin, or the same amount of solvent DMSO as vehicle control, for up to 48 hr. An additional control was prepared by adding the pan-caspase inhibitor Z-VAD-FMK (1 uM final) 5 min before adding embelin, to inhibit caspase activation. The cells were collected for staining of active caspase-9 by CaspGLOW Red Active Caspase-9 Staining Kit (BioVision, Inc., Mountain View, Calif.) according to the manufacturer's instructions, with modification. Briefly, to each tube containing $1 \times 10^6$ treated or control cells in 0.3 ml complete culture medium was added 1 µl of Red-LEHD-FMK and incubated for 0.5 hr at 37° C. incubator with 5% $CO_2$. For double staining with Annexin V-FITC, the cells were spun down and resuspended in 100 µl Binding Buffer containing 1× Annexin V-FITC from the Annexin-V-FLUOS Kit (Roche) and incubated at room temperature for 10 min. The cells were then washed two times with Wash Buffer from the Active Caspase-9 Staining Kit. The cells were resuspended in 0.3 ml Binding Buffer and analyzed by flow cytometry, using PI channel for active caspase-9 and FITC channel for apoptosis.

The active caspase-9 and Annexin V double stained cells were also observed under Zeiss Laser Scanning Confocal Microscope LSM 510 Meta, using the fluorescent filter sets for rhodamine (Red) and FITC (green) channels. Early apoptotic cells show green fluorescence on the cell membrane while caspase-9 positive cells show bright red staining in the cytoplasm. Photos were taken at original magnification of 630×. Cellular morphology was observed with differential interference contrast (DIC) using DIC channel.

Example 17

Computational Docking Studies

High-resolution 3D structures of XIAP are used for docking studies (see, e.g., Wu G, et al., Nature 408:1008-12 (2000); Liu Z, et al., Nature 408:1004-8 (2000)). Extensive docking studies are performed using the AUTODOCK program (see, e.g., G. M. Morris, et al., J. Comp.-Aid. Mol. Design 10, 293-304 (1996)). For each docking study, at least 10 independent docking simulations are performed. In addition, several other computational docking programs available in our laboratory are used to provide a cross-validation for computational docking results obtained from the AUTODOCK program (see, e.g., G. M. Morris, et al., J. Comp.-Aid. Mol. Design 10, 293-304 (1996)). In the docking studies, the conformational flexibility of designed inhibitors is taken into account. Extensive molecular dynamics (MD) simulation is performed to further refine the predicted complex structure for each newly designed inhibitor. The primary reason for performing extensive MD simulation is to further refine the complex structures by including the conformational flexibility of XIAP. MD simulation is performed with simulation time of 1000 pico-seconds or longer for each complex using the CHARMM program (see, e.g., B. R. Brooks, et al., J. Comput. Chem. 4, 187-217 (1983)) in explicit water environment.

If a designed inhibitor is found to be a potent inhibitor of XIAP upon synthesis and testing in our FP-based binding assay, NMR studies are carried out to investigate its binding to XIAP. NMR experiments not only provide a conclusive confirmation of the binding of the inhibitor to the BIR3 domain, but also determine which residues in XIAP interact with the inhibitor. The NMR data provides important information to validate the binding model for an inhibitor. Furthermore, if discrepancies are found between then NMR results and the predicted binding model, the NMR data is incorporated into the prediction of the binding model of the inhibitor to XIAP.

Example 18

Computational Docking Studies of SMXI-56 to XIAP

A computational docking study was performed on SMXI-56 (embelin) to investigate its detailed interactions with XIAP. Using the AutoDock program, (see, e.g., G. M. Morris, et al., J. Comp.-Aid. Mol. Design 610, 293-304 (1996)). Ten independent docking simulations were performed and it was found that 6 of them converged to a highly consistent binding model (FIG. 10A). The hydrophilic ring in SMXI-56 forms a hydrogen bonding network with residues Trp323, Gln319, Glu314 and Thr308 in XIAP, closely mimicking the hydrogen bonding network observed in the NMR and X-ray structures of Smac in complex with XIAP (FIG. 10B) (see, e.g., Wu G, et al., Nature 408:1008-12 (2000); Liu Z, et al., Nature 408: 1004-8 (2000)). The hydrophobic chain (tail) of SMXI-56 interacts with Leu292 and several surrounding residues, in a manner very similar to that of the isoleucine residue in Smac (FIG. 10B) (see, e.g., Wu G, et al., Nature 408:1008-12 (2000); Liu Z, et al., Nature 408:1004-8 (2000)). The predicted binding model provided an insight into the binding of SMXI-56 to XIAP and a structural basis for our structure-based design efforts.

Example 19

Structure-Based Design of New Analogues to Improve Potency

The scoring method (X-Score) combines the strength of three advanced empirical scoring methods, Score, Ludi Score and ChemScore (see, e.g., Wang, R. et al., J. Computer-Aided Molecular Design, 6, 11-26 (2002)). This consensus scoring method enhances the ability to carry out structure-based lead optimization efforts. The binding affinity for each proposed compound is predicted using the X-Score. Analogues with predicted binding affinities better than SMXI-56 are synthesized with high priority.

Example 20

Design of New Inhibitors Based Upon Most Promising Lead Compounds (Inhibitors) of XIAP Based upon the predicted binding model of SMXI-56 in complex with XIAP, several groups of new inhibitors were designed based upon SMXI-56, as shown in FIG. 11.

A rationale for designing compounds in GROUP I (FIG. 11) is that the hydrophilic ring forms a number of hydrogen bonds with XIAP and the terminal part of the long hydrophobic chain in SMXI-56 interacts with the hydrophobic pocket in XIAP where the isoleucine residue in Smac peptide (AVPI; SEQ ID NO: 1) interacts. The isoleucine residue in the AVPI (SEQ ID NO: 1) Smac peptide (FIG. 10B) can be replaced with a phenylalanine residue (AVPF; SEQ ID NO: 5), which binds to the XIAP 10-times better than the AVPI (SEQ ID NO: 1) Smac peptide ($K_d$=0.04 µM) (see, e.g., Kipp, R. et al. Biochemistry, 41, 7344-7349 (2002)). The designed compounds in this group therefore intend to maximize the hydrophobic interactions with the hydrophobic residues in XIAP where the isoleucine residue in the AVPI (SEQ ID NO: 1) Smac peptide or the phenylalanine residue in the AVPF (SEQ ID NO: 5) interacts. Based upon model structures, a link with 4 carbon-carbon bonds is the approximate optimal length to tether the hydrophilic aromatic ring and the hydrophobic aromatic ring. Additional small hydrophobic group are installed on the phenyl ring to further optimize the hydrophobic interaction at this site.

The rationale for designing compounds in GROUP II (FIG. 11) is to provide a constrained linker. This group of compounds was carefully modeled and found that these compounds can form optimal interactions with XIAP. Importantly, the oxygen atom in the flavone ring forms an additional hydrogen bond with XIAP, mimicking one of the hydrogen bonds formed between Smac and XIAP. A hydrophobic group is installed on the flavone ring to maximize the hydrophobic interactions with the hydrophobic pocket in XIAP where the isoleucine residue in the Smac peptide (AVPI (SEQ ID NO: 1)) binds.

The rationale for designing compounds in GROUP III (FIG. 11) is that the biphenoyl group forms several hydrogen bonds with XIAP, thus providing a mimic to the hydrophilic group in SMXI-56. Again, a flavone ring is used to provide a constrained linker between the hydrophilic group and the hydrophobic group. A hydrophobic group is installed to maximize the hydrophobic interactions with XIAP.

Example 21

Chemical Synthesis of Designed New Analogues in GROUP I

The synthesis of the new analogues in GROUP I is shown in FIG. 12. Briefly, the two hydroxyl groups in the commercially available compound 1 are protected with benzyl chloride to produce 2. Group R in the target molecules is introduced by the Wittig reaction with 2 to form 3. Benzyl group and carbon-carbon double bond in 3 can be reduced in one step using active Pd—C as the catalyst. Then, compound 4 is oxidized to benzoquinone 5 with $CrO_3$ in acetic acid using a known method (see, e.g., Ozawa, H., et al. Chem. Pharm. Bull. 16, 853-862 (1968); Yoshihira, K. et al. Chem. Pharm. Bull. 14, 1052-1053 (1966)). Benzoquinone 5 is treated with methylamine in ethanol to afford compound 6. Finally, 6 is treated with acetic acid-sulfuric acid to afford the target molecule 7.

Example 22

Chemical Synthesis of Designed New Inhibitors in Group II

The synthesis of designed constrained new analogues in GROUP II is provided in FIG. 13. Briefly, condensation of the lithium enolate prepared from 2',4'-Dihydroxyacetophenone 8 and LiHMDS with ethyl 2',5'-dibenzyloxy-benzonate affords compound 9. Cyclization of 9 by refluxing with DOWEX in 2-propanol yields compound 10 (see, e.g., van Acker, F. A. A.; et al. J. Med. Chem. 43, 3752-3760 (2000)). Alkylation of the hydroxyl group in 10 with suitable alkyl halide gives a series of alkylated compounds 11. Removal of the two benzyl groups in compound 11 by hydrogenation catalyzed by 10% Pd—C gives biphenols 12. Oxidation of these biphenols with $CrO_3$ in HOAc gives a series of 1,4-quinones 13. Addition of methyl amine to these 1,4-quinones gives compounds 14. Finally, treatment of these compounds with HOAc—$H_2SO_4$ gives analogues 15 (see, e.g., Ozawa, H., et al. Chem. Pharm. Bull. 16, 853-862 (1968); Yoshihira, K. et al. Chem. Pharm. Bull. 14, 1052-1053 (1966)).

Example 23

Chemical Synthesis of Designed New Inhibitors in GROUP III

The synthesis of designed new inhibitors in GROUP III is shown in FIG. 14. Briefly, commercially available 2',4'-dihydroxyacetophenone 16 can be transformed to lithium enolate by treating with 4 eq of LiHMDS. Condensation of this lithium enolate with ethyl 3,4-dihydroxylbenzonate yields compound 17. Cyclization of 17 by refluxing in HOAc containing catalytic amount of sulfuric acid gives compound 18 (see, e.g., Costantino, L., et al. J. Med. Chem. 42, 1881-1893 (1999); van Acker, F. A. A. et al. J. Med. Chem. 43, 3752-3760 (2000); Costantino, L.; Rastelli, G. and Albasini, A. Eur. J. Med. Chem. 31, 693-699 (1996); Cushman, M.; Nagarathnam, D. and Geahlen, R. L. J. Nat. Prod. 54, 1345-1352 (1995); Cushman, M.; Nagarathnam, D.; Burg, D. L. and Ceahlen, R. L. J. Med. Chem. 34, 798-806 (1991)). Alkylation of the hydroxyl group in 18 with suitable alkyl halide affords a series of alkylated compounds 19. Cleavage of the benzyl groups in 19 by hydrogenation catalyzed by 10% Pd—C yields a series of the designed compounds 20 in GROUP III (see, e.g., Trammell, G. L. Tetra. Lett. 1878, 1525).

Example 24

XIAP Binding Assay

An established sensitive and quantitative in vitro fluorescence polarization-based (FP) binding assay for testing of the binding affinity of each new small molecule inhibitor of XIAP is used. A principle behind this assay is competition: a fluorescent labeled Smac peptide, Smac-Flu (AVPIAQK-SEK-FAM; SEQ ID NO: 3) and a small molecule inhibitor compete for binding to XIAP. In a reaction mixture containing no inhibitor, the fluorescent tracer Smac-Flu (AVPIAQK-SEK-FAM; SEQ ID NO: 3) is added to the target protein (XIAP BIR3) to form a Smac-Flu/XIAP complex with high fluorescence polarization. The competing inhibitor is then added in microtiter wells. If the inhibitor does compete with Smac-Flu to bind to XIAP, it displaces the Smac-Flu peptide from the complex and cause a reduction in the polarization value. If the competing inhibitor does not compete with the Smac-Flu, it does not cause a reduction in the polarization value. The change in the polarization value is used to determine the relative affinity of the inhibitor for XIAP. The XIAP used in this assay is the BIR3 domain (residues 241-356) of human XIAP fused to His-tag.

The FP assays were performed as follows: each 96-well contains 50 nM Smac-Flu peptide, 985 nM XIAP protein and 5 ul tested compounds in a final volume of 20 ul. Tested compounds were serially diluted in triplicate in concentration from 0 to 100 uM. For each assay negative controls containing XIAP and Smac-Flu (equivalent to 0% inhibition) and positive controls containing only free Smac-Flu peptide (equivalent to 100% inhibition) were included on each assay plate. The polarization values were measured after 3 hour incubation when the binding reached equilibrium. $IC_{50}$ values were determined from the plot using nonlinear least-squares analysis. Curve fitting was performed using GRAPHPAD PRISM software. The $K_i$s of competing compounds were derived from the measured $IC_{50}$ and the $K_d$ of Smac-Flu in the competition assays, using the Cheng-Prusoff equation. The fluorescence intensity of each tested inhibitor is closely monitored to exclude any false positives. Furthermore, compounds with high fluorescence intensity are tested using the NMR methods described below.

Example 25

Confirming the Binding of Small Molecule Inhibitors to the XIAP BIR3 Domain with NMR Methods An advantage of the NMR approach is that it not only shows that the inhibitor binds to XIAP, but also determines precisely where it binds. The $^{15}$N-HSQC NMR method is used to confirm the binding of small molecule inhibitors, which are more potent than SMXI-56 in the FP-based binding assay. The NMR experiments provide confirmation of the binding of an inhibitor to the XIAP BIR3 domain and exclude false positive compounds. NMR experiments identify residues that are affected by the binding of the inhibitor, which are used to validate the computational docking results.

The BIR3 domain (residues 241-356) of human XIAP fused to His-tag (pET28b, Novagen) was expressed from BL21(DE3) cells in M9 medium containing $^{15}$N ammonium chloride to uniformly label protein with $^{15}$N. Most of the protein was found in the soluble fraction and it was purified using TALON (Clontech) affinity chromatography, followed by G75 size-exclusion chromatography (Pharmacia). $^{15}$N HSQC NMR spectra were recorded with samples containing 100 µM of the $^{15}$N protein in 50 mM Tris (pH 7.2), 50 µM $Zn(Cl)_2$, 1 mM DTT at 30° C. with 100 µM of small molecule inhibitor or without it. Overlay of two $^{15}$N HSQC spectra of the BIR3 domain of human XIAP with the drug and without the drug shows which residues the small molecule inhibitor binds to the protein.

Example 26

Alternative Design of New Analogs Based Upon SMXI-56

Based upon the predicted binding model, several new analogs were designed and synthesized aiming at further understanding the binding of SMXI-56 to XIAP and improving its binding affinity.

The hydrophilic dihydroxyquinone "head group" in SMXI-56 forms a number of hydrogen bonds with XIAP and primarily mimics the hydrogen bonding network formed between the alanine residue in the AVPI (SEQ ID NO: 1) Smac peptide and XIAP (FIG. 10B). In the first generation of modifications, this head group was kept as the core structure. The long hydrophobic tail group in SMXI-56 interacts with the hydrophobic pocket in XIAP and mimics the isoleucine residue in the AVPI (SEQ ID NO: 1) Smac peptide but this interaction is not optimal. Furthermore, the proline residue in the AVPI (SEQ ID NO: 1) Smac peptide played a role in controlling the conformation of the peptide. There is a strong hydrogen bond formed between the amino group in the isoleucine residue and glycine 306 in XIAP, which might play a role for the binding of the Smac to XIAP. These ideas were incorporated in the designing of new analogs. First, a phenyl ring was introduced into the new analogues with a 1,3-substitution pattern to mimic the proline ring in the AVPI (SEQ ID NO: 1) peptide. It was found that a two-carbon linker between the "head group" and this phenyl is optimal for mimicking the proline ring. Compound 1 (FIG. 15) was synthesized and was found to have an $IC_{50}$ value of 36 µM to XIAP in the competitive binding assay, approximately 10-times less potent than SMXI-56. Careful modeling showed that while the "head group" and the phenyl ring closely mimicked the alanine and the proline residues in the AVPI (SEQ ID NO: 1) peptide, the n-butyl group in Compound 1 is not optimal to interact with the hydrophobic pocket. For this reason, another phenyl ring was introduced in Compound 2 (FIG. 15) to improve the interaction with the hydrophobic pocket. The binding affinity of Compound 2 (FIG. 21) was improved by 3-times as compared to Compound 1 (FIG. 15). Introduction of a methyl group at the second phenyl ring in Compound 2 (FIG. 15) to further improve the hydrophobic interactions resulted in additional 3-fold enhancement in binding affinity for the new analog Compound 3 (FIG. 15), which was more potent than SMXI-56. Further modifications were made on Compound 3 (FIG. 15) to introduce an amide group as the linker between the two phenyl rings to allow the formation of a strong hydrogen bond between the amino group in Compound 4 (FIG. 15) and Gly 306. New analog Compound 4 (FIG. 15) was found to have an $IC_{50}$ value of 1 µM, which is 5-times more potent than SMXI-56 and is in fact approximately 2-times more potent than the natural Smac AVPI (SEQ ID NO: 1) peptide. Guided by the predicted binding model for SMXI-56 and the X-ray structure of Smac in complex with XIAP, a non-peptide, small molecule inhibitor was obtained that is more potent than the natural Smac. These results suggest that additional extensive modifications, as guided by structure-based design, will lead to the identification of potent small molecule inhibitors.

Example 27

Alternative Designing of New Inhibitors Based Upon the Most Promising Lead Compound The design of new inhibitors and synthesis and testing of these new analogs have identified a new analog 4 with a substantially improved binding affinity than the original lead compound. Accordingly, analog 4 is used as a new lead compound for design and optimization. Based upon the binding model of SMXI-56, the X-ray structure of Smac in complex with the XIAP BIR3 domain and modeling results of new analogs, two groups of new inhibitors are achieved, as shown in FIG. 16.

In alternative group I, the two phenyl rings are modified. Based upon modeling results, the right phenyl ring primarily interacts with the hydrophobic pocket in the XIAP for which the isoleucine residue in the AVPI (SEQ ID NO: 1) Smac peptide interacts. Replacement of the isoleucine residue with a phenylalanine residue results in a significant improvement in the binding affinity for the mutated Smac peptide. In a preliminary SAR study, installation of a methyl group in the para-position also improves the binding affinity by 3-fold. Extensive modifications on this phenyl ring are carried out to maximize the interactions with this hydrophobic pocket.

Analysis of the modeling results and the X-ray structure of Smac in complex with XIAP show that the middle phenyl mimics the proline ring. In the X-ray structure, the proline ring is in close contact with the Trp 323 residue in XIAP. It is hypothesized that this close contract may be important for the binding affinity and further exploration on this interaction could result in new inhibitors with improved affinity. As such, a small hydrophobic group is installed on this middle phenyl ring.

In alternative group II, the second methylene ($CH_2$) in alternative-group I is replaced with a ketone. The rationale is that in the AVPI (SEQ ID NO: 1) peptide, the carbonyl in the valine residue forms a strong hydrogen bond with the amino group of Thr 308 and this hydrogen bond may play a role for the binding of AVPI (SEQ ID NO: 1) to XIAP. Modeling results show that this new carbonyl group in alternative group II can form a hydrogen bond with the amino group of Thr 308.

The binding affinities and cellular activities can be improved by at least 10-times as compared to SMXI-56.

Example 28

Alternative Chemical Synthesis of Designed New Inhibitors in Alternative-Group I The synthesis of the new inhibitors in alternative-group I is presented in FIG. 17. Briefly, 5 is treated with n-butyllithium, followed by the reaction with the aldehyde 6 to afford 7. Aldehyde 6 is easily prepared using a published method. Hydrogenation of 7 affords 8. The final target compounds 9 are obtained by oxidation of 8 with CAN, followed by hydrolysis under a strong acidic condition.

Example 29

Alternative Chemical Synthesis of Designed New Inhibitors in Alternative-Group II The synthesis of compounds in alternative-group II is presented in FIG. 18. Briefly, compound 10 is treated with n-butyllithium, followed by the reaction with the aldehyde to afford 11. Oxidation of 11 with active $MnO_2$ affords 12. The final target compounds 13 are obtained by the treatment of 12 with CAN followed by perchloric acid and hydrochloric acid.

Example 30

XIAP Binding Activity of New Inhibitors

Several new inhibitors were synthesized and tested in the XIAP binding assay. The results are shown in Table 5.

TABLE 5

| Code | Structure | IC$_{50}$ (µM) |
|---|---|---|
| CJ-274 | 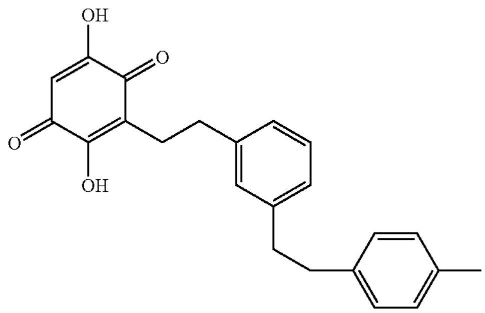 | 2.14 ± 0.73 |
| CJ-280 | 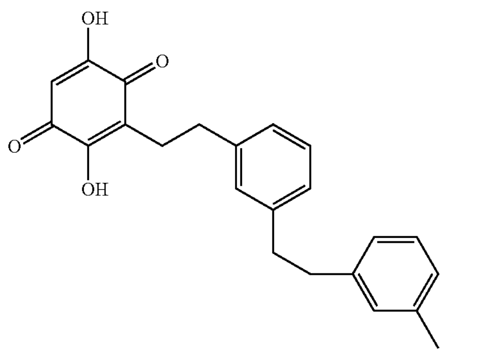 | 2.88 ± 0.51 |
| CJ-294 | 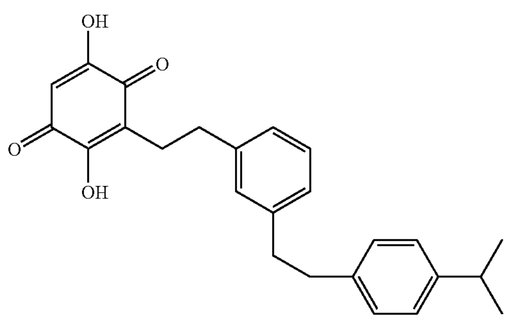 | 3.76 ± 0.25 |
| CJ-301 | 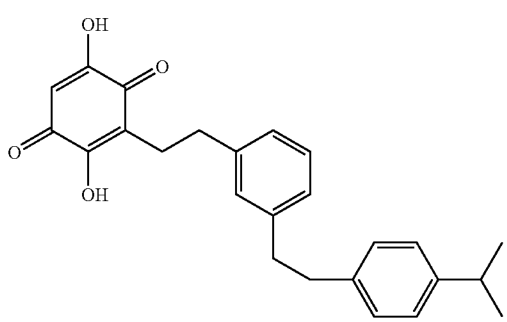 | 3.42 ± 0.31 |

TABLE 5-continued

| Code | Structure | IC$_{50}$ (μM) |
|---|---|---|
| CJ-305 | 2,5-dihydroxy-benzoquinone-CH$_2$CH$_2$-(3-phenyl)-C(O)NH-(4-methylphenyl) | 1.62 ± 0.28 |
| CJ-315 | 2,5-dihydroxy-benzoquinone-CH$_2$CH$_2$-(3-phenyl)-C(O)NH-CH$_2$-(4-methylphenyl) | 5.27 ± 1.43 |
| CJ-322 | 2,5-dihydroxy-benzoquinone-CH$_2$CH$_2$-(3-phenyl)-C(O)NH-(3-methylphenyl) | 4.89 ± 0.75 |
| CJ-323 | 2,5-dihydroxy-benzoquinone-CH$_2$CH$_2$-(3-phenyl)-C(O)NH-(2-methylphenyl) | 11.6 ± 0.96 |

TABLE 5-continued

| Code | Structure | IC$_{50}$ (μM) |
|---|---|---|
| CJ-327 | 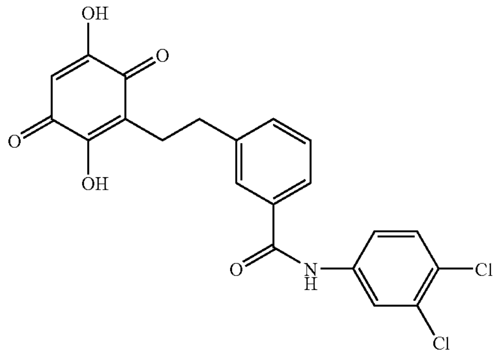 | 12.26 ± 1.09 |
| CJ-331 | 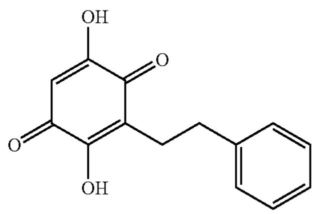 | 89.09 ± 11.28 |
| CJ-333 | 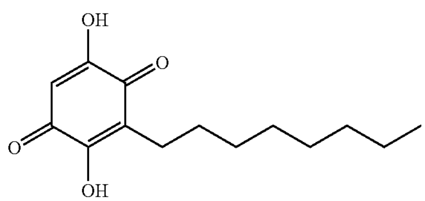 | 8.98 ± 2.00 |
| EW-1 | C$_{18}$H$_{20}$O$_4$<br>Mol. Wt.: 300.35<br>EW-1 | 21.48 ± 1.05 |
| EW-2 | C$_{14}$H$_{20}$O$_3$<br>Mol. Wt.: 236.31<br>EW-2 | 61.40 ± 9.29 |

TABLE 5-continued

| Code | Structure | IC$_{50}$ (μM) |
| --- | --- | --- |
| EW-3 | C$_{16}$H$_{16}$O$_3$<br>Mol. Wt.: 256.30<br>EW-3 | 352.93 ± 79.37 |
| EW-4 | C$_{18}$H$_{20}$O$_4$<br>Mol. Wt.: 300.35<br>EW-4 | 27.58 ± 2.76 |
| EW-5 | C$_{22}$H$_{20}$O$_4$<br>Mol. Wt.: 348.39<br>EW-5 | 3.46 ± 0.58 |
| EW-6 | C$_{30}$H$_{28}$O$_4$<br>Mol. Wt.: 452.54<br>EW-6 | 14.30 ± 2.41 |
| EW-7 | 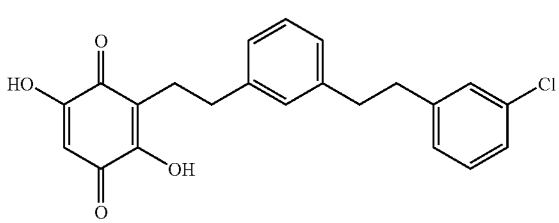 | 9.18 ± 1.90 |

TABLE 5-continued

| Code | Structure | IC$_{50}$ (μM) |
|------|-----------|----------------|
| EW-8 | 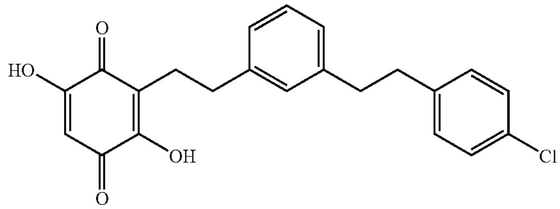 | 8.05 ± 1.48 |
| EW-9 | 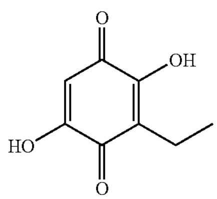 | 475.20 ± 121.80 |

All publications, patent applications, and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A compound having the structure of Formula I:

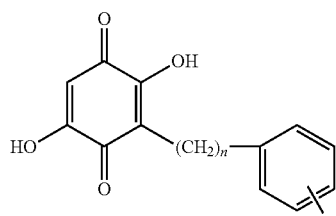

wherein R is lower alkyl or halo and n is 0-5, or a pharmaceutically acceptable salt thereof.

2. A compound having the structure of Formula II:

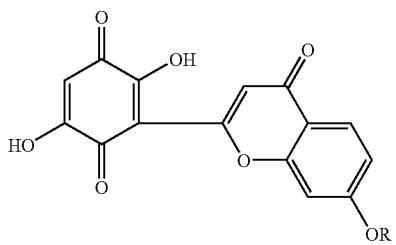

wherein R is lower alkyl, or a pharmaceutically acceptable salt thereof.

3. A compound having the structure of Formula III:

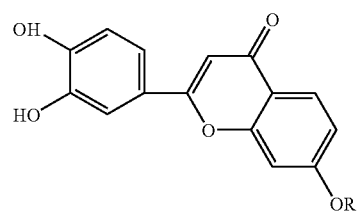

wherein R is lower alkyl, or a pharmaceutically acceptable salt thereof.

4. A compound having the structure of Formula IV:

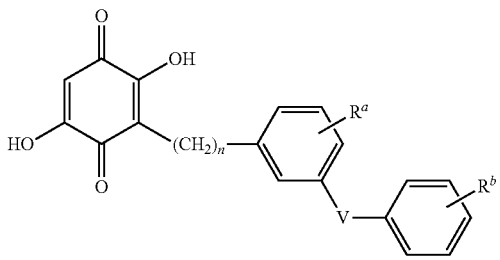

wherein $R^a$ and $R^b$ are each independently hydrogen, lower alkyl or halo, n is 1-5, and V is $(CH_2)_n$, CONH, or CONHCH$_2$, or a pharmaceutically acceptable salt thereof.

5. A pharmaceutical composition comprising a compound of any one of claims 1-4 and a pharmaceutically acceptable carrier.

6. A method of treating a hyperproliferative disease or cancer in an animal, comprising administering to said animal a therapeutically effective amount of a compound of any one of claims 1-4.

7. The method of claim 6, further comprising administering an inducer of apoptosis.

8. The method of claim 7, wherein said inducer of apoptosis is a chemotherapeutic agent.

9. The method of claim 8, wherein said chemotherapeutic agent is embelin.

10. The method of claim 7, wherein said inducer of apoptosis is radiation.

11. The method of claim 7, wherein said compound is administered prior to said inducer of apoptosis.

12. The method of claim 7, wherein said compound is administered concurrently with said inducer of apoptosis.

13. The method of claim 7, wherein said compound is administered after said inducer of apoptosis.

14. A method of inducing apoptosis in a cell comprising contacting said cell with a compound of any one of claims 1-4.

15. A method of rendering a cell sensitive to an inducer of apoptosis comprising contacting said cell with a compound of any one of claims 1-4.

16. The method of claim 15, further comprising contacting said cell with an inducer of apoptosis.

17. A kit comprising a compound of any one of claims 1-4 and instructions for administering said compound to an animal.

18. The kit of claim 17, further comprising an inducer of apoptosis.

19. The kit of claim 18, wherein said inducer of apoptosis is a chemotherapeutic agent.

20. The kit of claim 19, wherein said chemotherapeutic agent is embelin.

21. The kit of claim 17, wherein said instructions are for administering said compound to an animal having a hyperproliferative disease.

22. The kit of claim 21, wherein said hyperproliferative disease is cancer.

* * * * *

UNITED STATES PATENT AND TRADEMARK OFFICE
CERTIFICATE OF CORRECTION

| | | |
|---|---|---|
| PATENT NO. | : 7,910,621 B2 | Page 1 of 1 |
| APPLICATION NO. | : 10/594200 | |
| DATED | : March 22, 2011 | |
| INVENTOR(S) | : Jianyong Chen et al. | |

It is certified that error appears in the above-identified patent and that said Letters Patent is hereby corrected as shown below:

Title Page;
On page 1 (75), the add inventor Guoping Wang. The inventors should read as follows:

--Jianyong Chen, Ann Arbor, MI (US); Zaneta Nikolovska-Coleska, Ann Arbor, MI (US); Dajun Yang, Rockville, MD (US); Shaomeng Wang, Saline, MI (US); Haiying Sun, Ann Arbor, MI (US); Liang Xu, Ann Arbor, MI (US); Zengjian Hu, Gaithersburg, MD (US); Guoping Wang, Ann Arbor, MI (US)--

Signed and Sealed this
Tenth Day of May, 2011

David J. Kappos
*Director of the United States Patent and Trademark Office*